US007732571B2

(12) United States Patent
Lee et al.

(10) Patent No.: US 7,732,571 B2
(45) Date of Patent: Jun. 8, 2010

(54) CHICKEN GROWTH DIFFERENTIATION FACTOR-8

(75) Inventors: Se-Jin Lee, Baltimore, MD (US); Alexandra C. McPherron, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 12/173,759

(22) Filed: Jul. 15, 2008

(65) Prior Publication Data

US 2009/0017045 A1 Jan. 15, 2009

Related U.S. Application Data

(60) Division of application No. 10/997,809, filed on Nov. 23, 2004, now Pat. No. 7,399,848, which is a continuation of application No. 10/278,803, filed on Oct. 22, 2002, now Pat. No. 6,858,208, which is a continuation of application No. 09/451,501, filed on Nov. 30, 1999, now Pat. No. 6,468,535, which is a division of application No. 08/795,071, filed on Feb. 5, 1997, now Pat. No. 5,994,618, which is a continuation-in-part of application No. 08/525,596, filed as application No. PCT/US94/03019 on Mar. 18, 1994, now Pat. No. 5,827,733, which is a continuation-in-part of application No. 08/033,923, filed on Mar. 19, 1993, now abandoned.

(51) Int. Cl.
| | | |
|---|---|---|
| C07K 14/435 | (2006.01) | |
| C07K 14/46 | (2006.01) | |
| C07K 14/47 | (2006.01) | |
| C07K 14/475 | (2006.01) | |
| C07K 14/51 | (2006.01) | |
| A61K 38/16 | (2006.01) | |
| A61K 38/17 | (2006.01) | |
| A61K 38/18 | (2006.01) | |

(52) U.S. Cl. ............................ 530/350; 530/351; 514/2; 514/8; 514/12

(58) Field of Classification Search ........................ None
See application file for complete search history.

(56) References Cited

U.S. PATENT DOCUMENTS

| | | | |
|---|---|---|---|
| 5,585,479 A | 12/1996 | Hoke et al. | |
| 5,616,561 A | 4/1997 | Barcellos-Hoff | |
| 5,827,733 A | 10/1998 | Lee et al. | |
| 6,468,535 B1 | 10/2002 | Lee et al. | |

FOREIGN PATENT DOCUMENTS

| | | |
|---|---|---|
| WO | WO 91/08291 A2 | 6/1991 |
| WO | WO 94/21681 A1 | 9/1994 |
| WO | WO 98/33887 A1 | 8/1998 |
| WO | WO 99/02667 A1 | 1/1999 |
| WO | WO 99/40181 A1 | 8/1999 |
| WO | WO 99/42573 A1 | 8/1999 |

OTHER PUBLICATIONS

Bowie et al., "Deciphering the Message in Protein Sequences: Tolerance to Amino Acid Substitutions", *Science*, 247:1307-1310 (1990).
Bradley et al., "Modifying the Mouse: Design and Desire", *Biotechnology*, vol. 10, pp. 534-539, May 1992.
Callard et al., "IL-1", *The Cytokine FactsBook*, Academic Press, London, pp. 31-32 (1994).
Cameron, E.R., "Recent Advances in Transgenic Technology", *Molecular Biotechnology*, 7(3):253-265 (1997).
Constam, D. B. and Robertson, E. J., "Regulation of Bone Morphogenetic Protein Activity by Pro Domains and Proprotein Convertases", *J. Cell. Biol.*, vol. 144, No. 1, pp. 139-149, 1999.
Deli et al., "Biochemical Study of Muscle Samples from Chicken Embryos Affected by Wofatox 50 EC", *Archives of Toxicology*, vol. 8, pp. 277-279, see Abstract (1985).
Ebert et al., "A Moloney MLV-Rat Somatotropin Fusion Gene Produces Biologically Active Somatotropin in a Transgenic Pig", *Molecular Endocrinology*, vol. 2, pp. 277-283 (1988).
Eimon & Harland, "Effects of heterodimerization and proteolytic processing on Derriére and Nodal activity: implications for mesoderm induction in *Xenopus*", *Development*, 129:3089-3103 (2002).
Evock et al., "Pituitary Porcine Growth Hormone (pGH) and a Recombinant pGH Analog Stimulate Pig Growth Performance in a Similar Manner", *Journal of Animal Science*, vol. 66, No. 8, pp. 1928-1941, see Abstract (1988).
Faulkner et al., "Effect of Testosterone Propionate on Performance and Carcass Characteristics of Heifers and Cows", *Journal of Animal Science*, vol. 67, No. 8, pp. 1907-1915, see Abstract (1989).
Flakoll et al., "Influence of Alpha-Ketoisocaproate on Lamb Growth, Feed, Conversion, and Carcass Composition", *Journal of Animal Science*, vol. 69, No. 4, pp. 1461-1467, see Abstract (1991).
Gonzalez-Cadavid et al., "Organization of the human myostatin gene and expression in healthy men and HIV-infected men with muscle wasting", *Proc. Natl. Acad. Sci. USA.*, 95(25):14938-14943 (1998).
Gura, T., "Antisense Has Growing Pains", *Science*, vol. 270, pp. 575-577, Oct. 27, 1995.
Hammer et al., Genetic Engineering of Mammalian Embryos, *Journal of Animal Science*, vol. 63, pp. 269-278 (1986).
Hawley et al., "Disruption of BMP signals in embryonic *Xenopus* ectoderm leads to direct neural induction", *Genes & Development*, 9:2923-29-35 (1995).
Kappel et al., "Regulating gene expression in transgenic animals", *Current Opinion in Biotechnology*, vol. 3, pp. 548-553 (1992).
Martignoni et al, "Cancer cachexia", *Molecular Cancer*, 2(36):1-3 (2003).
Massague, J., "The TGF-.beta. Family of Growth and Differentiation Factors", *Cell*, 49:437-38, 1987.
McDowell et al., "Effects of Exogenous Growth Hormone on Milk Production and Nutrient Uptake by Muscle and Mammary Tissues of Dairy Cows in Mid-Lactation", *Australian Journal of Biological Sciences*, vol. 40, No. 3, pp. 295-306, see Abstract (1987).

(Continued)

*Primary Examiner*—Elizabeth C. Kemmerer
(74) *Attorney, Agent, or Firm*—DLA Piper LLP (US)

(57) ABSTRACT

Chicken growth differentiation factor-8 (GDF-8) is disclosed along with fragments and pharmaceutical compositions thereof.

4 Claims, 23 Drawing Sheets

OTHER PUBLICATIONS

McPherron et al., "Regulation of skeletal muscle mass in mice by a new TGF-.beta. superfamily member", *Nature*, 387(6628):83-90 (1997).

Moreadith et al., "Gene targeting in embryonic stem cells: the new physiology and metabolism", *J. Mol. Med.*, vol. 75, pp. 208-216 (1997).

Mountain et al., "Engineering antibodies for therapy", *Biotechnol., Genet, Eng.*, vol. 10, pp. 1-142 (abstract), Rev. 1992.

Mullins et al., "Perspectives Series: Molecular Medicine in Genetically Engineered Animals", *Journal of Clinical Investigation*, vol. 98, pp. S37-S40 (1996).

Ngo et al., "Computational Complexity, Protein Structure Prediction, and the Levinthal Paradox", *The Protein Folding Problem and Tertiary Structure Prediction*, Mertz & Le Grand, Editors, Birkhäuser Boston, pp. 491-495 (1994).

Onuma et al., "Multiple *nodal*-Related Genes Act Coordinately in *Xenopus* Embryogenesis", *Developmental Biology*, 241:94-105 (2002).

Rudinger, J., "Characteristics of the amino acids as components of peptide hormone sequence", *Peptide Hormones.*, Parsons J.A., Ed., University Park Press, Baltimore, London, Tokyo, pp. 1-7 (1976).

Seamark, R.F., "Progress and emerging problems in livestock transgenesis: a summary perspective", *Reproduction, Fertility and Development*, 6(5):653-657 (1994).

Strojek & Wagner, "The Use of Transgenic Animal Techniques for Livestock Improvement", *Genetic Engineering: Principles and Methods*, vol. 10, pp. 221-246 (1988).

Wall, R.J., "Transgenic Livestock: Progress and Prospects for the Future", *Theriogenology*, vol. 45, pp. 57-68 (1996).

Wan et al., "Immune Induction by a Protein Antigen and by a Peptide Segment of the Protein", *Adv. Exp. Med. Biol.*, 185:175-191 (1985).

Wells, J.A., "Additivity of Mutational Effects in Proteins", *Biochemistry*, 29(37):8509-17 (1990).

Williams & Wagner, "Transgenic animals in integrative biology: approaches and interpretations of outcome", *J. Appl. Physiol.*, 88:1119-1126 (2000).

Zhu et al., "Dominant negative myostatin produces hypertrophy without hyperplasia in muscle", *FEBS Letters*, 474:71-75 (2000).

Zhu et al., "Survey of Major Histocompatibility Complex Class II Haplotypes in Four Turkey Lines Using Restriction Fragment Length Polymorphism Analysis with Nonradioactive DNA Detection", *Poultry Science*, vol. 74, No. 7, pp. 1067-1073, see Abstract (1995).

Kambadur et al., "Mutations in *myostatin* (*GDF8*) in Double-Muscled Belgian Blue and Piedmontese Cattle", *Genome Research*, 7:910-915 (1997).

```
  1  TTAAGGTAGGAAGGATTTCAGGCTCTATTTACATAATTGTTCTTTCCTTTTCACACAGAA   60
                                                              N
 61  TCCCTTTTTAGAAGTCAAGGTGACAGACACACCCAAGAGGTCCCCGAGAGACTTTCGGCT  120
      P  F  L  E  V  K  V  T  D  T  P |K  R| S |R  R| D  F  G  L
121  TGACTGCGATGAGCACTCCACGGAATCCCGGTGCTGCCCGCTACCCCCTCACGGTCGATTT 180
      D  C  D  E  H  S  T  E  S  R  C  C  R  Y  P  L  T  V  D  F
181  TGAAGCCTTTGGATGGGACTGGATTATCGCACCCAAAAGATATAAGGCCAATTACTGCTC  240
      E  A  F  G  W  D  W  I  I  A  P  K  R  Y  K  A  N  Y  C  S
241  ACGAGAGTGTGAATTTGTGTTTTTACAAAAATATCCGCATACTCATCTTGTGCACCAAGC  300
      G  E  C  E  F  V  F  L  Q  K  Y  P  H  T  H  L  V  H  Q  A
301  AAACCCCAGAGGCTCAGCAGGCCCTTGCTGCACTCCGACAAAAATGTCTCCCATTAATAT  360
      N  P  R  G  S  A  G  P  C  C  T  P  T  K  M  S  P  I  N  M
361  GCTATATTTTAATGGCAAAGAACAAATAATATATGGCAAAATTCCAGCCATGGTAGTAGA  420
      L  Y  F  N  G  K  E  Q  I  I  Y  G  K  I  P  A  M  V  V  D
421  CCGCTGTGGGTGCTCATGAGCTTTGCATTAGGTTAGAAACTTCCCAAGTCATGGAAGGTC  480
      R  C  G  C  S
481  TTCCCCTCAATTTCGAAACTGTGAATTCCTGCAGCCCGGGGGATCCACTAGTTCTAGAGC  540
541  GGCCGCCACC  550
```

FIG. 2A

```
  1  CAAAAAGATCCAGAAGGGATTTTGGTCTTGACTGTGATGAGCACTCAACAGAATCACGAT   60
     |K  R| S |R  R| D  F  G  L  D  C  D  E  H  S  T  E  S  R  C
 61  GCTGTCGTTACCCTCTAACTGTGGATTTTGAAGCTTTTGGATGGGATTGGATTATCGCTC  120
      C  R  Y  P  L  T  V  D  F  E  A  F  G  W  D  W  I  I  A  P
121  CTAAAAGATATAAGGCCAATTACTGCTCTGGAGAGTGTGAATTTGTATTTTTACAAAAAT  180
      K  R  Y  K  A  N  Y  C  S  G  E  C  E  F  V  F  L  Q  K  Y
181  ATCCTCATACTCATCTGGTACACCAAGCAAACCCCAGAGGTTCAGCAGGCCCTTGCTGTA  240
      P  H  T  H  L  V  H  Q  A  N  P  R  G  S  A  G  P  C  C  T
241  CTCCCACAAAGATGTCTCCAATTAATATGCTATATTTTAATGGCAAAGAACAAATAATAT  300
      P  T  K  M  S  P  I  N  M  L  Y  F  N  G  K  E  Q  I  I  Y
301  ATGGGAAAATTCCAGCGATGGTAGTA  326
      G  K  I  P  A  M  V  V
```

FIG. 2B

```
GAA GAT GGG CTG AAT CCC TTT TTA GAA GTC AAA GTA ACA GAC ACA CCC AAG AGG TCC CGG
 E   D   G   L   N   P   F   L   E   V   K   V   T   D   T   P   K   R   S   R

AGA GAC TTT GGG CTT GAC TGT GAT GAA CAC TCC ACG GAA TCG CGG TGT TGT CGC TAC CCC
 R   D   F   G   L   D   C   D   E   H   S   T   E   S   R   C   C   R   Y   P

CTC ACG GTC GAT TTC GAA GCC TTT GGA TGG GAC TGG ATT ATT GCA CCC AAA AGA TAT AAG
 L   T   V   D   F   E   A   F   G   W   D   W   I   I   A   P   K   R   Y   K

GCT AAT TAC TGC TCT GGA GAG TGT GAA TTT GTG TTC TTA CAA AAA TAT CCG CAT ACT CAT
 A   N   Y   C   S   G   E   C   E   F   V   F   L   Q   K   Y   P   H   T   H

CTT GTG CAC CAA AAC CCC AGA GGC TCG GCA GGC CAA GAA ATA ATA TAT GGG AAA ATT CCA
 L   V   H   Q   N   P   R   G   S   A   G   Q   E   I   I   Y   G   K   I   P

TCT CCC ATT AAT ATG CTA TAT TTT AAT GGC AAA GAA CAA ATA ATA TAT GGG AAA ATT CCA
 S   P   I   N   M   L   Y   F   N   G   K   E   Q   I   I   Y   G   K   I   P

GCC ATG GTA GAC CGG TGT GGG TGC TCG TGA GCT TTG CAT TAG CTT TAA AAT TTC CCA
 A   M   V   D   R   C   G   C   S

AAT CGT GGA AGG TCT TCC CCT CGA AAC TGT GAA TTT ATG TAC CAC AGG CTG TAG
```

RAT GDF-8

FIG. 2C

TTA GTA AAG GCA CAA TTA TGG ATA TAC TTG AGG CAA AAA CCT ACA ACG GTG
L   V   K   A   Q   L   W   I   Y   L   R   Q   K   P   T   T   V
TTT GTG CAG ATC CTG AGA CTC ATT AAG CCC ATG AAA GAC GGT CAA GAC TAT ACT GGA ATT
F   V   Q   I   L   R   L   I   K   P   M   K   D   G   Q   D   Y   T   G   I
GGA TCT AAA TTG GAC TTT GAC ATG AAC ACG GGC CCA GGC ACT GGT CAG AGT ATT GAT GTG AAG
G   S   K   L   D   F   D   M   N   T   G   P   G   T   G   Q   S   I   D   V   K
ACA GTG CTG CAA AAT TGG CTC AAA CAA CCA GAA AGT AAC TTA GGC ATC GAA ATA AAA GCT
T   V   L   Q   N   W   L   K   Q   P   E   S   N   L   G   I   E   I   K   A
TTT GAT GAG ACT GGA CGA GAT CTT GCT GTC ACA TTC CCA GGG CCG GGT GAT GGA TTG
F   D   E   T   G   R   D   L   A   V   T   F   P   G   P   G   D   G   L
AAC CCA TTT TTA GAG GTC CAC GTT AGA ACG TCA GAA ACA ACC CGG CGC TCC CGG AGA TTT GGC
N   P   F   L   E   V   H   V   R   T   S   E   T   T   R   R   S   R   R   F   G
CTT GAC TGT GAT GAG CAC TCA ACG GAA TCA CGA TGT TGT CGC TAC CCG CTG ACA GTG GAT
L   D   C   D   E   H   S   T   E   S   R   C   C   R   Y   P   L   T   V   D
TTC GAA GCT GGA TGG GAC TGG ATT ATA GCA CCT AAA AGA AGA TAC AAA GCC AAT TAC TGC
F   E   A   G   W   D   W   I   I   A   P   K   R   Y   K   A   N   Y   C
TCC GGA GAA TGT GAA TTT GTG TTT CTA CAG AAG TAC CCG CAC ACT CAC CTG GTA CAC CAA
S   G   E   C   E   F   V   F   L   Q   K   Y   P   H   T   H   L   V   H   Q
GCA AAT CCC AGA GGC TCA GCA GGA CCT TGC TGC ACA CCC ACC AAG ATG TCC CCT ATA AAC
A   N   P   R   G   S   A   G   P   C   C   T   P   T   K   M   S   P   I   N
ATG CTG TAT TTC AAT GGA AAA GAA CAA ATA ATA TAT GGA AAG ATA CCA GCC ATG GTT GTA
M   L   Y   F   N   G   K   E   Q   I   I   Y   G   K   I   P   A   M   V   V
GAT CGT TGC GGG TGC TCA TGA GGC TGT GAG ATC CAT CTT TGA AAC TGT GAA ATT ACG TAC GCT
D   R   C   G   C   S   *

CAC CAA AAA AAA AAG CTA TAT CCC CTC ATC CAT CTT TGA

AGG CAT TGC C

CHICKEN GDF-8

FIG. 2D

```
GDF-8       SRRDFGLDCDEHSTESRCCRYPLTVDF-EAFGWQ-WIIAPKRYKANYCSGECEFVFLQKYP---
GDF-1       RPRRDAEPVLCGGPCGACRARRLYVSF-REVGWHRWVIAPRGFLANYCCGCCALPVALSGSGCPP
BMP-2       REKRQAKHKQRKRLKSSCKRHPLYVDF-SDVGWNDWIVAPPGYHAFYCHGECPFPLADHLNS---
BMP-4       KRSPKHHSQRARKKNKNCRRHSLYVDF-SDVGWNDWIVAPPGYQAFYCHGDCPFPLADHLNS---
Vgr-1       SRCSCSSDYNCSELKTACKKHELYVSF-CDLGWQDWIIAPKGYAANYCDGECSFPLNAHMNA---
OP-1        LRMANVAENSSSDQRQACKKHELYVSF-RDLGWQDWIIAPEGYAAYYCEGECAFPLNSYMNA---
BMP-5       SRMSSVGDYNTSEGKQACKKHELYVSF-RDLGWQDWIIAPEGYAAFYCDGECSFPLNAHMNA---
BMP-3       EQTLKKARRKQWIEPRNCARRYLKVDF-ADIGWSEWIISPKSFDAYYCSGACQFPMPKSLKPS---
MIS         GPGRAQRSAGATAADGPCALRELSVDL------RAERSVLIPETYQANNCQGVCGWPQSDRNPRY-
Inhibin α   ALRLLQRPPEEPAAHANCHRVALNISF-QELGWERWIVYPPSFIFHYCHGGCGLHIPPNLSLPV-
Inhibin βA  HRRRRRGLECDGKV-NICCKKQFFVSF-KDIGWNDWIIAPSGYHANYCEGECPSHIAGTSGSSL-
Inhibin βB  HRIRKRGLECDGRT-NLCCRQQFFIDF-RLIGWNDWIIAPTGYYGNYCEGSCPAYLAGVPGSAS-
TGF-β1      HRRALDTNYCFSSTEKNCCVRQLYIDFRKDLGWK-WIHEPKGYHANFCLGPCPYIWSLD------
TGF-β2      KKRALDAAYCFRNVQDNCCLRPLYIDFKRDLGWK-WIHEPKGYNANFCAGACPYLWSSD------
TGF-β3      KKRALDTNYCFRNLEENCCVRPLYIDFRQDLGWK-WVHEPKGYYANFCSGPCPYLRSAD------

GDF-8       -HTHLVHQANPRG---------SAGPCCT--PTKMSPINMLYF-NGKEQIIYGKIPAMVVDRCGCS
GDF-1       ALNHAVLRALMHA--AAPGAADLPCCV--PARLSPISVLFF-DNSDNVVLRQYEDMVVDECGCR
BMP-2       -TNHAIVQTLVNS--VNSKIPKACCV--PTELSAISMLYL-DENEKVVLKNYQDMVVEGCGCR
BMP-4       -TNHAIVQTLVNS--VNSSIPKACCV--PTELSAISMLYL-DEYDKVVLKNYQEMVVEGCGCR
Vgr-1       -TNHAIVQTLVHL--MNPEYVPKPCCA--PTKLNAISVLYF-DDNSNVILKKYRNMVVRACGCH
OP-1        -TNHAIVQTLVHF--INPETVPKPCCA--PTQLNAISVLYF-DDSSNVILKKYRNMVVRACGCH
BMP-5       -TNHAIVQTLVHL--MFPDHVPKPCCA--PTKLNAISVLYF-DDSSNVILKKYRNMVVRSCGCH
BMP-3       ---NHATIQSIVRA-VGVVPGIPEPCCV--PEKMSSLSILFF-DENKNVVLKVYPNMTVESCACR
MIS         -CNHVVLLLKMQA--RGAALARPPCCV--PTAYAGKLLISLSEER--ISAHHVPNMVATECGCR
Inhibin α   -PGAPPTPAQPYS------LLPGAQPCCAALPGTMRPLHVRTTSDGGYSFKYETVPNLLTQHCACI
Inhibin βA  -SFHSTVINHYRMRGHSPFANLKSCCV--PTKLRPMSMLYY-DDGQNIIKKDIQNMIVEECGCS
Inhibin βB  -SFHTAVVNQYRMRGLNPGT-VNSCCI--PTKLSTMSMLYF-DDEYNIVKRDVPNMIVEECGCA
TGF-β1      -TQYSKVLALYNQ--HNPGASAAPCCV--PQALEPLPIVYY-VGRKPKV-EQLSNMIVRSCKCS
TGF-β2      -TQHSRVLSLYNT--INPEASASPCCV--SQDLEPLTILYY-IGKTPKI-EQLSNMIVKSCKCS
TGF-β3      -TTHSTVLGLYNT--LNPEASASPCCV--PQDLEPLTILYY-VGRTPKV-EQLSNMVVKSCKCS
```

FIG. 3A

```
              1
human         MQKLQLCVYIYLFMLIVAGPVDLNENSEQKENVEKEGLCNACTWRQNTKSRIEAIKIQILSKLRLETAPNISKDVIRQ
murine        MMQKLQMVYIYLFMLIAAGPVDLNEGSEKENVEKEGLCNACAWRQNTRYSRIEAIKIQILSKLRLETAPNISKDAIRQ
rat                                                                                     80
chicken 81
human         LLPKAPPLRELIDQYDVQRDDSSDGSLEDDDYHATTETIITMPTESDFLMQVDGKPKCCFFKFSSKIQYNKVVKAQLWIY
murine        LLPRAPPLRELIDQYDVQRDDSSDGSLEDDDYHATTETIITMPTESDFLMQADGKPKCCFFKFSSKIQYNKVVKAQLWIY
rat                                                                                      160
chicken                                                              LVVKAQLWIY 161
human         LRPVETPTTVFVQILRLIKPMKDGTRYTGIRSLKLDMNPGTGIWQSIDVKTVLQNWLKQPESNLGIEIKALDENGHDLAV
murine        LRPVKTPTTVFVQILRLIKPMKDGTRYTGIRSLKLDMNPGTGIWQSIDVKTVLQNWLKQPESNLGIEIKALDENGHDLAV
rat                                                        SPGTGIWQSIDVKTVLQNWLKQPESNLGIEIKALDENGHDLAV
chicken       LRQVQKPTTVFVQILRLIKPMKDGTRYTGIGSLKLDMNPGTGIWQSIDVKTVLQNWLKQPESNLGIEIKAFDETGRDLAV
                                                                                          240

241
human         TFPGPGEDGLNPFLEVKVTDTPKRSRRDFGLDCDEHSTESRCCRTPLTVDFEAFGWDWIIAPKRYKANYCSGECEFVFLQ
murine        TFPGPGEDGLNPFLEVKVTDTPKRSRRDFGLDCDEHSTESRCCRYPLTVDFEAFGWDWIIAPKRYKANYCSGECEFVFLQ
rat                    EDGLNPFLEVKVTDTPKRSRRDFGLDCDEHSTESRCCRYPLTVDFEAFGWDWIIAPKRYKANYCSGECEFVFLQ
chicken       TFPGPGEDGLNPFLEVRVTDTPKRSRRDFGLDCDEHSTESRCCRYPLTVDFEAFGWDWIIAPKRYKANYCSGECEFVFLQ
                                                                                          320

321                                                                         376
human         KYPHTHLVHQANPRGSAGPCCTPTKMSPINMLYFNGKEQIIYGKIPAMVVDRCGCS
murine        KYPHTHLVHQANPRGSAGPCCTPTKMSPINMLYFNGKEQIIYGKIPAMVVDRCGCS
rat           KYPHTHLVHQANPRGSAGPCCTPTKMSPINMLYFNGKEQIIYGKIPAMVVDRCGCS
chicken       KYPHTHLVHQANPRGSAGPCCTPTKMSPINMLYFNGKEQIIYGKIPAMVVDRCGCS
```

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibin α | Inhibin βA | Inhibin βB | TGF-β1 | TGF-β2 | TGF-β3 |
|---|---|---|---|---|---|---|---|---|---|---|---|---|---|---|---|---|---|---|---|---|---|
| GDF-1 | 100 | | | | | | | | | | | | | | | | | | | | |
| GDF-2 | 33 | 100 | | | | | | | | | | | | | | | | | | | |
| GDF-3 | 50 | 42 | 100 | | | | | | | | | | | | | | | | | | |
| GDF-5 | 46 | 47 | 49 | 100 | | | | | | | | | | | | | | | | | |
| GDF-6 | 44 | 51 | 49 | 86 | 100 | | | | | | | | | | | | | | | | |
| GDF-7 | 48 | 48 | 46 | 80 | 80 | 100 | | | | | | | | | | | | | | | |
| GDF-8 | 35 | 31 | 41 | 37 | 38 | 37 | 100 | | | | | | | | | | | | | | |
| GDF-9 | 27 | 32 | 33 | 33 | 34 | 33 | 27 | 100 | | | | | | | | | | | | | |
| BMP-2 | 42 | 52 | 53 | 57 | 57 | 57 | 41 | 33 | 100 | | | | | | | | | | | | |
| BMP-4 | 43 | 51 | 50 | 57 | 56 | 57 | 38 | 34 | 92 | 100 | | | | | | | | | | | |
| Vgr-1 | 46 | 55 | 53 | 51 | 53 | 52 | 45 | 31 | 61 | 60 | 100 | | | | | | | | | | |
| OP-1 | 47 | 52 | 50 | 51 | 53 | 53 | 42 | 30 | 60 | 58 | 87 | 100 | | | | | | | | | |
| BMP-5 | 46 | 55 | 50 | 52 | 54 | 52 | 42 | 31 | 61 | 59 | 91 | 88 | 100 | | | | | | | | |
| BMP-3 | 42 | 34 | 42 | 47 | 46 | 46 | 38 | 29 | 48 | 47 | 44 | 42 | 43 | 100 | | | | | | | |
| MIS | 34 | 20 | 22 | 27 | 26 | 25 | 31 | 21 | 27 | 27 | 24 | 27 | 24 | 30 | 100 | | | | | | |
| Inhibin α | 23 | 20 | 25 | 24 | 27 | 26 | 26 | 27 | 22 | 22 | 25 | 24 | 24 | 29 | 18 | 100 | | | | | |
| Inhibin βA | 37 | 32 | 42 | 40 | 43 | 41 | 38 | 30 | 42 | 41 | 44 | 43 | 43 | 36 | 24 | 26 | 100 | | | | |
| Inhibin βB | 35 | 25 | 41 | 37 | 39 | 36 | 42 | 31 | 42 | 42 | 41 | 42 | 37 | 37 | 25 | 25 | 63 | 100 | | | |
| TGF-β1 | 33 | 26 | 36 | 33 | 35 | 36 | 34 | 23 | 35 | 34 | 35 | 37 | 34 | 32 | 28 | 23 | 41 | 35 | 100 | | |
| TGF-β2 | 32 | 28 | 31 | 34 | 36 | 35 | 37 | 25 | 34 | 33 | 37 | 38 | 35 | 32 | 23 | 22 | 37 | 34 | 74 | 100 | |
| TGF-β3 | 33 | 30 | 32 | 37 | 38 | 38 | 37 | 25 | 36 | 35 | 39 | 38 | 36 | 32 | 25 | 24 | 36 | 37 | 78 | 82 | 100 |

```
   1  GTCTCTCCGACCGTACATGCACTAATATTTCACTTGCCATTACTCAAAAGCAAAAAGAAC   60
  61  AAATAAGAACAACGGAAAAAAAAAGATTGTGCTGATTTTTAAAATGATCCAAAAACTGCA  120
                                               M  M  Q  K  L  Q
 121  AATGTATGTTTATATTTACCTGTTCATGCTGATTCCTGCTGGCCCAGTGGATCTAAATGA  180
       M  Y  V  Y  I  Y  L  F  M  L  I  A  A  G  P  V  D  L  N  E
 181  CGGCAGTCAGAGAGAACAAAAATGTCGAAAAAGAGCGGCTGTGTAATGCATGTGCCTGGAG  240
       G  S  E  R  E  E  N  V  E  K  E  G  L  C  N  A  C  A  W  R
 241  ACAAAACACGACGTACTCCACAATAGAAGCCATAAAAATTCAAATCCTCAGTAAGCTGCG  300
       Q  N  T  R  Y  S  R  I  E  A  I  K  I  Q  I  L  S  K  L  R
 301  CCTGGAAACAGCTCCTAACATCAGCAAAGATGCTATAAGACAACTTCTCCCAAGAGCCCC  360
       L  E  T  A  P [N  I  S] K  D  A  I  R  Q  L  L  P  R  A  P
 361  TCCACTCCGGGAACTGATCGATCAGTACGACGTCCAGAGGGATGACAGCAGTGATGGCTC  420
       P  L  R  E  L  I  D  Q  Y  D  V  Q  R  D  D  S  S  D  G  S
 421  TTTGGAAGATGACGATTATCACGCTACCACGGAAACAATCATTACCATGCCTACAGAGTC  480
       L  E  D  D  D  Y  H  A  T  T  E  T  I  I  T  M  P  T  E  S
 481  TGACTTTCTAATGCAAGCGGATGGCAAGCCCAAATGTTGCTTTTTTAAATTTAGCTCTAA  540
       D  F  L  M  Q  A  D  G  K  P  K  C  C  F  F  K  F  S  S  K
 541  AATACAGTACAACAAAGTAGTAAAAGCCCAACTGTGGATATATCTCAGACCCGTCAAGAC  600
       I  Q  Y  N  K  V  V  K  A  Q  L  W  I  Y  L  R  P  V  K  T
 601  TCCTACAACAGTGTTTGTGCAAATCCTGAGACTCATCAAACCCATGAAAGACCGTACAAG  660
       P  T  T  V  F  V  Q  I  L  R  L  I  K  P  M  K  D  R  T  R
 661  GTATACTGGAATCCGATCTCTGAAACTTGACATGAGCCCAGGCACTGGTATTTGGCAGAG  720
       Y  T  G  I  R  S  L  K  L  D  M  S  P  G  T  G  I  W  Q  S
 721  TATTGATGTGAAGACAGTGTTGCAAAATTGGCTCAAACAGCCTGAATCCAACTTAGGCAT  780
       I  D  V  K  T  V  L  Q  N  W  L  K  Q  P  E  S  N  L  G  I
 781  TGAAATCAAAGCTTTGGATGAGAATGGCCATGATCTTGCTGTAACCTTCCCACGACCAGG  840
       E  I  K  A  L  D  E  N  G  H  D  L  A  V  T  F  P  G  P  G
 841  AGAAGATGGGCTGAATCCCTTTTTAGAAGTCAAGGTGACAGACACACCCAAGAGGTCCCG  900
       E  D  G  L  N  P  F  L  E  V  K  V  T  D  T  P  K [R  S  R
 901  GAGAGACTTTGGCCTTGACTGCGATGAGCACTCCACGGAATCCCGGTGCTGCCGCTACCC  960
       R] D  F  G  L  D  C  D  E  H  S  T  E  S  R  C  C  R  Y  P
 961  CCTCACGGTCGATTTTGAAGCCTTTGGATGGGACTGGATTATCGCACCCAAAAGATATAA 1020
       L  T  V  D  F  E  A  F  G  W  D  W  I  I  A  P  K  R  Y  K
1021  GGCCAATTACTGCTCAGGAGAGTGTGAATTTGTGTTTTTACAAAAATATCCGCATACTCA 1080
       A  N  Y  C  S  G  E  C  E  F  V  F  L  Q  K  Y  P  H  T  H
1081  TCTTGTGCACCAAGCAAACCCCAGAGGCTCAGCAGGCCCTTGCTGCACTCCGACAAAAAT 1140
       L  V  H  Q  A  N  P  R  G  S  A  G  P  C  C  T  P  T  K  M
1141  GTCTCCCATTAATATGCTATATTTTAATGGCAAAGAACAAATAATATATGGGAAAATTCC 1200
       S  P  I  N  M  L  Y  F  N  G  K  E  Q  I  I  Y  G  K  I  P
1201  AGCCATGGTAGTAGACCGCTGTGCGTGCTCATGACCTTTGCATTAGGTTAGAAACTTCCC 1260
       A  M  V  V  D  R  C  G  C  S  •
```

FIG. 5A

```
1261  AAGTCATGGAAGGTCTTCCCCTCAATTTCGAAACTGTGAATTCAAGCACCACAGGCTGTA  1320
1321  CGCCTTGAGTATGCTCTAGTAACGTAAGCACAAGCTACAGTGTATGAACTAAAAGAGAGA  1380
1381  ATAGATGCAATGGTTGGCCATTCAACCACCAAAATAAACCATACTATAGGATGTTGTATGA  1440
1441  TTTCCAGAGTTTTTGAAATAGATGGAGATCAAATTACATTTATGTCCATATATGTATATT  1500
1501  ACAACTACAATCTAGGCAAGGAAGTGAGAGCACATCTTGTGGTCTGCTGAGTTAGGAGGG  1560
1561  TATGATTAAAAGGTAAAGTCTTATTTCCTAACAGTTTCACTTAATATTTACAGAAGAATC  1620
1621  TATATGTAGCCTTTGTAAAGTGTAGGATTGTTATCATTTAAAAACATCATGTACACTTAT  1680
1681  ATTTGTATTGTATACTTGGTAAGATAAAATTCCACAAAGTAGGAATGGGGCCTCACATAC  1740
1741  ACATTGCCATTCCTATTATAATTGGACAATCCACCACGGTGCTAATGCAGTGCTGAATGG  1800
1801  CTCCTACTGGACCTCTCGATAGAACACTCTACAAAGTACGAGTCTCTCTCTCCCTTCCAG  1860
1861  GTGCATCTCCACACACACAGCACTAAGTGTTCAATGCATTTTCTTTAAGGAAAGAAGAAT  1920
1921  CTTTTTTTCTAGAGGTCAACTTTCAGTCAACTCTAGCACAGCGGGAGTGACTGCTGCATC  1980
1981  TTAAAAGGCAGCCAAACAGTATTCATTTTTTTAATCTAAATTTCAAAATCACTGTCTGCCT  2040
2041  TTATCACATGGCAATTTTGTGGTAAAATAATGGAAATGACTGGTTCTATCAATATTGTAT  2100
2101  AAAAGACTCTGAAACAATTACATTTATATAATATGTATACAATATTGTTTTGTAAATAAG  2160
2161  TGTCTCCTTTTATATTTACTTTGGTATATTTTTACACTAATGAAATTTCAAATCATTAAA  2220
2221  GTACAAAGACATGTCATGTATCACAAAAAAGGTGACTGCTTCTATTTCAGAGTGAATTAG  2280
2281  CAGATTCAATAGTGGTCTTAAAACTCTGTATGTTAAGATTAGAAGGTTATATTACAATCA  2340
2341  ATTTATGTATTTTTTACATTATCAACTTATGGTTTCATGGTGGCTGTATCTATGAATGTG  2400
2401  GCTCCCAGTCAAATTTCAATGCCCCACCATTTTAAAAATTACAAGCATTACTAAACATAC  2460
2461  CAACATGTATCTAAAGAAATACAAATATGGTATCTCAATAACAGCTACTTTTTTATTTTA  2520
2521  TAATTTGACAATGAATACATTTCTTTTATTTACTTCAGTTTTATAAATTGGAACTTTGTT  2580
2581  TATCAAATGTATTGTACTCATAGCTAAATGAAATTATTTCTTACATAAAAATGTGTAGAA  2640
2641  ACTATAAATTAAAGTGTTTTCACATTTTTGAAAGGC  2676
```

FIG. 5B

```
   1 AAGAAAAGTAAAAGGAAGAAACAAGAACAAGAAAAAACATTATATTGATTTTAAAATCAT   60
                                                              M
  61 GCAAAAACTGCAACTCTGTGTTTATATTTACCTGTTTATGCTGATTGTTGCTGGTCCAGT  120
      Q  K  L  Q  L  C  V  Y  I  Y  L  F  M  L  I  V  A  G  P  V
 121 GGATCTAAATGAGAACAGTGAGCAAAAAGAAAATGTGGAAAAAGAGGGGCTGTGTAATGC  180
      D  L  N  E  N  S  E  Q  K  E  N  V  E  K  E  G  L  C  N  A
 181 ATGTACTTGGAGACAAAACACTAAATCTTCAAGAATAGAAGCCATTAAGATACAAATCCT  240
      C  T  W  R  Q  N  T  K  S  S  R  I  E  A  I  K  I  Q  I  L
 241 CAGTAAACTTCGTCTGGAAACAGCTCCTAACATCAGCAAAGATGTTATAAGACAACTTTT  300
      S  K  L  R  L  E  T  A  P [N  I  S] K  D  V  I  R  Q  L  L
 301 ACCCAAAGCTCCTCCACTCCGGGAACTGATTGATCAGTATGATGTCCAGAGGGATGACAG  360
      P  K  A  P  P  L  R  E  L  I  D  Q  Y  D  V  Q  R  D  D  S
 361 CAGCGATGGCTCTTTGGAAGATGACGATTATCACGCTACAACGGAAACAATCATTACCAT  420
      S  D  G  S  L  E  D  D  D  Y  H  A  T  T  E  T  I  I  T  M
 421 GCCTACAGAGTCTGATTTTCTAATGCAAGTGGATGGAAAACCCAAATGTTGCTTCTTTAA  480
      P  T  E  S  D  F  L  M  Q  V  D  G  K  P  K  C  C  F  F  K
 481 ATTTAGCTCTAAAATACAATACAATAAAGTAGTAAAGGCCCAACTATGGATATATTTGAG  540
      F  S  S  K  I  Q  Y  N  K  V  V  K  A  Q  L  W  I  Y  L  R
 541 ACCCGTCGAGACTCCTACAACAGTGTTTGTGCAAATCCTGAGACTCATCAAACCTATGAA  600
      P  V  E  T  P  T  T  V  F  V  Q  I  L  R  L  I  K  P  M  K
 601 AGACGGTACAAGGTATACTGGAATCCGATCTCTGAAACTTGACATGAACCCAGGCACTGG  660
      D  G  T  R  Y  T  G  I  R  S  L  K  L  D  M  N  P  G  T  G
 661 TATTTGGCAGAGCATTGATGTGAAGACAGTGTTGCAAAATTGGCTCAAACAACCTGAATC  720
      I  W  Q  S  I  D  V  K  T  V  L  Q  N  W  L  K  Q  P  E  S
 721 CAACTTAGGCATTGAAATAAAAGCTTTAGATGAGAATGGTCATGATCTTGCTGTAACCTT  780
      N  L  G  I  E  I  K  A  L  D  E  N  G  H  D  L  A  V  T  F
 781 CCCAGGACCAGGAGAAGATCGGCTGAATCCGTTTTTAGAGGTCAAGGTAACAGACACACC  840
      P  G  P  G  E  D  G  L  N  P  F  L  E  V  K  V  T  D  T  P
 841 AAAAAGATCCAGAAGGGATTTTGGTCTTGACTGTGATGAGCACTCAACAGAATCACGATG  900
      K [R  S  R  R] D  F  G  L  D  C  D  E  H  S  T  E  S  R  C
 901 CTGTCGTTACCCTCTAACTGTGGATTTTGAAGCTTTTGGATGGGATTGGATTATCGCTCC  960
      C  R  Y  P  L  T  V  D  F  E  A  F  G  W  D  W  I  I  A  P
 961 TAAAAGATATAAGGCCAATTACTGCTCTGGAGAGTGTGAATTTGTATTTTTACAAAAATA 1020
      K  R  Y  K  A  N  Y  C  S  G  E  C  E  F  V  F  L  Q  K  Y
1021 TCCTCATACTCATCTGGTACACCAAGCAAACCCCAGAGGTTCAGCAGGCCCTTGCTGTAC 1080
      P  H  T  H  L  V  H  Q  A  N  P  R  G  S  A  G  P  C  C  T
1081 TCCCACAAAGATGTCTCCAATTAATATGCTATATTTTAATGGCAAAGAACAAATAATATA 1140
      P  T  K  M  S  P  I  N  M  L  Y  F  N  G  K  E  Q  I  I  Y
1141 TGGAAAAATTCCAGCGATGGTAGTAGACCGCTGTGGGTGCTCATGAGATTTATATTAAGC 1200
      G  K  I  P  A  M  V  V  D  R  C  G  C  S  *
```

FIG. 5C

```
1201 GTTCATAACTTCCTAAAACATGGAACGTTTTCCCCTCAACAATTTTGAAGCTGTGAAATT 1260
1261 AAGTACCACACGCTATAGGCCTAGAGTATGCTACAGTCACTTAAGCATAAGCTACAGTAT 1320
1321 GTAAACTAAAAGGGGGAATATATGCAATGGTTGGCATTTAACCATCCAAACAAATCATAC 1380
1381 AAGAAAGTTTTATGATTTCCAGAGTTTTTGAGCTAGAAGGAGATCAAATTACATTTATGT 1440
1441 TCCTATATATTACAACATCGGCGACGAAATGAAAGCGATTCTCCTTGAGTTCTGATGAAT 1500
1501 TAAACGAGTATGCTTTAAAGTCTATTTCTTTAAAGTTTTGTTTAATATTTACAGAAAAAT 1560
1561 CCACATACAGTATTCGTAAAATGCAGGATTGTTATATACCATCATTCGAATCATCCTTAA 1620
1621 ACACTTGAATTTATATTGTATGGTAGTATACTTGGTAAGATAAAATTCCACAAAAATAGG 1680
1681 GATGGTGCAGCATATGCAATTTCCATTCCTATTATAATTGACACAGTACATTAACAATCC 1740
1741 ATGCCAACGGTGCTAATACGATAGGCTGAATGTCTGAGGCTACCAGGTTTATCACATAAA 1800
1801 AAACATTCAGTAAAATAGTAAGTTTCTCTTTTCTTCAGGTGCATTTTCCTACACCTCCAA 1860
1861 ATGAGGAATGGATTTTCTTTAATGTAAGAAGAATCATTTTTCTAGAGGTTGGCTTTCAAT 1920
1921 TCTGTAGCATACTTCGAGAAACTGCCATTATCTTAAAACGCAGTCAAATGGTGTTTGTTTT 1980
1981 TATCAAAATGTCAAAATAACATACTTCGAGAAGTATGTAATTTTGTCTTTGGAAAATTAC 2040
2041 AACACTGCCTTTGCAACACTGCAGTTTTTATGGTAAAATAATAGAAATGATCCACTCTAT 2100
2101 CAATATTGTATAAAAAGACTGAAACAATGCATTTATATAATATGTATACAATATTGTTTT 2160
2161 GTAAATAAGTGTCTCCTTTTTTATTTACTTTGGTATATTTTTACACTAAGGACATTTCAA 2220
2221 ATTAAGTACTAAGGCACAAACACATGTCATGCATCACAGAAAAGCAACTACTTATATTTC 2280
2281 AGAGCAAAATTAGCAGATTAAATAGTGGTCTTAAAACTCCATATGTTAATGATTAGATGGT 2340
2341 TATATTACAATCATTTTATATTTTTTACATGATTAACATTCACTTATGGATTCATGATG 2400
2401 GCTGTATAAAGTGAATTTGAAATTTCAATGGTTTACTGTCATTGTGTTTAAATCTCAACG 2460
2461 TTCCATTATTTTAATACTTGCAAAAACATTACTAAGTATACCAAAATAATTGACTCTATT 2520
2521 ATCTGAAATGAAGAATAAACTGATGCTATCTCAACAATAACTGTTACTTTTATTTTATAA 2580
2581 TTTGATAATGAATATATTTCTGCATTTATTTACTTCTGTTTTGTAAATTGGGATTTTGTT 2640
2641 AATCAAATTTATTGTACTATGACTAAATGAAATTATTTCTTACATCTAATTTGTAGAAAC 2700
2701 AGTATAAGTTATATTAAAGTGTTTTCACATTTTTTTGAAAGAC 2743
```

FIG. 5D

```
  1  MMQKLQMYVYIYLFMLIAAGPVDLNEGSEREENVEKEGLCNACAWRQNTR   50
     |||||  ||||||||| ||||||| ||  ||||||||||| |||||
  1  MQKLQLCVYIYLFMLIVAGPVDLNENSEQKENVEKEGLCNACTWRQNTK    49

51  YSRIEAIKIQILSKLRLETAPNISKDAIRQLLPRAPPLRELIDQYDVQRD  100
     ||||||||||||||||||||||||| |||||| |||||||||||||||||
 50  SSRIEAIKIQILSKLRLETAPNISKDVIRQLLPKAPPLRELIDQYDVQRD   99

101  DSSDGSLEDDDYHATTETIITMPTESDFLMQADGKPKCCFFKFSSKIQYN  150
     ||||||||||||||||||||||||||||||| ||||||||||||||||||
100  DSSDGSLEDDDYHATTETIITMPTESDFLMQVDGKPKCCFFKFSSKIQYN  149

151  KVVKAQLWIYLRPVKTPTTVFVQILRLIKPMKDGTRYTGIRSLKLDMSPG  200
     |||||||||||||| |||||||||||||||||||||||||||||||| ||
150  KVVKAQLWIYLRPVETPTTVFVQILRLIKPMKDGTRYTGIRSLKLDMNPG  199

201  TGIWQSIDVKTVLQNWLKQPESNLGIEIKALDENGHDLAVTFPGPGEDGL  250
     ||||||||||||||||||||||||||||||||||||||||||||||||||
200  TGIWQSIDVKTVLQNWLKQPESNLGIEIKALDENGHDLAVTFPGPGEDGL  249

251  NPFLEVKVTDTPKRSRRDFGLDCDEHSTESRCCRYPLTVDFEAFGWDWII  300
     ||||||||||||||||||||||||||||||||||||||||||||||||||
250  NPFLEVKVTDTPKRSRRDFGLDCDEHSTESRCCRYPLTVDFEAFGWDWII  299

301  APKRYKANYCSGECEFVFLQKYPHTHLVHQANPRGSAGPCCTPTKMSPIN  350
     ||||||||||||||||||||||||||||||||||||||||||||||||||
300  APKRYKANYCSGECEFVFLQKYPHTHLVHQANPRGSAGPCCTPTKMSPIN  349

351  MLYFNGKEQIIYGKIPAMVVDRCGCS   376
     ||||||||||||||||||||||||||
350  MLYFNGKEQIIYGKIPAMVVDRCGCS   375
```

FIG. 7

SEQUENCE LISTING

```
<160> NUMBER OF SEQ ID NOS: 37

<210> SEQ ID NO 1
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(35)
<223> OTHER INFORMATION: n = A, T, G, or C;   v = A, G, or C, not T;
      r = G or A;  y = T or C;  k = T or G
<220> FEATURE:
<221> NAME/KEY: misc_feature
<222> LOCATION: (1)..(35)
<223> OTHER INFORMATION: 12,27,30,33   n = inosine

<400> SEQUENCE: 1
ccggaattcg gntggvanra ytggrtnrtn kcncc                              35

<210> SEQ ID NO 2
<211> LENGTH: 33
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(33)
<223> OTHER INFORMATION: 13,25,28   n = inosine
<220> FEATURE:
<221> NAME/KEY: misc_feature
<222> LOCATION: (1)..(33)
<223> OTHER INFORMATION: n = A, T, G, or C;   r = A or G;  y = C or T;
      s = G or C

<400> SEQUENCE: 2
ccggaattcr canscrcarc tntcnacnry cat                                33

<210> SEQ ID NO 3
<211> LENGTH: 31
<212> TYPE: DNA
<213> ORGANISM: Artificial Sequence
<220> FEATURE:
<223> OTHER INFORMATION: primer

<400> SEQUENCE: 3
cgcggatcca gagtcaaggt gacagacaca c                                  31
```

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
cgcggatcct cctcatgagc acccacagcg gtc                                    33

<210> SEQ ID NO 5
<211> LENGTH: 550
<212> TYPE: DNA
<213> ORGANISM: Mus musculus
<220> FEATURE:
<221> NAME/KEY: CDS
<222> LOCATION: (59)..(436)
<223> OTHER INFORMATION:

<400> SEQUENCE: 5
ttaaggtagg aaggatttca ggctctattt acataattgt tctttccttt tcacacag         58 aat ccc ttt tta gaa gtc aag gtg aca gac aca ccc aag agg tcc cgg        106
Asn Pro Phe Leu Glu Val Lys Val Thr Asp Thr Pro Lys Arg Ser Arg
1               5                   10                  15 aga gac ttt ggg ctt gac tgc gat gag cac tcc acg gaa tcc cgg tgc        154
Arg Asp Phe Gly Leu Asp Cys Asp Glu His Ser Thr Glu Ser Arg Cys
            20                  25                  30 tgc cgc tac ccc ctc acg gtc gat ttt gaa gcc ttt gga tgg gac tgg        202
Cys Arg Tyr Pro Leu Thr Val Asp Phe Glu Ala Phe Gly Trp Asp Trp
        35                  40                  45 att atc gca ccc aaa aga tat aag gcc aat tac tgc tca gga gag tgt        250
Ile Ile Ala Pro Lys Arg Tyr Lys Ala Asn Tyr Cys Ser Gly Glu Cys
    50                  55                  60 gaa ttt gtg ttt tta caa aaa tat ccg cat act cat ctt gtg cac caa        298
Glu Phe Val Phe Leu Gln Lys Tyr Pro His Thr His Leu Val His Gln
65                  70                  75                  80 gca aac ccc aga ggc tca gca ggc cct tgc tgc act ccg aca aaa atg        346
Ala Asn Pro Arg Gly Ser Ala Gly Pro Cys Cys Thr Pro Thr Lys Met
                85                  90                  95 tct ccc att aat atg cta tat ttt aat ggc aaa gaa caa ata ata tat        394
Ser Pro Ile Asn Met Leu Tyr Phe Asn Gly Lys Glu Gln Ile Ile Tyr
            100                 105                 110 ggg aaa att cca gcc atg gta gta gac cgc tgt ggg tgc tca                436
Gly Lys Ile Pro Ala Met Val Val Asp Arg Cys Gly Cys Ser
        115                 120                 125 tgagctttgc attaggttag aaacttccca agtcatggaa ggtcttcccc tcaatttcga      496
aactgtgaat tcctgcagcc cgggggatcc actagttcta gagcggccgc cacc            550

<210> SEQ ID NO 6
<211> LENGTH: 126
<212> TYPE: PRT
<213> ORGANISM: Mus musculus

<400> SEQUENCE: 6

Asn Pro Phe Leu Glu Val Lys Val Thr Asp Thr Pro Lys Arg Ser Arg
1               5                   10                  15

Arg Asp Phe Gly Leu Asp Cys Asp Glu His Ser Thr Glu Ser Arg Cys
            20                  25                  30

Cys Arg Tyr Pro Leu Thr Val Asp Phe Glu Ala Phe Gly Trp Asp Trp
        35                  40                  45

-continued

```
Ile Ile Ala Pro Lys Arg Tyr Lys Ala Asn Tyr Cys Ser Gly Glu Cys
    50                  55                  60

Glu Phe Val Phe Leu Gln Lys Tyr Pro His Thr His Leu Val His Gln
65                  70                  75                  80

Ala Asn Pro Arg Gly Ser Ala Gly Pro Cys Cys Thr Pro Thr Lys Met
                85                  90                  95

Ser Pro Ile Asn Met Leu Tyr Phe Asn Gly Lys Glu Gln Ile Ile Tyr
            100                 105                 110

Gly Lys Ile Pro Ala Met Val Val Asp Arg Cys Gly Cys Ser
        115                 120                 125

<210> SEQ ID NO 7
<211> LENGTH: 326
<212> TYPE: DNA
<213> ORGANISM: Homo sapiens
<220> FEATURE:
<221> NAME/KEY: CDS
<222> LOCATION: (3)..(326)
<223> OTHER INFORMATION:

<400> SEQUENCE: 7 ca aaa aga tcc aga agg gat ttt ggt ctt gac tgt gat gag cac tca         47
   Lys Arg Ser Arg Arg Asp Phe Gly Leu Asp Cys Asp Glu His Ser
   1               5                   10                  15 aca gaa tca cga tgc tgt cgt tac cct cta act gtg gat ttt gaa gct       95
Thr Glu Ser Arg Cys Cys Arg Tyr Pro Leu Thr Val Asp Phe Glu Ala
                20                  25                  30 ttt gga tgg gat tgg att atc gct cct aaa aga tat aag gcc aat tac      143
Phe Gly Trp Asp Trp Ile Ile Ala Pro Lys Arg Tyr Lys Ala Asn Tyr
            35                  40                  45 tgc tct gga gag tgt gaa ttt gta ttt tta caa aaa tat cct cat act      191
Cys Ser Gly Glu Cys Glu Phe Val Phe Leu Gln Lys Tyr Pro His Thr
        50                  55                  60 cat ctg gta cac caa gca aac ccc aga ggt tca gca ggc cct tgc tgt      239
His Leu Val His Gln Ala Asn Pro Arg Gly Ser Ala Gly Pro Cys Cys
    65                  70                  75 act ccc aca aag atg tct cca att aat atg cta tat ttt aat ggc aaa      287
Thr Pro Thr Lys Met Ser Pro Ile Asn Met Leu Tyr Phe Asn Gly Lys
80                  85                  90                  95 gaa caa ata ata tat ggg aaa att cca gcg atg gta gta                  326
Glu Gln Ile Ile Tyr Gly Lys Ile Pro Ala Met Val Val
                100                 105

<210> SEQ ID NO 8
<211> LENGTH: 108
<212> TYPE: PRT
<213> ORGANISM: Homo sapiens

<400> SEQUENCE: 8

Lys Arg Ser Arg Arg Asp Phe Gly Leu Asp Cys Asp Glu His Ser Thr
1               5                   10                  15

Glu Ser Arg Cys Cys Arg Tyr Pro Leu Thr Val Asp Phe Glu Ala Phe
                20                  25                  30

Gly Trp Asp Trp Ile Ile Ala Pro Lys Arg Tyr Lys Ala Asn Tyr Cys
            35                  40                  45

Ser Gly Glu Cys Glu Phe Val Phe Leu Gln Lys Tyr Pro His Thr His
        50                  55                  60

Leu Val His Gln Ala Asn Pro Arg Gly Ser Ala Gly Pro Cys Cys Thr
65                  70                  75                  80

Pro Thr Lys Met Ser Pro Ile Asn Met Leu Tyr Phe Asn Gly Lys Glu
```

-continued

```
                85                  90                  95
Gln Ile Ile Tyr Gly Lys Ile Pro Ala Met Val Val
            100                 105
```

<210> SEQ ID NO 9
<211> LENGTH: 9
<212> TYPE: PRT
<213> ORGANISM: Artificial Sequence
<220> FEATURE:
<223> OTHER INFORMATION: amino acid encoded by oligonucleotide for PCR
<220> FEATURE:
<221> NAME/KEY: MISC_FEATURE
<222> LOCATION: (3)..(3)
<223> OTHER INFORMATION: Xaa = His, Gln, Asn, Lys, Asp, Glu
<220> FEATURE:
<221> NAME/KEY: MISC_FEATURE
<222> LOCATION: (4)..(4)
<223> OTHER INFORMATION: Xaa = Asp, Asn
<220> FEATURE:
<221> NAME/KEY: MISC_FEATURE
<222> LOCATION: (6)..(7)
<223> OTHER INFORMATION: Xaa = Val, Ile, Met
<220> FEATURE:
<221> NAME/KEY: MISC_FEATURE
<222> LOCATION: (8)..(8)
<223> OTHER INFORMATION: Xaa = Ala, Ser

<400> SEQUENCE: 9

```
Gly Trp Xaa Xaa Trp Xaa Xaa Xaa Pro
1               5
```

<210> SEQ ID NO 10
<211> LENGTH: 8
<212> TYPE: PRT
<213> ORGANISM: Artificial Sequence
<220> FEATURE:
<223> OTHER INFORMATION: amino acid encoded by oligonucleotide for PCR
<220> FEATURE:
<221> NAME/KEY: MISC_FEATURE
<222> LOCATION: (2)..(2)
<223> OTHER INFORMATION: Xaa = Val, Ile, Met, Thr, Ala
<220> FEATURE:
<221> NAME/KEY: MISC_FEATURE
<222> LOCATION: (4)..(4)
<223> OTHER INFORMATION: Xaa = Asp, Glu
<220> FEATURE:
<221> NAME/KEY: MISC_FEATURE
<222> LOCATION: (7)..(7)
<223> OTHER INFORMATION: Xaa = Gly, Ala

<400> SEQUENCE: 10

```
Met Xaa Val Xaa Ser Cys Xaa Cys
1               5
```

<210> SEQ ID NO 11
<211> LENGTH: 2676
<212> TYPE: DNA
<213> ORGANISM: Mus musculus
<220> FEATURE:
<221> NAME/KEY: CDS
<222> LOCATION: (104)..(1231)
<223> OTHER INFORMATION:

<400> SEQUENCE: 11

```
gtctctcgga cggtacatgc actaatattt cacttggcat tactcaaaag caaaagaag      60 aaataagaac aagggaaaaa aaagattgt gctgattttt aaa atg atg caa aaa      115
                                              Met Met Gln Lys
                                                1 ctg caa atg tat gtt tat att tac ctg ttc atg ctg att gct gct ggc      163
Leu Gln Met Tyr Val Tyr Ile Tyr Leu Phe Met Leu Ile Ala Ala Gly
```

-continued

| | 5 | | | 10 | | | 15 | | | 20 | | |
|---|---|---|---|---|---|---|---|---|---|---|---|---|
| cca | gtg | gat | cta | aat | gag | ggc | agt | gag | aga | gaa | gaa | aat | gtg | gaa | aaa | 211 |
| Pro | Val | Asp | Leu | Asn | Glu | Gly | Ser | Glu | Arg | Glu | Glu | Asn | Val | Glu | Lys | |
| | | | | 25 | | | | 30 | | | | 35 | | | | |
| gag | ggg | ctg | tgt | aat | gca | tgt | gcg | tgg | aga | caa | aac | acg | agg | tac | tcc | 259 |
| Glu | Gly | Leu | Cys | Asn | Ala | Cys | Ala | Trp | Arg | Gln | Asn | Thr | Arg | Tyr | Ser | |
| | | | | 40 | | | | 45 | | | | 50 | | | | |
| aga | ata | gaa | gcc | ata | aaa | att | caa | atc | ctc | agt | aag | ctg | cgc | ctg | gaa | 307 |
| Arg | Ile | Glu | Ala | Ile | Lys | Ile | Gln | Ile | Leu | Ser | Lys | Leu | Arg | Leu | Glu | |
| | | | | 55 | | | | 60 | | | | 65 | | | | |
| aca | gct | cct | aac | atc | agc | aaa | gat | gct | ata | aga | caa | ctt | ctg | cca | aga | 355 |
| Thr | Ala | Pro | Asn | Ile | Ser | Lys | Asp | Ala | Ile | Arg | Gln | Leu | Leu | Pro | Arg | |
| | 70 | | | | 75 | | | | 80 | | | | | | | |
| gcg | cct | cca | ctc | cgg | gaa | ctg | atc | gat | cag | tac | gac | gtc | cag | agg | gat | 403 |
| Ala | Pro | Pro | Leu | Arg | Glu | Leu | Ile | Asp | Gln | Tyr | Asp | Val | Gln | Arg | Asp | |
| 85 | | | | | 90 | | | | 95 | | | | 100 | | | |
| gac | agc | agt | gat | ggc | tct | ttg | gaa | gat | gac | gat | tat | cac | gct | acc | acg | 451 |
| Asp | Ser | Ser | Asp | Gly | Ser | Leu | Glu | Asp | Asp | Asp | Tyr | His | Ala | Thr | Thr | |
| | | | | 105 | | | | 110 | | | | 115 | | | | |
| gaa | aca | atc | att | acc | atg | cct | aca | gag | tct | gac | ttt | cta | atg | caa | gcg | 499 |
| Glu | Thr | Ile | Ile | Thr | Met | Pro | Thr | Glu | Ser | Asp | Phe | Leu | Met | Gln | Ala | |
| | | | 120 | | | | 125 | | | | 130 | | | | | |
| gat | ggc | aag | ccc | aaa | tgt | tgc | ttt | ttt | aaa | ttt | agc | tct | aaa | ata | cag | 547 |
| Asp | Gly | Lys | Pro | Lys | Cys | Cys | Phe | Phe | Lys | Phe | Ser | Ser | Lys | Ile | Gln | |
| | | 135 | | | | 140 | | | | 145 | | | | | | |
| tac | aac | aaa | gta | gta | aaa | gcc | caa | ctg | tgg | ata | tat | ctc | aga | ccc | gtc | 595 |
| Tyr | Asn | Lys | Val | Val | Lys | Ala | Gln | Leu | Trp | Ile | Tyr | Leu | Arg | Pro | Val | |
| | 150 | | | | 155 | | | | 160 | | | | | | | |
| aag | act | cct | aca | aca | gtg | ttt | gtg | caa | atc | ctg | aga | ctc | atc | aaa | ccc | 643 |
| Lys | Thr | Pro | Thr | Thr | Val | Phe | Val | Gln | Ile | Leu | Arg | Leu | Ile | Lys | Pro | |
| 165 | | | | | 170 | | | | 175 | | | | 180 | | | |
| atg | aaa | gac | ggt | aca | agg | tat | act | gga | atc | cga | tct | ctg | aaa | ctt | gac | 691 |
| Met | Lys | Asp | Gly | Thr | Arg | Tyr | Thr | Gly | Ile | Arg | Ser | Leu | Lys | Leu | Asp | |
| | | | | 185 | | | | 190 | | | | 195 | | | | |
| atg | agc | cca | ggc | act | ggt | att | tgg | cag | agt | att | gat | gtg | aag | aca | gtg | 739 |
| Met | Ser | Pro | Gly | Thr | Gly | Ile | Trp | Gln | Ser | Ile | Asp | Val | Lys | Thr | Val | |
| | | | 200 | | | | 205 | | | | 210 | | | | | |
| ttg | caa | aat | tgg | ctc | aaa | cag | cct | gaa | tcc | aac | tta | ggc | att | gaa | atc | 787 |
| Leu | Gln | Asn | Trp | Leu | Lys | Gln | Pro | Glu | Ser | Asn | Leu | Gly | Ile | Glu | Ile | |
| | | 215 | | | | 220 | | | | 225 | | | | | | |
| aaa | gct | ttg | gat | gag | aat | ggc | cat | gat | ctt | gct | gta | acc | ttc | cca | gga | 835 |
| Lys | Ala | Leu | Asp | Glu | Asn | Gly | His | Asp | Leu | Ala | Val | Thr | Phe | Pro | Gly | |
| | 230 | | | | 235 | | | | 240 | | | | | | | |
| cca | gga | gaa | gat | ggg | ctg | aat | ccc | ttt | tta | gaa | gtc | aag | gtg | aca | gac | 883 |
| Pro | Gly | Glu | Asp | Gly | Leu | Asn | Pro | Phe | Leu | Glu | Val | Lys | Val | Thr | Asp | |
| 245 | | | | | 250 | | | | 255 | | | | 260 | | | |
| aca | ccc | aag | agg | tcc | cgg | aga | gac | ttt | ggg | ctt | gac | tgc | gat | gag | cac | 931 |
| Thr | Pro | Lys | Arg | Ser | Arg | Arg | Asp | Phe | Gly | Leu | Asp | Cys | Asp | Glu | His | |
| | | | | 265 | | | | 270 | | | | 275 | | | | |
| tcc | acg | gaa | tcc | cgg | tgc | tgc | cgc | tac | ccc | ctc | acg | gtc | gat | ttt | gaa | 979 |
| Ser | Thr | Glu | Ser | Arg | Cys | Cys | Arg | Tyr | Pro | Leu | Thr | Val | Asp | Phe | Glu | |
| | | | 280 | | | | 285 | | | | 290 | | | | | |
| gcc | ttt | gga | tgg | gac | tgg | att | atc | gca | ccc | aaa | aga | tat | aag | gcc | aat | 1027 |
| Ala | Phe | Gly | Trp | Asp | Trp | Ile | Ile | Ala | Pro | Lys | Arg | Tyr | Lys | Ala | Asn | |
| | | | 295 | | | | 300 | | | | 305 | | | | | |
| tac | tgc | tca | gga | gag | tgt | gaa | ttt | gtg | ttt | tta | caa | aaa | tat | ccg | cat | 1075 |
| Tyr | Cys | Ser | Gly | Glu | Cys | Glu | Phe | Val | Phe | Leu | Gln | Lys | Tyr | Pro | His | |
| | | | 310 | | | | 315 | | | | 320 | | | | | |
| act | cat | ctt | gtg | cac | caa | gca | aac | ccc | aga | ggc | tca | gca | ggc | cct | tgc | 1123 |

```
Thr His Leu Val His Gln Ala Asn Pro Arg Gly Ser Ala Gly Pro Cys
325                 330                 335                 340 tgc act ccg aca aaa atg tct ccc att aat atg cta tat ttt aat ggc    1171
Cys Thr Pro Thr Lys Met Ser Pro Ile Asn Met Leu Tyr Phe Asn Gly
                345                 350                 355 aaa gaa caa ata ata tat ggg aaa att cca gcc atg gta gta gac cgc    1219
Lys Glu Gln Ile Ile Tyr Gly Lys Ile Pro Ala Met Val Val Asp Arg
            360                 365                 370 tgt ggg tgc tca tgagctttgc attaggttag aaacttccca agtcatggaa        1271
Cys Gly Cys Ser
            375 ggtcttcccc tcaatttcga aactgtgaat tcaagcacca caggctgtag gccttgagta  1331 tgctctagta acgtaagcac aagctacagt gtatgaacta aaagagagaa tagatgcaat  1391 ggttggcatt caaccaccaa ataaaccat  actataggat gttgtatgat ttccagagtt  1451 tttgaaatag atggagatca aattacattt atgtccatat atgtatatta caactacaat  1511 ctaggcaagg aagtgagagc acatcttgtg gtctgctgag ttaggagggt atgattaaaa  1571 ggtaaagtct tatttcctaa cagtttcact taatatttac agaagaatct atatgtagcc  1631 tttgtaaagt gtaggattgt tatcatttaa aaacatcatg tacacttata tttgtattgt  1691 atacttggta agataaaatt ccacaaagta ggaatggggc ctcacataca cattgccatt  1751 cctattataa ttggacaatc caccacggtg ctaatgcagt gctgaatggc tcctactgga  1811 cctctcgata gaacactcta caaagtacga gtctctctct cccttccagg tgcatctcca  1871 cacacacagc actaagtgtt caatgcattt tctttaagga agaagaatc  tttttttcta  1931 gaggtcaact ttcagtcaac tctagcacag cgggagtgac tgctgcatct taaaaggcag  1991 ccaaacagta ttcattttt aatctaaatt tcaaaatcac tgtctgcctt tatcacatgg   2051 caattttgtg gtaaaataat ggaaatgact ggttctatca atattgtata aaagactctg  2111 aaacaattac atttatataa tatgtataca atattgtttt gtaaataagt gtctcctttt  2171 atatttactt tggtatattt ttacactaat gaaatttcaa atcattaaag tacaaagaca  2231 tgtcatgtat cacaaaaaag gtgactgctt ctatttcaga gtgaattagc agattcaata  2291 gtggtcttaa aactctgtat gttaagatta gaaggttata ttacaatcaa tttatgtatt  2351 ttttacatta tcaacttatg gtttcatggt ggctgtatct atgaatgtgg ctcccagtca  2411 aatttcaatg ccccaccatt ttaaaaatta caagcattac taaacatacc aacatgtatc  2471 taaagaaata caaatatggt atctcaataa cagctacttt tttatttat  aatttgacaa   2531 tgaatacatt tctttattt  acttcagttt tataaattgg aactttgttt atcaaatgta  2591 ttgtactcat agctaaatga aattatttct tacataaaaa tgtgtagaaa ctataaatta  2651 aagtgttttc acatttttga aaggc                                         2676
```

<210> SEQ ID NO 12
<211> LENGTH: 376
<212> TYPE: PRT
<213> ORGANISM: Mus musculus

<400> SEQUENCE: 12

```
Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
        35                  40                  45
```

```
Thr Arg Tyr Ser Arg Ile Glu Ala Ile Lys Ile Gln Ile Leu Ser Lys
 50                  55                  60

Leu Arg Leu Glu Thr Ala Pro Asn Ile Ser Lys Asp Ala Ile Arg Gln
 65                  70                  75                  80

Leu Leu Pro Arg Ala Pro Pro Leu Arg Glu Leu Ile Asp Gln Tyr Asp
                 85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
        195                 200                 205

Val Lys Thr Val Leu Gln Asn Trp Leu Lys Gln Pro Glu Ser Asn Leu
210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
                245                 250                 255

Lys Val Thr Asp Thr Pro Lys Arg Ser Arg Arg Asp Phe Gly Leu Asp
            260                 265                 270

Cys Asp Glu His Ser Thr Glu Ser Arg Cys Cys Arg Tyr Pro Leu Thr
        275                 280                 285

Val Asp Phe Glu Ala Phe Gly Trp Asp Trp Ile Ile Ala Pro Lys Arg
290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
        355                 360                 365

Val Val Asp Arg Cys Gly Cys Ser
370                 375

<210> SEQ ID NO 13
<211> LENGTH: 2743
<212> TYPE: DNA
<213> ORGANISM: Homo sapiens
<220> FEATURE:
<221> NAME/KEY: CDS
<222> LOCATION: (59)..(1183)
<223> OTHER INFORMATION:

<400> SEQUENCE: 13 aagaaagta aaaggaagaa acaagaacaa gaaaaaagat tatattgatt ttaaaatc      58 atg caa aaa ctg caa ctc tgt gtt tat att tac ctg ttt atg ctg att    106
```

```
Met Gln Lys Leu Gln Leu Cys Val Tyr Ile Tyr Leu Phe Met Leu Ile
1               5                   10                  15 gtt gct ggt cca gtg gat cta aat gag aac agt gag caa aaa gaa aat        154
Val Ala Gly Pro Val Asp Leu Asn Glu Asn Ser Glu Gln Lys Glu Asn
            20                  25                  30 gtg gaa aaa gag ggg ctg tgt aat gca tgt act tgg aga caa aac act        202
Val Glu Lys Glu Gly Leu Cys Asn Ala Cys Thr Trp Arg Gln Asn Thr
        35                  40                  45 aaa tct tca aga ata gaa gcc att aag ata caa atc ctc agt aaa ctt        250
Lys Ser Ser Arg Ile Glu Ala Ile Lys Ile Gln Ile Leu Ser Lys Leu
    50                  55                  60 cgt ctg gaa aca gct cct aac atc agc aaa gat gtt ata aga caa ctt        298
Arg Leu Glu Thr Ala Pro Asn Ile Ser Lys Asp Val Ile Arg Gln Leu
65                  70                  75                  80 tta ccc aaa gct cct cca ctc cgg gaa ctg att gat cag tat gat gtc        346
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac        394
Gln Arg Asp Asp Ser Ser Asp Gly Ser Leu Glu Asp Asp Asp Tyr His
            100                 105                 110 gct aca acg gaa aca atc att acc atg cct aca gag tct gat ttt cta        442
Ala Thr Thr Glu Thr Ile Ile Thr Met Pro Thr Glu Ser Asp Phe Leu
        115                 120                 125 atg caa gtg gat gga aaa ccc aaa tgt tgc ttc ttt aaa ttt agc tct        490
Met Gln Val Asp Gly Lys Pro Lys Cys Cys Phe Phe Lys Phe Ser Ser
130                 135                 140 aaa ata caa tac aat aaa gta gta aag gcc caa cta tgg ata tat ttg        538
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc        586
Arg Pro Val Glu Thr Pro Thr Thr Val Phe Val Gln Ile Leu Arg Leu
                165                 170                 175 atc aaa cct atg aaa gac ggt aca agg tat act gga atc cga tct ctg        634
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg        682
Lys Leu Asp Met Asn Pro Gly Thr Gly Ile Trp Gln Ser Ile Asp Val
        195                 200                 205 aag aca gtg ttg caa aat tgg ctc aaa caa cct gaa tcc aac tta ggc        730
Lys Thr Val Leu Gln Asn Trp Leu Lys Gln Pro Glu Ser Asn Leu Gly
210                 215                 220 att gaa ata aaa gct tta gat gag aat ggt cat gat ctt gct gta acc        778
Ile Glu Ile Lys Ala Leu Asp Glu Asn Gly His Asp Leu Ala Val Thr
225                 230                 235                 240 ttc cca gga cca gga gaa gat ggg ctg aat ccg ttt tta gag gtc aag        826
Phe Pro Gly Pro Gly Glu Asp Gly Leu Asn Pro Phe Leu Glu Val Lys
                245                 250                 255 gta aca gac aca cca aaa aga tcc aga agg gat ttt ggt ctt gac tgt        874
Val Thr Asp Thr Pro Lys Arg Ser Arg Arg Asp Phe Gly Leu Asp Cys
            260                 265                 270 gat gag cac tca aca gaa tca cga tgc tgt cgt tac cct cta act gtg        922
Asp Glu His Ser Thr Glu Ser Arg Cys Cys Arg Tyr Pro Leu Thr Val
        275                 280                 285 gat ttt gaa gct ttt gga tgg gat tgg att atc gct cct aaa aga tat        970
Asp Phe Glu Ala Phe Gly Trp Asp Trp Ile Ile Ala Pro Lys Arg Tyr
290                 295                 300 aag gcc aat tac tgc tct gga gag tgt gaa ttt gta ttt tta caa aaa       1018
Lys Ala Asn Tyr Cys Ser Gly Glu Cys Glu Phe Val Phe Leu Gln Lys
305                 310                 315                 320
```

-continued

| | | |
|---|---|---|
| tat cct cat act cat ctg gta cac caa gca aac ccc aga ggt tca gca<br>Tyr Pro His Thr His Leu Val His Gln Ala Asn Pro Arg Gly Ser Ala<br>                                  325                          330                         335 | 1066 |

```
tat cct cat act cat ctg gta cac caa gca aac ccc aga ggt tca gca    1066
Tyr Pro His Thr His Leu Val His Gln Ala Asn Pro Arg Gly Ser Ala
            325                 330                 335 ggc cct tgc tgt act ccc aca aag atg tct cca att aat atg cta tat    1114
Gly Pro Cys Cys Thr Pro Thr Lys Met Ser Pro Ile Asn Met Leu Tyr
        340                 345                 350 ttt aat ggc aaa gaa caa ata ata tat ggg aaa att cca gcg atg gta    1162
Phe Asn Gly Lys Glu Gln Ile Ile Tyr Gly Lys Ile Pro Ala Met Val
    355                 360                 365 gta gac cgc tgt ggg tgc tca tgagatttat attaagcgtt cataacttcc        1213
Val Asp Arg Cys Gly Cys Ser
    370             375 taaaacatgg aaggttttcc cctcaacaat tttgaagctg tgaaattaag taccacaggc    1273
tataggccta gagtatgcta cagtcactta agcataagct acagtatgta aactaaaagg    1333
gggaatatat gcaatggttg gcatttaacc atccaaacaa atcatacaag aaagttttat    1393
gatttccaga gttttgagc tagaaggaga tcaaattaca tttatgttcc tatatattac      1453
aacatcggcg aggaaatgaa agcgattctc cttgagttct gatgaattaa aggagtatgc    1513
tttaaagtct atttctttaa agttttgttt aatatttaca gaaaaatcca catacagtat    1573
tggtaaaatg caggattgtt ataccatc attcgaatca tccttaaaca cttgaattta      1633
tattgtatgg tagtatactt ggtaagataa aattccacaa aaatagggat ggtgcagcat    1693
atgcaatttc cattcctatt ataattgaca cagtacatta acaatccatg ccaacggtgc    1753
taatacgata ggctgaatgt ctgaggctac caggtttatc acataaaaaa cattcagtaa    1813
aatagtaagt ttctcttttc ttcaggtgca ttttcctaca cctccaaatg aggaatggat    1873
tttctttaat gtaagaagaa tcattttct agaggttggc tttcaattct gtagcatact     1933
tggagaaact gcattatctt aaaaggcagt caaatggtgt tgtttttat caaaatgtca     1993
aaataacata cttggagaag tatgtaattt tgtctttgga aaattacaac actgcctttg    2053
caacactgca gttttatgg taaaataata gaaatgatcg actctatcaa tattgtataa     2113
aaagactgaa acaatgcatt tatataatat gtatacaata ttgttttgta ataagtgtc     2173
tcctttttta tttactttgg tatattttta cactaaggac atttcaaatt aagtactaag    2233
gcacaaagac atgtcatgca tcacagaaaa gcaactactt atatttcaga gcaaattagc    2293
agattaaata gtggtcttaa aactccatat gttaatgatt agatggttat attacaatca    2353
ttttatattt ttttcatga ttaacattca cttatggatt catgatggct gtataaagtg     2413
aatttgaaat ttcaatggtt tactgtcatt gtgtttaaat ctcaacgttc cattatttta    2473
atacttgcaa aaacattact aagtatacca aaataattga ctctattatc tgaaatgaag    2533
aataaactga tgctatctca acaataactg ttacttttat tttataattt gataatgaat    2593
atatttctgc atttatttac ttctgttttg taaattggga ttttgttaat caaatttatt    2653
gtactatgac taaatgaaat tatttcttac atctaatttg tagaaacagt ataagttata    2713
ttaaagtgtt ttcacatttt tttgaaagac                                     2743
```

<210> SEQ ID NO 14
<211> LENGTH: 375
<212> TYPE: PRT
<213> ORGANISM: Homo sapiens

<400> SEQUENCE: 14

Met Gln Lys Leu Gln Leu Cys Val Tyr Ile Tyr Leu Phe Met Leu Ile
1                 5                    10                   15

```
Val Ala Gly Pro Val Asp Leu Asn Glu Asn Ser Glu Gln Lys Glu Asn
            20                  25                  30
Val Glu Lys Glu Gly Leu Cys Asn Ala Cys Thr Trp Arg Gln Asn Thr
        35                  40                  45
Lys Ser Ser Arg Ile Glu Ala Ile Lys Ile Gln Ile Leu Ser Lys Leu
50                  55                  60
Arg Leu Glu Thr Ala Pro Asn Ile Ser Lys Asp Val Ile Arg Gln Leu
65                  70                  75                  80
Leu Pro Lys Ala Pro Pro Leu Arg Glu Leu Ile Asp Gln Tyr Asp Val
                85                  90                  95
Gln Arg Asp Asp Ser Ser Asp Gly Ser Leu Glu Asp Asp Asp Tyr His
            100                 105                 110
Ala Thr Thr Glu Thr Ile Ile Thr Met Pro Thr Glu Ser Asp Phe Leu
        115                 120                 125
Met Gln Val Asp Gly Lys Pro Lys Cys Cys Phe Phe Lys Phe Ser Ser
130                 135                 140
Lys Ile Gln Tyr Asn Lys Val Val Lys Ala Gln Leu Trp Ile Tyr Leu
145                 150                 155                 160
Arg Pro Val Glu Thr Pro Thr Thr Val Phe Val Gln Ile Leu Arg Leu
                165                 170                 175
Ile Lys Pro Met Lys Asp Gly Thr Arg Tyr Thr Gly Ile Arg Ser Leu
            180                 185                 190
Lys Leu Asp Met Asn Pro Gly Thr Gly Ile Trp Gln Ser Ile Asp Val
        195                 200                 205
Lys Thr Val Leu Gln Asn Trp Leu Lys Gln Pro Glu Ser Asn Leu Gly
210                 215                 220
Ile Glu Ile Lys Ala Leu Asp Glu Asn Gly His Asp Leu Ala Val Thr
225                 230                 235                 240
Phe Pro Gly Pro Gly Glu Asp Gly Leu Asn Pro Phe Leu Glu Val Lys
                245                 250                 255
Val Thr Asp Thr Pro Lys Arg Ser Arg Arg Asp Phe Gly Leu Asp Cys
            260                 265                 270
Asp Glu His Ser Thr Glu Ser Arg Cys Cys Arg Tyr Pro Leu Thr Val
        275                 280                 285
Asp Phe Glu Ala Phe Gly Trp Asp Trp Ile Ile Ala Pro Lys Arg Tyr
290                 295                 300
Lys Ala Asn Tyr Cys Ser Gly Glu Cys Glu Phe Val Phe Leu Gln Lys
305                 310                 315                 320
Tyr Pro His Thr His Leu Val His Gln Ala Asn Pro Arg Gly Ser Ala
                325                 330                 335
Gly Pro Cys Cys Thr Pro Thr Lys Met Ser Pro Ile Asn Met Leu Tyr
            340                 345                 350
Phe Asn Gly Lys Glu Gln Ile Ile Tyr Gly Lys Ile Pro Ala Met Val
        355                 360                 365
Val Asp Arg Cys Gly Cys Ser
370                 375

<210> SEQ ID NO 15
<211> LENGTH: 34
<212> TYPE: DNA
<213> ORGANISM: Artificial Sequence
<220> FEATURE:
<223> OTHER INFORMATION: oligonucleotide for PCR

<400> SEQUENCE: 15
```

```
cgcggatccg tggatctaaa tgagaacagt gagc                                34
```

<210> SEQ ID NO 16
<211> LENGTH: 37
<212> TYPE: DNA
<213> ORGANISM: Artificial Sequence
<220> FEATURE:
<223> OTHER INFORMATION: oligonucleotide for PCR

<400> SEQUENCE: 16

```
cgcgaattct caggtaatga ttgtttccgt tgtagcg                             37
```

<210> SEQ ID NO 17
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 17

```
acactaaatc ttcaagaata                                                20
```

<210> SEQ ID NO 18
<211> LENGTH: 480
<212> TYPE: DNA
<213> ORGANISM: Rattus norvegicus
<220> FEATURE:
<221> NAME/KEY: CDS
<222> LOCATION: (1)..(390)
<223> OTHER INFORMATION:

<400> SEQUENCE: 18

```
gaa gat ggg ctg aat ccc ttt tta gaa gtc aaa gta aca gac aca ccc      48
Glu Asp Gly Leu Asn Pro Phe Leu Glu Val Lys Val Thr Asp Thr Pro
1               5                   10                  15 aag agg tcc cgg aga gac ttt ggg ctt gac tgc gat gaa cac tcc acg      96
Lys Arg Ser Arg Arg Asp Phe Gly Leu Asp Cys Asp Glu His Ser Thr
            20                  25                  30 gaa tcg cgg tgc tgt cgc tac ccc ctc acg gtc gat ttc gaa gcc ttt     144
Glu Ser Arg Cys Cys Arg Tyr Pro Leu Thr Val Asp Phe Glu Ala Phe
        35                  40                  45 gga tgg gac tgg att att gca ccc aaa aga tat aag gct aat tac tgc     192
Gly Trp Asp Trp Ile Ile Ala Pro Lys Arg Tyr Lys Ala Asn Tyr Cys
    50                  55                  60 tct gga gag tgt gaa ttt gtg ttc tta caa aaa tat ccg cat act cat     240
Ser Gly Glu Cys Glu Phe Val Phe Leu Gln Lys Tyr Pro His Thr His
65                  70                  75                  80 ctt gtg cac caa gca aac ccc aga ggc tcg gca ggc cct tgc tgc acg     288
Leu Val His Gln Ala Asn Pro Arg Gly Ser Ala Gly Pro Cys Cys Thr
                85                  90                  95 cca aca aaa atg tct ccc att aat atg cta tat ttt aat ggc aaa gaa     336
Pro Thr Lys Met Ser Pro Ile Asn Met Leu Tyr Phe Asn Gly Lys Glu
            100                 105                 110 caa ata ata tat ggg aaa att cca gcc atg gta gta gac cgg tgt ggg     384
Gln Ile Ile Tyr Gly Lys Ile Pro Ala Met Val Val Asp Arg Cys Gly
        115                 120                 125 tgc tcg tgagctttgc attagcttta aaatttccca atcgtggaa ggtcttcccc       440
Cys Ser
    130 tcgatttcga aactgtgaat ttatgtacca caggctgtag                         480
```

<210> SEQ ID NO 19
<211> LENGTH: 130

```
<212> TYPE: PRT
<213> ORGANISM: Rattus norvegicus

<400> SEQUENCE: 19

Glu Asp Gly Leu Asn Pro Phe Leu Glu Val Lys Val Thr Asp Thr Pro
1               5                   10                  15

Lys Arg Ser Arg Arg Asp Phe Gly Leu Asp Cys Asp Glu His Ser Thr
            20                  25                  30

Glu Ser Arg Cys Cys Arg Tyr Pro Leu Thr Val Asp Phe Glu Ala Phe
        35                  40                  45

Gly Trp Asp Trp Ile Ile Ala Pro Lys Arg Tyr Lys Ala Asn Tyr Cys
    50                  55                  60

Ser Gly Glu Cys Glu Phe Val Phe Leu Gln Lys Tyr Pro His Thr His
65                  70                  75                  80

Leu Val His Gln Ala Asn Pro Arg Gly Ser Ala Gly Pro Cys Cys Thr
                85                  90                  95

Pro Thr Lys Met Ser Pro Ile Asn Met Leu Tyr Phe Asn Gly Lys Glu
            100                 105                 110

Gln Ile Ile Tyr Gly Lys Ile Pro Ala Met Val Val Asp Arg Cys Gly
                115                 120                 125

Cys Ser
    130

<210> SEQ ID NO 20
<211> LENGTH: 790
<212> TYPE: DNA
<213> ORGANISM: Gallus gallus
<220> FEATURE:
<221> NAME/KEY: CDS
<222> LOCATION: (1)..(678)
<223> OTHER INFORMATION:

<400> SEQUENCE: 20 tta gta gta aag gca caa tta tgg ata tac ttg agg caa gtc caa aaa      48
Leu Val Val Lys Ala Gln Leu Trp Ile Tyr Leu Arg Gln Val Gln Lys
1               5                   10                  15 cct aca acg gtg ttt gtg cag atc ctg aga ctc att aag ccc atg aaa      96
Pro Thr Thr Val Phe Val Gln Ile Leu Arg Leu Ile Lys Pro Met Lys
            20                  25                  30 gac ggt aca aga tat act gga att cga tct ttg aaa ctt gac atg aac     144
Asp Gly Thr Arg Tyr Thr Gly Ile Arg Ser Leu Lys Leu Asp Met Asn
        35                  40                  45 cca ggc act ggt atc tgg cag agt att gat gtg aag aca gtg ctg caa     192
Pro Gly Thr Gly Ile Trp Gln Ser Ile Asp Val Lys Thr Val Leu Gln
    50                  55                  60 aat tgg ctc aaa cag cct gaa tcc aat tta ggc atc gaa ata aaa gct     240
Asn Trp Leu Lys Gln Pro Glu Ser Asn Leu Gly Ile Glu Ile Lys Ala
65                  70                  75                  80 ttt gat gag act gga cga gat ctt gct gtc aca ttc cca gga cca gga     288
Phe Asp Glu Thr Gly Arg Asp Leu Ala Val Thr Phe Pro Gly Pro Gly
                85                  90                  95 gaa gat gga ttg aac cca ttt tta gag gtc aga gtt aca gac aca ccg     336
Glu Asp Gly Leu Asn Pro Phe Leu Glu Val Arg Val Thr Asp Thr Pro
            100                 105                 110 aaa cgg tcc cgc aga gat ttt ggc ctt gac tgt gat gag cac tca acg     384
Lys Arg Ser Arg Arg Asp Phe Gly Leu Asp Cys Asp Glu His Ser Thr
        115                 120                 125 gaa tcc cga tgt tgt cgc tac ccg ctg aca gtg gat ttc gaa gct ttt     432
Glu Ser Arg Cys Cys Arg Tyr Pro Leu Thr Val Asp Phe Glu Ala Phe
    130                 135                 140
```

```
gga tgg gac tgg att ata gca cct aaa aga tac aaa gcc aat tac tgc     480
Gly Trp Asp Trp Ile Ile Ala Pro Lys Arg Tyr Lys Ala Asn Tyr Cys
145                 150                 155                 160 tcc gga gaa tgc gaa ttt gtg ttt cta cag aaa tac ccg cac act cac     528
Ser Gly Glu Cys Glu Phe Val Phe Leu Gln Lys Tyr Pro His Thr His
                165                 170                 175 ctg gta cac caa gca aat ccc aga ggc tca gca ggc cct tgc tgc aca     576
Leu Val His Gln Ala Asn Pro Arg Gly Ser Ala Gly Pro Cys Cys Thr
            180                 185                 190 ccc acc aag atg tcc cct ata aac atg ctg tat ttc aat gga aaa gaa     624
Pro Thr Lys Met Ser Pro Ile Asn Met Leu Tyr Phe Asn Gly Lys Glu
        195                 200                 205 caa ata ata tat gga aag ata cca gcc atg gtt gta gat cgt tgc ggg     672
Gln Ile Ile Tyr Gly Lys Ile Pro Ala Met Val Val Asp Arg Cys Gly
    210                 215                 220 tgc tca tgaggctgtc gtgagatcca ccattcgata aattgtggaa gccaccaaaa     728
Cys Ser
225 aaaaaagcta tcccctca tccatctttg aaactgtgaa attacgtacg ctaggcattg     788 cc                                                                  790

<210> SEQ ID NO 21
<211> LENGTH: 226
<212> TYPE: PRT
<213> ORGANISM: Gallus gallus

<400> SEQUENCE: 21

Leu Val Val Lys Ala Gln Leu Trp Ile Tyr Leu Arg Gln Val Gln Lys
1               5                   10                  15

Pro Thr Thr Val Phe Val Gln Ile Leu Arg Leu Ile Lys Pro Met Lys
            20                  25                  30

Asp Gly Thr Arg Tyr Thr Gly Ile Arg Ser Leu Lys Leu Asp Met Asn
        35                  40                  45

Pro Gly Thr Gly Ile Trp Gln Ser Ile Asp Val Lys Thr Val Leu Gln
    50                  55                  60

Asn Trp Leu Lys Gln Pro Glu Ser Asn Leu Gly Ile Glu Ile Lys Ala
65                  70                  75                  80

Phe Asp Glu Thr Gly Arg Asp Leu Ala Val Thr Phe Pro Gly Pro Gly
                85                  90                  95

Glu Asp Gly Leu Asn Pro Phe Leu Glu Val Arg Val Thr Asp Thr Pro
            100                 105                 110

Lys Arg Ser Arg Arg Asp Phe Gly Leu Asp Cys Asp Glu His Ser Thr
        115                 120                 125

Glu Ser Arg Cys Cys Arg Tyr Pro Leu Thr Val Asp Phe Glu Ala Phe
    130                 135                 140

Gly Trp Asp Trp Ile Ile Ala Pro Lys Arg Tyr Lys Ala Asn Tyr Cys
145                 150                 155                 160

Ser Gly Glu Cys Glu Phe Val Phe Leu Gln Lys Tyr Pro His Thr His
                165                 170                 175

Leu Val His Gln Ala Asn Pro Arg Gly Ser Ala Gly Pro Cys Cys Thr
            180                 185                 190

Pro Thr Lys Met Ser Pro Ile Asn Met Leu Tyr Phe Asn Gly Lys Glu
        195                 200                 205

Gln Ile Ile Tyr Gly Lys Ile Pro Ala Met Val Val Asp Arg Cys Gly
    210                 215                 220
```

```
Cys Ser
225

<210> SEQ ID NO 22
<211> LENGTH: 123
<212> TYPE: PRT
<213> ORGANISM: Homo sapiens

<400> SEQUENCE: 22

Arg Pro Arg Arg Asp Ala Glu Pro Val Leu Gly Gly Pro Gly Gly
1               5                   10                  15

Ala Cys Arg Ala Arg Leu Tyr Val Ser Phe Arg Glu Val Gly Trp
            20                  25                  30

His Arg Trp Val Ile Ala Pro Arg Gly Phe Leu Ala Asn Tyr Cys Gln
        35                  40                  45

Gly Gln Cys Ala Leu Pro Val Ala Leu Ser Gly Ser Gly Gly Pro Pro
    50                  55                  60

Ala Leu Asn His Ala Val Leu Arg Ala Leu Met His Ala Ala Ala Pro
65                  70                  75                  80

Gly Ala Ala Asp Leu Pro Cys Cys Val Pro Ala Arg Leu Ser Pro Ile
                85                  90                  95

Ser Val Leu Phe Phe Asp Asn Ser Asp Asn Val Val Leu Arg Gln Tyr
            100                 105                 110

Glu Asp Met Val Val Asp Glu Cys Gly Cys Arg
        115                 120

<210> SEQ ID NO 23
<211> LENGTH: 118
<212> TYPE: PRT
<213> ORGANISM: Homo sapiens

<400> SEQUENCE: 23

Arg Glu Lys Arg Gln Ala Lys His Lys Gln Arg Lys Arg Leu Lys Ser
1               5                   10                  15

Ser Cys Lys Arg His Pro Leu Tyr Val Asp Phe Ser Asp Val Gly Trp
            20                  25                  30

Asn Asp Trp Ile Val Ala Pro Pro Gly Tyr His Ala Phe Tyr Cys His
        35                  40                  45

Gly Glu Cys Pro Phe Pro Leu Ala Asp His Leu Asn Ser Thr Asn His
    50                  55                  60

Ala Ile Val Gln Thr Leu Val Asn Ser Val Asn Ser Lys Ile Pro Lys
65                  70                  75                  80

Ala Cys Cys Val Pro Thr Glu Leu Ser Ala Ile Ser Met Leu Tyr Leu
                85                  90                  95

Asp Glu Asn Glu Lys Val Val Leu Lys Asn Tyr Gln Asp Met Val Val
            100                 105                 110

Glu Gly Cys Gly Cys Arg
        115

<210> SEQ ID NO 24
<211> LENGTH: 118
<212> TYPE: PRT
<213> ORGANISM: Homo sapiens

<400> SEQUENCE: 24

Lys Arg Ser Pro Lys His His Ser Gln Arg Ala Arg Lys Lys Asn Lys
1               5                   10                  15

Asn Cys Arg Arg His Ser Leu Tyr Val Asp Phe Ser Asp Val Gly Trp
```

```
                    20                  25                  30
Asn Asp Trp Ile Val Ala Pro Pro Gly Tyr Gln Ala Phe Tyr Cys His
            35                  40                  45
Gly Asp Cys Pro Phe Pro Leu Ala Asp His Leu Asn Ser Thr Asn His
        50                  55                  60
Ala Ile Val Gln Thr Leu Val Asn Ser Val Asn Ser Ser Ile Pro Lys
65                  70                  75                  80
Ala Cys Cys Val Pro Thr Glu Leu Ser Ala Ile Ser Met Leu Tyr Leu
                85                  90                  95
Asp Glu Tyr Asp Lys Val Val Leu Lys Asn Tyr Gln Glu Met Val Val
            100                 105                 110
Glu Gly Cys Gly Cys Arg
            115

<210> SEQ ID NO 25
<211> LENGTH: 119
<212> TYPE: PRT
<213> ORGANISM: Homo sapiens

<400> SEQUENCE: 25

Ser Arg Gly Ser Gly Ser Ser Asp Tyr Asn Gly Ser Glu Leu Lys Thr
1               5                   10                  15
Ala Cys Lys Lys His Glu Leu Tyr Val Ser Phe Gln Asp Leu Gly Trp
                20                  25                  30
Gln Asp Trp Ile Ile Ala Pro Lys Gly Tyr Ala Ala Asn Tyr Cys Asp
            35                  40                  45
Gly Glu Cys Ser Phe Pro Leu Asn Ala His Met Asn Ala Thr Asn His
        50                  55                  60
Ala Ile Val Gln Thr Leu Val His Leu Met Asn Pro Glu Tyr Val Pro
65                  70                  75                  80
Lys Pro Cys Cys Ala Pro Thr Lys Leu Asn Ala Ile Ser Val Leu Tyr
                85                  90                  95
Phe Asp Asp Asn Ser Asn Val Ile Leu Lys Lys Tyr Arg Asn Met Val
            100                 105                 110
Val Arg Ala Cys Gly Cys His
            115

<210> SEQ ID NO 26
<211> LENGTH: 119
<212> TYPE: PRT
<213> ORGANISM: Homo sapiens

<400> SEQUENCE: 26

Leu Arg Met Ala Asn Val Ala Glu Asn Ser Ser Asp Gln Arg Gln
1               5                   10                  15
Ala Cys Lys Lys His Glu Leu Tyr Val Ser Phe Arg Asp Leu Gly Trp
                20                  25                  30
Gln Asp Trp Ile Ile Ala Pro Glu Gly Tyr Ala Ala Tyr Tyr Cys Glu
            35                  40                  45
Gly Glu Cys Ala Phe Pro Leu Asn Ser Tyr Met Asn Ala Thr Asn His
        50                  55                  60
Ala Ile Val Gln Thr Leu Val His Phe Ile Asn Pro Glu Thr Val Pro
65                  70                  75                  80
Lys Pro Cys Cys Ala Pro Thr Gln Leu Asn Ala Ile Ser Val Leu Tyr
                85                  90                  95
Phe Asp Asp Ser Ser Asn Val Ile Leu Lys Lys Tyr Arg Asn Met Val
```

Val Arg Ala Cys Gly Cys His
        115

<210> SEQ ID NO 27
<211> LENGTH: 119
<212> TYPE: PRT
<213> ORGANISM: Homo sapiens

<400> SEQUENCE: 27

Ser Arg Met Ser Ser Val Gly Asp Tyr Asn Thr Ser Glu Gln Lys Gln
1               5                   10                  15

Ala Cys Lys Lys His Glu Leu Tyr Val Ser Phe Arg Asp Leu Gly Trp
            20                  25                  30

Gln Asp Trp Ile Ile Ala Pro Glu Gly Tyr Ala Ala Phe Tyr Cys Asp
        35                  40                  45

Gly Glu Cys Ser Phe Pro Leu Asn Ala His Met Asn Ala Thr Asn His
    50                  55                  60

Ala Ile Val Gln Thr Leu Val His Leu Met Phe Pro Asp His Val Pro
65                  70                  75                  80

Lys Pro Cys Cys Ala Pro Thr Lys Leu Asn Ala Ile Ser Val Leu Tyr
                85                  90                  95

Phe Asp Asp Ser Ser Asn Val Ile Leu Lys Lys Tyr Arg Asn Met Val
            100                 105                 110

Val Arg Ser Cys Gly Cys His
        115

<210> SEQ ID NO 28
<211> LENGTH: 120
<212> TYPE: PRT
<213> ORGANISM: Homo sapiens

<400> SEQUENCE: 28

Glu Gln Thr Leu Lys Lys Ala Arg Arg Lys Gln Trp Ile Glu Pro Arg
1               5                   10                  15

Asn Cys Ala Arg Arg Tyr Leu Lys Val Asp Phe Ala Asp Ile Gly Trp
            20                  25                  30

Ser Glu Trp Ile Ile Ser Pro Lys Ser Phe Asp Ala Tyr Tyr Cys Ser
        35                  40                  45

Gly Ala Cys Gln Phe Pro Met Pro Lys Ser Leu Lys Pro Ser Asn His
    50                  55                  60

Ala Thr Ile Gln Ser Ile Val Arg Ala Val Gly Val Val Pro Gly Ile
65                  70                  75                  80

Pro Glu Pro Cys Cys Val Pro Glu Lys Met Ser Ser Leu Ser Ile Leu
                85                  90                  95

Phe Phe Asp Glu Asn Lys Asn Val Val Leu Lys Val Tyr Pro Asn Met
            100                 105                 110

Thr Val Glu Ser Cys Ala Cys Arg
        115                 120

<210> SEQ ID NO 29
<211> LENGTH: 116
<212> TYPE: PRT
<213> ORGANISM: Homo sapiens

<400> SEQUENCE: 29

Gly Pro Gly Arg Ala Gln Arg Ser Ala Gly Ala Thr Ala Ala Asp Gly
1               5                   10                  15

```
Pro Cys Ala Leu Arg Glu Leu Ser Val Asp Leu Arg Ala Glu Arg Ser
            20                  25                  30

Val Leu Ile Pro Glu Thr Tyr Gln Ala Asn Asn Cys Gln Gly Val Cys
        35                  40                  45

Gly Trp Pro Gln Ser Asp Arg Asn Pro Arg Tyr Gly Asn His Val Val
    50                  55                  60

Leu Leu Leu Lys Met Gln Ala Arg Gly Ala Ala Leu Ala Arg Pro Pro
65                  70                  75                  80

Cys Cys Val Pro Thr Ala Tyr Ala Gly Lys Leu Leu Ile Ser Leu Ser
                85                  90                  95

Glu Glu Arg Ile Ser Ala His His Val Pro Asn Met Val Ala Thr Glu
                100                 105                 110

Cys Gly Cys Arg
            115

<210> SEQ ID NO 30
<211> LENGTH: 122
<212> TYPE: PRT
<213> ORGANISM: Homo sapiens

<400> SEQUENCE: 30

Ala Leu Arg Leu Leu Gln Arg Pro Pro Glu Glu Pro Ala Ala His Ala
1               5                   10                  15

Asn Cys His Arg Val Ala Leu Asn Ile Ser Phe Gln Glu Leu Gly Trp
            20                  25                  30

Glu Arg Trp Ile Val Tyr Pro Pro Ser Phe Ile Phe His Tyr Cys His
        35                  40                  45

Gly Gly Cys Gly Leu His Ile Pro Pro Asn Leu Ser Leu Pro Val Pro
    50                  55                  60

Gly Ala Pro Pro Thr Pro Ala Gln Pro Tyr Ser Leu Leu Pro Gly Ala
65                  70                  75                  80

Gln Pro Cys Cys Ala Ala Leu Pro Gly Thr Met Arg Pro Leu His Val
                85                  90                  95

Arg Thr Thr Ser Asp Gly Gly Tyr Ser Phe Lys Tyr Glu Thr Val Pro
                100                 105                 110

Asn Leu Leu Thr Gln His Cys Ala Cys Ile
            115                 120

<210> SEQ ID NO 31
<211> LENGTH: 122
<212> TYPE: PRT
<213> ORGANISM: Homo sapiens

<400> SEQUENCE: 31

His Arg Arg Arg Arg Gly Leu Glu Cys Asp Gly Lys Val Asn Ile
1               5                   10                  15

Cys Cys Lys Lys Gln Phe Phe Val Ser Phe Lys Asp Ile Gly Trp Asn
            20                  25                  30

Asp Trp Ile Ile Ala Pro Ser Gly Tyr His Ala Asn Tyr Cys Glu Gly
        35                  40                  45

Glu Cys Pro Ser His Ile Ala Gly Thr Ser Gly Ser Ser Leu Ser Phe
    50                  55                  60

His Ser Thr Val Ile Asn His Tyr Arg Met Arg Gly His Ser Pro Phe
65                  70                  75                  80

Ala Asn Leu Lys Ser Cys Cys Val Pro Thr Lys Leu Arg Pro Met Ser
                85                  90                  95
```

```
Met Leu Tyr Tyr Asp Asp Gly Gln Asn Ile Ile Lys Lys Asp Ile Gln
            100                 105                 110

Asn Met Ile Val Glu Glu Cys Gly Cys Ser
            115                 120

<210> SEQ ID NO 32
<211> LENGTH: 121
<212> TYPE: PRT
<213> ORGANISM: Homo sapiens

<400> SEQUENCE: 32

His Arg Ile Arg Lys Arg Gly Leu Glu Cys Asp Gly Arg Thr Asn Leu
1               5                   10                  15

Cys Cys Arg Gln Gln Phe Phe Ile Asp Phe Arg Leu Ile Gly Trp Asn
            20                  25                  30

Asp Trp Ile Ile Ala Pro Thr Gly Tyr Tyr Gly Asn Tyr Cys Glu Gly
        35                  40                  45

Ser Cys Pro Ala Tyr Leu Ala Gly Val Pro Gly Ser Ala Ser Ser Phe
    50                  55                  60

His Thr Ala Val Val Asn Gln Tyr Arg Met Arg Gly Leu Asn Pro Gly
65                  70                  75                  80

Thr Val Asn Ser Cys Cys Ile Pro Thr Lys Leu Ser Thr Met Ser Met
                85                  90                  95

Leu Tyr Phe Asp Asp Glu Tyr Asn Ile Val Lys Arg Asp Val Pro Asn
            100                 105                 110

Met Ile Val Glu Glu Cys Gly Cys Ala
            115                 120

<210> SEQ ID NO 33
<211> LENGTH: 115
<212> TYPE: PRT
<213> ORGANISM: Homo sapiens

<400> SEQUENCE: 33

His Arg Arg Ala Leu Asp Thr Asn Tyr Cys Phe Ser Ser Thr Glu Lys
1               5                   10                  15

Asn Cys Cys Val Arg Gln Leu Tyr Ile Asp Phe Arg Lys Asp Leu Gly
            20                  25                  30

Trp Lys Trp Ile His Glu Pro Lys Gly Tyr His Ala Asn Phe Cys Leu
        35                  40                  45

Gly Pro Cys Pro Tyr Ile Trp Ser Leu Asp Thr Gln Tyr Ser Lys Val
    50                  55                  60

Leu Ala Leu Tyr Asn Gln His Asn Pro Gly Ala Ser Ala Ala Pro Cys
65                  70                  75                  80

Cys Val Pro Gln Ala Leu Glu Pro Leu Pro Ile Val Tyr Tyr Val Gly
                85                  90                  95

Arg Lys Pro Lys Val Glu Gln Leu Ser Asn Met Ile Val Arg Ser Cys
            100                 105                 110

Lys Cys Ser
        115

<210> SEQ ID NO 34
<211> LENGTH: 115
<212> TYPE: PRT
<213> ORGANISM: Homo sapiens

<400> SEQUENCE: 34
```

```
Lys Lys Arg Ala Leu Asp Ala Ala Tyr Cys Phe Arg Asn Val Gln Asp
1               5                   10                  15
Asn Cys Cys Leu Arg Pro Leu Tyr Ile Asp Phe Lys Arg Asp Leu Gly
            20                  25                  30
Trp Lys Trp Ile His Glu Pro Lys Gly Tyr Asn Ala Asn Phe Cys Ala
        35                  40                  45
Gly Ala Cys Pro Tyr Leu Trp Ser Ser Asp Thr Gln His Ser Arg Val
    50                  55                  60
Leu Ser Leu Tyr Asn Thr Ile Asn Pro Glu Ala Ser Ala Ser Pro Cys
65                  70                  75                  80
Cys Val Ser Gln Asp Leu Glu Pro Leu Thr Ile Leu Tyr Tyr Ile Gly
                85                  90                  95
Lys Thr Pro Lys Ile Glu Gln Leu Ser Asn Met Ile Val Lys Ser Cys
                100                 105                 110
Lys Cys Ser
        115

<210> SEQ ID NO 35
<211> LENGTH: 115
<212> TYPE: PRT
<213> ORGANISM: Homo sapiens

<400> SEQUENCE: 35

Lys Lys Arg Ala Leu Asp Thr Asn Tyr Cys Phe Arg Asn Leu Glu Glu
1               5                   10                  15
Asn Cys Cys Val Arg Pro Leu Tyr Ile Asp Phe Arg Gln Asp Leu Gly
            20                  25                  30
Trp Lys Trp Val His Glu Pro Lys Gly Tyr Tyr Ala Asn Phe Cys Ser
        35                  40                  45
Gly Pro Cys Pro Tyr Leu Arg Ser Ala Asp Thr Thr His Ser Thr Val
    50                  55                  60
Leu Gly Leu Tyr Asn Thr Leu Asn Pro Glu Ala Ser Ala Ser Pro Cys
65                  70                  75                  80
Cys Val Pro Gln Asp Leu Glu Pro Leu Thr Ile Leu Tyr Tyr Val Gly
                85                  90                  95
Arg Thr Pro Lys Val Glu Gln Leu Ser Asn Met Val Val Lys Ser Cys
                100                 105                 110
Leu Cys Ser
        115

<210> SEQ ID NO 36
<211> LENGTH: 4
<212> TYPE: PRT
<213> ORGANISM: Artificial Sequence
<220> FEATURE:
<223> OTHER INFORMATION: proteolytic cleavage site
<220> FEATURE:
<221> NAME/KEY: MISC_FEATURE
<222> LOCATION: (1)..(4)
<223> OTHER INFORMATION: Xaa = Any Amino Acid

<400> SEQUENCE: 36

Arg Xaa Xaa Arg
1

<210> SEQ ID NO 37
<211> LENGTH: 4
<212> TYPE: PRT
<213> ORGANISM: Artificial Sequence
<220> FEATURE:
```

```
-continued

<223> OTHER INFORMATION: Eukaryotic-  proteolytic processing site

<400> SEQUENCE: 37

Arg Ser Arg Arg
1
```

CHICKEN GROWTH DIFFERENTIATION FACTOR-8

CROSS REFERENCE TO RELATED APPLICATIONS

This application is a divisional application of U.S. application Ser. No. 10/997,809 filed Nov. 23, 2004, now issued as U.S. Pat. No. 7,399,848; which is a continuation application of U.S. application Ser. No. 10/278,803 filed Oct. 22, 2002, now issued as U.S. Pat. No. 6,858,208; which is a continuation application of U.S. application Ser. No. 09/451,501 filed Nov. 30, 1999, now issued as U.S. Pat. No. 6,468,535; which is a divisional application of U.S. application Ser. No. 08/795,071 filed Feb. 5, 1997, now issued as U.S. Pat. No. 5,994,618; which is a continuation-in-part application of U.S. application Ser. No. 08/525,596 filed Oct. 26, 1995, now issued as U.S. Pat. No. 5,827,733; which is a 35 USC §371 National Stage application of International Application No. PCT/US94/03019 filed Mar. 18, 1994; which is a continuation-in-part application of U.S. application Ser. No. 08/033,923 filed Mar. 19, 1993, now abandoned. The disclosure of each of the prior applications is considered part of and is incorporated by reference in the disclosure of this application.

BACKGROUND OF THE INVENTION

1. Field of the Invention

The invention relates generally to growth factors and specifically to a new member of the transforming growth factor beta (TGF-β) superfamily, which is denoted, growth differentiation factor-8 (GDF-8).

2. Description of Related Art

The Transforming growth factor β (TGF-β) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), *Drosophila* decapentaplegic (DPP) gene product, which is required for dorsal-ventral axis formation and morphogenesis of the imaginal disks (Padgett, et al., *Nature*, 325:81-84, 1987), the *Xenopus* Vg-1 gene product, which localizes to the vegetal pole of eggs ((Weeks, et al., *Cell*, 51:861-867, 1987), the activins (Mason, et al., *Biochem, Biophys. Res. Commun.,* 135:957-964, 1986), which can induce the formation of mesoderm and anterior structures in *Xenopus* embryos (Thomsen, et al., *Cell*, 63:485, 1990), and the bone morphogenetic proteins (BMPS, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis, hematopolesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110-140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A. et al., *Science*, 247:1328, 1990). Additional studies by Hammonds, et al., (*Molec. Endocrin.* 5: 149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., *Nature,* 321:779, 1986) and the TGF-βs (Cheifetz, et al., *Cell,* 48:409, 1987), heterodimers have also been detected, and these appear to have different biological properties than the respective homodimers.

In addition it is desirable to produce livestock and game animals, such as cows, sheep, pigs, chicken and turkey, fish which are relatively high in musculature and protein, and low in fat content.

Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to produce animals which are genetically predisposed to having higher muscle content, without any ancillary increase in fat levels.

The food industry has put much effort into increasing the amount of muscle and protein in foodstuffs. This quest is relatively simple in the manufacture of synthetic foodstuffs, but has been met with limited success in the preparation of animal foodstuffs. Attempts have been made, for example, to lower cholesterol levels in beef and poultry products by including cholesterol-lowering drugs in animal feed (see e.g. Elkin and Rogler, *J. Agric. Food Chem.* 1990, 38, 1635-1641). However, there remains a need for more effective methods of increasing muscle and reducing fat and cholesterol levels in animal food products.

SUMMARY OF THE INVENTION

The present invention provides a cell growth and differentiation factor, GDF-8, a polynucleotide sequence which encodes the factor, and antibodies which are immunoreactive with the factor. This factor appears to relate to various cell proliferative disorders, especially those involving muscle, nerve, and adipose tissue.

In one embodiment, the invention provides a method for detecting a cell proliferative disorder of muscle, nerve, or fat origin and which is associated with GDF-8. In another embodiment, the invention provides a method for treating a cell proliferative disorder by suppressing or enhancing GDF-8 activity.

In another embodiment, the subject invention provides non-human transgenic animals which are useful as a source of food products with high muscle and protein content, and reduced fat and cholesterol content. The animals have been altered chromosomally in their germ cells and somatic cells so that the production of GDF-8 is produced in reduced amounts, or is completely disrupted, resulting in animals with decreased levels of GDF-8 in their system and higher than normal levels of muscle tissue, preferably without increased fat and/or cholesterol levels. Accordingly, the present invention also includes food products provided by the animals. Such food products have increased nutritional value because of the increase in muscle tissue. The transgenic non-human animals of the invention include bovine, porcine, ovine and avian animals, for example.

The subject invention also provides a method of producing animal food products having increased muscle content. The method includes modifying the genetic makeup of the germ cells of a pronuclear embryo of the animal, implanting the embryo into the oviduct of a pseudopregnant female thereby allowing the embryo to mature to full term progeny, testing the progeny for presence of the transgene to identify transgene-positive progeny, cross-breeding transgene-positive progeny to obtain further transgene-positive progeny and processing the progeny to obtain foodstuff. The modification of the germ cell comprises altering the genetic composition so as to disrupt or reduce the expression of the naturally occurring gene encoding for production of GDF-8 protein. In a particular embodiment, the transgene comprises antisense polynucleotide sequences to the GDF-8 protein. Alternatively, the transgene may comprise a non-functional sequence which replaces or intervenes in the native GDF-8 gene.

The subject invention also provides a method of producing avian food products having improved muscle content. The method includes modifying the genetic makeup of the germ cells of a pronuclear embryo of the avian animal, implanting the embryo into the oviduct of a pseudopregnant female into an embryo of a chicken, culturing the embryo under conditions whereby progeny are hatched, testing the progeny for presence of the genetic alteration to identify transgene-positive progeny, cross-breeding transgene-positive progeny and processing the progeny to obtain foodstuff.

BRIEF DESCRIPTION OF THE DRAWINGS

FIG. 2 shows nucleotide and predicted amino acid sequences of murine GDF-8 (FIG. 2A: SEQ ID NOs: 5 and 6, respectively), human GDF-8 (FIG. 2B: SEQ ID NOs: 7 and 8, respectively), rat GDF-8 (FIG. 2C: SEQ ID NOs: 18 and 19, respectively) and chicken GDF-8 (FIG. 2D: SEQ ID NOs 20 and 21, respectively). The putative dibasic processing sites in the murine sequence are boxed.

FIG. 3A shows the alignment of the C-terminal sequences of GDF-8 (amino acid residues 264-375 of SEQ ID NO: 14) with other members of the TGF-β superfamily (SEQ ID NOs: 22-35). The conserved cysteine residues are boxed. Dashes denote gaps introduced in order to maximize alignment.

FIG. 3B shows the alignment of the C-terminal sequences of GDF-8 from human (SEQ ID NO: 8), murine (SEQ ID NO: 6), rat (SEQ ID NO: 19) and chicken (SEQ ID NO: 21) sequences.

FIG. 4 shows amino acid homologies among different members of the TGF superfamily. Numbers represent percent amino acid identities between each pair calculated from the first conserved cysteine to the C-terminus. Boxes represent homologies among highly-related members within particular subgroups.

FIGS. 5A-5D show the sequence of GDF-8. Nucleotide (SEQ ID NO: 11) and amino acid (SEQ ID NO: 12) sequences of murine GDF-8 cDNA clones (FIGS. 5A and 5B: GenBank accession number U84005); and nucleotide (SEQ ID NO: 13) and amino acid (SEQ ID NO: 14) sequences of human GDF-8 cDNA clones FIGS. 5C and 5D) are shown. Numbers indicate nucleotide position relative to the 5' end. Consensus N-linked glycosylation signals are shaded. The putative RXXR (SEQ ID NO: 36) proteolytic cleavage sites are boxed.

FIG. 7 shows a comparison of murine (SEQ ID NO: 6) and human (SEQ ID NO: 8)GDF-8 amino acid sequences. The predicted murine sequence is shown in the top lines and the predicted human sequence is shown in the bottom lines. Numbers indicate amino acid position relative to the N-terminus. Identities between the two sequences are denoted by a vertical line.

DETAILED DESCRIPTION OF THE INVENTION

Figure 1A:
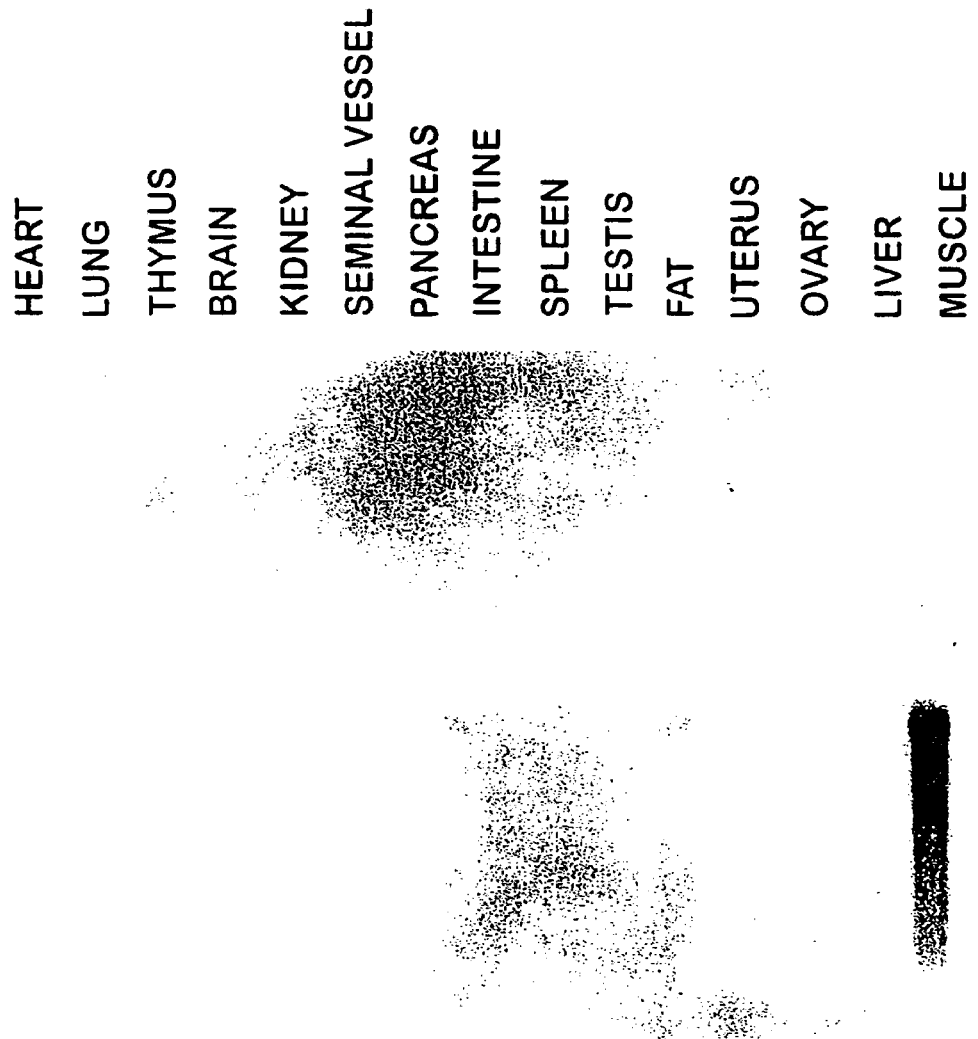
FIG. 1A is a Northern blot showing expression of GDF-8 mRNA in adult tissues. The probe was a partial murine GDF-8 clone.

The present invention provides a growth and differentiation factor, GDF-8 and a polynucleotide sequence encoding GDF-8. GDF-8 is expressed at highest levels in muscle and at lower levels in adipose tissue.

The animals contemplated for use in the practice of the subject invention are those animals generally regarded as useful for the processing of food stuffs, i.e. avian such as meat bred and egg laying chicken and turkey, ovine such as lamb, bovine such as beef cattle and milk cows, piscine and porcine. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-8 protein of this invention and the members of the TGF-β family, indicates that GDF-8 is a new member of the family of growth and differentiation factors. Based on the known activities of many of the other members, it can be expected that GDF-8 will also possess biological activities that will make it useful as a diagnostic and therapeutic reagent.

In particular, certain members of this superfamily have expression patterns or possess activities that relate to the function of the nervous system. For example, the inhibins and activins have been shown to be expressed in the brain (Meunier, et al., *Proc. Natl. Acad. Sci.*, USA, 85:247, 1988; Sawchenko, et al., *Nature,* 334:615, 1988), and activin has been shown to be capable of functioning as a nerve cell survival molecule (Schubert, et al., *Nature,* 344:868, 1990). Another family member, namely, GDF-1, is nervous sys-tem-specific in its expression pattern (Lee, S. J., *Proc. Natl. Acad. Sci.*, USA, 88:4250, 1991), and certain other family members, such as Vgr-1 (Lyons, et al., *Proc. Natl. Acad. Sci.*, USA, 86:4554, 1989; Jones, et al., *Development,* 111:531, 1991), OP-1 (Ozkaynak, et al., *J. Biol. Chem.,* 267:25220, 1992), and BMP-4 (Jones, et al., *Development,* 111:531, 1991), are also known to be expressed in the nervous system. Because it is known that skeletal muscle produces a factor or factors that promote the survival of motor neurons (Brown, *Trends Neurosci.,* 7:10, 1984), the expression of GDF-8 in muscle suggests that one activity of GDF-8 may be as a trophic factor for neurons. In this regard, GDF-8 may have applications in the treatment of neurodegenerative diseases, such as amyotrophic lateral sclerosis or muscular dystrophy, or in maintaining cells or tissues in culture prior to transplantation.

GDF-8 may also have applications in treating disease processes involving muscle, such as in musculodegenerative diseases or in tissue repair due to trauma. In this regard, many other members of the TGF-β family are also important mediators of tissue repair. TGF-β has been shown to have marked effects on the formation of collagen and to cause a striking angiogenic response in the newborn mouse (Roberts, et al., *Proc. Natl. Acad. Sci.*, USA 83:4167, 1986). TGF-β has also been shown to inhibit the differentiation of myoblasts in culture (Massague, et al., *Proc. Natl. Acad. Sci.*, USA 83:8206, 1986). Moreover, because myoblast cells may be used as a vehicle for delivering genes to muscle for gene therapy, the properties of GDF-8 could be exploited for maintaining cells prior to transplantation or for enhancing the efficiency of the fusion process.

The expression of GDF-8 in adipose tissue also raises the possibility of applications for GDF-8 in the treatment of obesity or of disorders related to abnormal proliferation of adipocytes. In this regard, TGF-β has been shown to be a potent inhibitor of adipocyte differentiation in vitro (Ignotz and Massague, *Proc. Natl. Acad. Sci., USA* 82:8530, 1985).

The term "substantially pure" as used herein refers to GDF-8 which is substantially free of other proteins, lipids, carbohydrates or other materials with which it is naturally associated. One skilled in the art can purify GDF-8 using standard techniques for protein purification. The substantially pure polypeptide will yield a single major band on a non-reducing polyacrylamide gel. The purity of the GDF-8 polypeptide can also be determined by amino-terminal amino acid sequence analysis. GDF-8 polypeptide includes functional fragments of the polypeptide, as long as the activity of GDF-8 remains. Smaller peptides containing the biological activity of GDF-8 are included in the invention.

The invention provides polynucleotides encoding the GDF-8 protein. These polynucleotides include DNA, cDNA and RNA sequences which encode GDF-8. It is understood that all polynucleotides encoding all or a portion of GDF-8 are also included herein, as long as they encode a polypeptide with GDF-8 activity. Such polynucleotides include naturally occurring, synthetic, and intentionally manipu-lated polynucleotides. For example, GDF-8 polynucleotide may be subjected to site-directed mutagenesis. The polynucleotide sequence for GDF8 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-8 polypeptide encoded by the nucleotide sequence is functionally unchanged.

Specifically disclosed-herein is a genomic DNA sequence containing a portion of the GDF-8 gene. The sequence contains an open reading frame corresponding to the predicted C-terminal region of the GDF-8 precursor protein. The encoded polypeptide is predicted to contain two potential proteolytic processing sites (KR and RR). Cleavage of the precursor at the downstream site would generate a mature biologically active C-terminal fragment of 109 and 103 amino acids for murine and human species, respectively, with a predicted molecular weight of approximately 12,400. Also disclosed are full length murine and human GDF-8 cDNA sequences. The murine pre-pro-GDF-8 protein is 376 amino acids in length, which is encoded by a 2676 base pair nucleotide sequence, beginning at nucleotide 104 and extending to a TGA stop codon at nucleotide 1232. The human GDF-8 protein is 375 amino acids and is encoded by a 2743 base pair sequence, with the open reading frame beginning at nucleotide 59 and extending to nucleotide 1184. GDF-8 is also capable of forming dimers, or heterodimers, with an expected molecular weight of approximately 23-30 KD (see Example 4). For example, GDF-8 may form heterodimers with other family members, such as GDF-11.

Also provided herein are the biologically active C-terminal fragments of chicken (FIG. 2C) and rat (FIG. 2D) GDF-8. As shown in FIG. 3B, alignment of the amino acid sequences of human, murine, rat and chicken GDF-8 indicate that the sequences are 100% identical in the C-terminal biologically active fragment. Therefore, it would now be routine for one of skill in the art to obtain the GDF-8 nucleic acid and amino acid sequence for GDF-8 from any species, including those provided herein, as well as porcine, bovine, ovine, and piscine.

The C-terminal region of GDF-8 following the putative proteloytic processing site shows significant homology to the known members of the TGF-β superfamily. The GDF-8 sequence contains most of the residues that are highly conserved in other family members and in other species (see FIGS. 3A and 3B). Like the TGF-βs and inhibin βs, GDF-8 contains an extra pair of cysteine residues in addition to the 7 cysteines found in virtually all other family members. Among the known family members, GDF-8 is most homologous to Vgr-1 (45% sequence identity) (see FIG. 4).

Minor modifications of the recombinant GDF-8 primary amino acid sequence may result in proteins which have substantially equivalent activity as compared to the GDF-8 polypeptide described herein. Such modifications may be deliberate, as by site-directed mutagenesis, or may be spontaneous. All of the polypeptides produced by these modifications are included herein as long as the biological activity of GDF-8 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-8 biological activity.

The nucleotide sequence encoding the GDF-8 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-8 polynucleotide of the invention is derived from a mammalian organism, and most preferably from mouse, rat, cow, pig, or human. GDF-8 polynucleotides from chicken, fish and other species are also included herein. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9:879, 1981).

The development of specific DNA sequences encoding GDF-8 can also be obtained by: 1) isolation of double-stranded DNA sequences from the genomic DNA; 2) chemical manufacture of a DNA sequence to provide the necessary codons for the polypeptide of interest; and 3) in vitro synthesis of a doublestranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for GDF-8 peptides having at least one epitope, using antibodies specific for GDF-8. Such antibodies can be either polyclonally or monoclonally derived and used to detect expression product indicative of the presence of GDF-8 cDNA.

DNA sequences encoding GDF-8 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-8 polynucleotide sequences may be inserted into a recombinant expression vector. The term "recombinant expression vector" refers to a plasmid, virus or other vehicle known in the art that has been manipulated by insertion or incorporation of the GDF-8 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding GDF-8 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-8 is expressed from a cDNA clone containing the entire coding sequence of GDF-8. Alternatively, the C-terminal portion of GDF-8 can be expressed as a fusion protein with the pro-region of another member of the TGF-β family or co-expressed with another pro-region (see for example, Hammonds, et al., *Molec. Endocrin.,* 5:149, 1991; Gray, A., and Mason, A., *Science,* 247:1328, 1990).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-8 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-8 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and $F(ab')_2$' Fv and SCA fragments which are capable of binding an epitopic determinant on GDF-8.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An $(Fab')_2$ fragment of an antibody can be obtained by treating a whole antibody molecule with the enzyme pepsin, without subsequent reduction, A $(Fab')_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used in this invention, the term "epitope" refers to an antigenic determinant on an antigen, such as a GDF-8 polypeptide, to which the paratope of an antibody, such as an GDF-8-specific antibody, binds. Antigenic determinants usually consist of chemically active surface groupings of molecules, such as amino acids or sugar side chains, and can have specific three-dimensional structural characteristics, as well as specific charge characteristics.

As is mentioned above, antigens that can be used in producing GDF-8-specific antibodies include GDF-8 polypeptides or GDF-8 polypep-tide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-8 polynucleotide that is an antisense molecule is useful in treating malignancies of the various organ systems, particularly, for example, cells in muscle or adipose tissue. Essentially, any disorder which is etiologically linked to altered expression of GDF-8 could be considered susceptible to treatment with a GDF-8 agent (e.g., a suppressing or enhancing agent). One such disorder is a malignant cell proliferative disorder, for example.

The invention provides a method for detecting a cell proliferative disorder of muscle or adipose tissue which comprises contacting an anti-GDF-8 antibody with a cell suspected of having a GDF-8 associated disorder and detecting binding to the antibody. The antibody reactive with GDF-8 is labeled with a compound which allows detection of binding to GDF-8. For purposes of the invention, an antibody specific for GDF-8 polypeptide may be used to detect the level of GDF-8 in biological fluids and tissues. Any specimen containing a detectable amount of antigen can be used. A preferred sample of this invention is muscle tissue. The level of GDF-8 in the suspect cell can be compared with the level in a normal cell to determine whether the subject has a GDF-8-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140-250 keV range, which may readily be detected by conventional gamma cameras.

For in vivo diagnosis radioisotopes may be bound to immunoglobulin either directly or indirectly by using an intermediate functional group. intermediate functional groups which often are used to bind radioisotopes which exist as metallic ions to immunoglobulins are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-8-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-8-associated disease is effective. The term "ameliorate" denotes a lessening of the detrimental effect of the GDF-8-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Treatment includes administration of a reagent which modulates activity. The term "modulate" envisions the suppression or expression of GDF-8 when it is over-expressed, or augmentation of GDF-8 expression when it is underexpressed. When a muscle associated disorder is associated with GDF-8 overexpression, such suppressive reagents as antisense GDF-8 polynucleotide sequence or GDF-8 binding antibody can be introduced into a cell. In addition, an anti-idiotype antibody which binds to a monoclonal antibody which binds GDF-8 of the invention, or an epitope thereof, may also be used in the therapeutic method of the invention. Alternatively, when a cell proliferative disorder is associated with underexpression or expression of a mutant GDF-8 polypeptide, a sense polynucleotide sequence (the DNA coding strand) or GDF-8 polypeptide can be introduced into the cell. Such muscle-associated disorders include cancer, muscular dystrophy, spinal cord injury, traumatic injury, congestive obstructive pulmonary disease (COPD), AIDS or cachecia.

Thus, where a cell-proliferative disorder is associated with the expression of GDF-8, nucleic acid sequences that interfere with GDF-8 expression at the translational level can be used. This approach utilizes, for example, antisense nucleic acid and ribozymes to block translation of a specific GDF-8 mRNA, either by masking that mRNA with an antisense nucleic acid or by cleaving it with a ribozyme. Such disorders include neurodegenerative diseases, for example. In addition, dominant-negative GDF-8 mutants would be useful to actively interfere with function of "normal" GDF-8.

Antisense nucleic acids are DNA or RNA molecules that are complementary to at least a portion of a specific molecule (Weintraub, *Scientific American,* 262:40, 1990). In the cell, the antisense nucleic acids hybridize to the corresponding forming a double-stranded molecule. The antisense nucleic acids interfere with the translation of the mRNA since the cell will not translate a mRNA that is double-stranded.

Antisense of about 15 nucleotides are preferred, since they are easily synthesized and are less likely to cause problems than larger molecules when introduced into the target GDF-8-producing cell. The use of antisense methods to inhibit the in vitro translation of genes is well known in the art (Marcus-Sakura, *Anal. Biochem.,* 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.,* 260:3030, 1988). A major advantage of this approach is that, because they are sequence-specific, only mRNAs with particular Sequences are inactivated.

There are two basic types of ribozymes namely, tetrahymena-type (Hasselhoff, *Nature,* 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-8 protein. Such therapy would achieve its therapeutic effect by introduction of the GDF-8 antisense polynucleotide into cells having the proliferative disorder. Delivery of antisense GDF-8 polynucleotide can be achieved using a recombinant expression vector such as a chimeric virus or a colloidal dispersion system. Especially preferred for therapeutic delivery of antisense sequences is the use of targeted liposomes. In contrast, when it is desirable to enhance GDF-8 production, a "sense" GDF-8 polynucleotide is introduced into the appropriate cell(s).

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV) Harvey murine sarcoma virus murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-8 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-8 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include, but are not limited to ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-8 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends BioChem. Sci.*, 6:77, 1981). In addition to mammalian cells, liposomes have been used for delivery of polynucleotides in plant, yeast and bacterial cells. in order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Manning, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidyiglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-8 in muscle and adipose tissue, there are a variety of applications using the polypeptide, polynucleotide, and antibodies of the invention, related to these tissues. Such applications include treatment of cell proliferative disorders involving these and other tissues, such as neural tissue.

In addition, GDF-8 may be useful in various gene therapy procedures. In embodiments where GDF-8 polypeptide is administered to a subject, the dosage range is about 0.1 ug/kg to 100 mg/kg; more preferably from about 1 ug/kg to 75 mg/kg and most preferably from about 10 mg/kg to 50 mg/kg.

The data in Example 6 shows that the human GDF-8 gene is located on chromosome 2. By comparing the chromosomal location of GDF-8 with the map positions of various human disorders, it should be possible to determine whether mutations in the GDF-8 gene are involved in the etiology of human diseases. For example, an autosomal recessive form of juvenile amyotrophic lateral sclerosis has been shown to map to chromosome 2 (Hentati, et al., *Neurology*, 42 [Supp1.3]:201, 1992). More precise mapping of GDF-8 and analysis of DNA from these patients may indicate that GDF-8 is, in fact, the gene affected in this disease. In addition, GDF-8 is useful for distinguishing chromosome 2 from other chromosomes.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If micro-injection is to be used with avian species, however, a recently published procedure by Love et al., (*Biotechnology*, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention bovine, porcine, ovine and avian animals (e.g., cow, pig, sheep, chicken). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., *Proc. Natl. Acad. Sci. USA* 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i-e., animals which include the exogenous genetic material within all of their cells in both alleles. 50% of the resulting animals will include the exogenous genetic material within one allele and 25% will include no exogenous genetic material.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., *Proc. Natl. Acad. Sci. USA* 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927-6931, 1985; Van der Putten, et al., *Proc. Natl. Acad. Sci. USA* 82:6148-6152, 1985). Transfection is easily and efficiently obtained by culturing the blastomeres on a monolayer of virus-producing cells (Van der Putten, supra; Stewart, et al., *EMBO J.* 6:383-388, 1987). Alternatively, infection can be performed at a later stage. Virus or virus-producing cells can be injected into the blastocoele (D. Jahner et al., *Nature* 298:623-628, 1982) Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154-156, 1981; M. O. Bradley et al., *Nature* 309:255-258, 1984; Gossler, et al., *Proc. Natl. Acad. Sci. USA* 83:9065-9069, 1986; and Robertson et al., *Nature* 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode GDF-8, and include GDF-sense and antisense polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion-targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a modified GDF-8 coding sequence. In a preferred embodiment, the GDF-8 gene is disrupted by homologous targeting in embryonic stem cells. For example, the entire mature C-terminal region of the GDF-8 gene may be deleted as described in the examples below. Optionally, the GDF-8 disruption or deletion may be accompanied by insertion of or replacement with other DNA sequences, such as a non-functional GDF-8 sequence. In other embodiments, the transgene comprises DNA antisense to the coding sequence for GDF-8. In another embodiment, the transgene comprises DNA encoding an antibody or receptor peptide sequence which is able to bind to GDF-8. The DNA and peptide sequences of GDF-8 are known in the art, the sequences, localization and activity disclosed in WO94/21681 and pending U.S. patent application Ser. No. 08/033,923, filed on Mar. 19, 1993, incorporated by reference in its entirety. The disclosure of both of these applications are hereby incorporated herein by reference. Where appropriate, DNA sequences that encode proteins having GDF-8 activity but differ in nucleic acid sequence due to the degeneracy of the genetic code may also be used herein, as may truncated forms, allelic variants and interspecies homologues.

Therefore the invention also includes animals having heterozygous mutations in GDF-8. A heterozygote would likely have an intermediate increase in muscle mass as compared to the homozygote.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous GDF-8 gene(s), a marker gene fragment can be included in the construct in the 3' untranslated region of the transgene and the Northern probe designed to probe for the marker gene fragment. The serum levels of GDF-8 can also be measured in the transgenic animal to establish appropriate expression. Expression of the GDF-8 transgenes, thereby decreasing the GDF-8 in the tissue and serum levels of the transgenic animals and consequently increasing the muscle tissue content results in the foodstuffs from these animals (i.e. eggs, beef, pork, poultry meat, milk, etc.) having markedly increased muscle content, and preferably without increased, and more preferably, reduced levels of fat and cholesterol. By practice of the subject invention, a statistically significant increase in muscle content, preferably at least a 2% increase in muscle content (e.g., in chickens), more preferably a 25% increase in muscle content as a percentage of body weight, more preferably greater than 40% increase in muscle content in these foodstuffs can be obtained.

Thus, the present invention includes methods for increasing muscle mass in domesticated animals, characterized by inactivation or deletion of the gene encoding growth and differentiation factor-8 (GDF-8). The domesticated animal is preferably selected from the group consisting of ovine, bovine, porcine, piscine and avian. The animal may be treated with an isolated polynucleotide sequence encoding growth and differentiation factor-8 which polynucleotide sequence is also from a domesticated animal selected from the group consisting of ovine, bovine, porcine, piscine and avian. The present invention includes methods for increasing the muscle mass in domesticated animals characterized by administering to a domesticated animal monoclonal antibodies directed to the GDF-8 polypeptide. The antibody may be an anti-GDF-8, and may be either a monoclonal antibody or a polyclonal antibody.

The invention includes methods comprising using an anti-GDF-8 monoclonal antibody as a therapeutic agent to inhibit the growth regulating actions of GDF-8 on muscle cells. Muscle cells are defined to include fetal or adult muscle cells, as well as progenitor cells which are capable of differentiation into muscle. The monoclonal antibody may be a humanized (e.g., either fully or a chimeric) monoclonal antibody, of any species origin, such as murine, ovine, bovine, porcine or avian. Methods of producing antibody molecules with various combinations of "humanized" antibodies are well known in the art and include combining murine variable regions with human constant regions (Cabily, et al. *Proc. Natl Acad. Sci. USA,* 3273, 1984), or by grafting the murine-antibody complementary determining regions (CDRs) onto the human framework (Richmann, et al., *Nature* 332:323, 1988). Other general references which teach methods for creating humanized antibodies include Morrison, et al., *Science,* 229:1202, 1985; Jones, et al., *Nature,* 321:522, 1986; Monroe, et al., *Nature* 312:779, 1985; Oi, et al., BioTechniques, 4:214, 1986; European Patent Application No. 302,620; and U.S. Pat. No. 5,024,834. Therefore, by humanizing the monoclonal antibodies of the invention for in vivo use, an immune response to the antibodies would be greatly reduced.

The monoclonal antibody, GDF-8 polypeptide, or GDF-8 polynucleotide (all "GDF-8 agents") may have the effect of increasing the development of skeletal muscles. In preferred embodiments of the claimed methods, the GDF-8 monoclonal antibody, polypeptide, or polynucleotide is administered to a patient suffering from a disorder selected from the group consisting of muscle wasting disease, neuromuscular disorder, muscle atrophy or aging. The GDF-8 agent may also be administered to a patient suffering from a disorder selected from the group consisting of muscular dystrophy, spinal cord injury, traumatic injury, congestive obstructive pulmonary disease (COPD), AIDS or cachechia. In a preferred embodiment, the GDF-8 agent is administered to a patient with muscle wasting disease or disorder by intravenous, intramuscular or subcutaneous injection; preferably, a monoclonal antibody is administered within a dose range between about 0.1 mg/kg to about 100 mg/kg; more preferably between about 1 ug/kg to 75 mg/kg; most preferably from about 10 mg/kg to 50 mg/kg. The antibody may be administered, for example, by bolus injunction or by slow infusion. Slow infusion over a period of 30 minutes to 2 hours is preferred. The GDF-8 agent may be formulated in a formulation suitable for administration to a patient. Such formulations are known in the art.

The dosage regimen will be determined by the attending physician considering various factors which modify the action of the GDF-8 protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of agent, such as anti-GDF-8 antibodies, to be used in the composition. Generally, systemic or injectable administration, such as intravenous (IV), intramuscular (IM) or subcutaneous (Sub-Q) injection. Administration will generally be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), human, bovine, or chicken growth hormone which may aid in increasing muscle mass, to the final composition, may also affect the dosage. In the embodiment where an anti-GDF-8 antibody is administered, the anti-GDF-8 antibody is generally administered within a dose range of about 0.1 ug/kg to about 100 mg/kg.; more preferably between about 10 mg/kg to 50 mg/kg.

Progress can be monitored by periodic assessment of tissue growth and/or repair. The progress can be monitored, for example, x-rays, histomorphometric determinations and tetracycline labeling.

All references cited herein are hereby incorporated by reference in their entirety The following examples are intended to illustrate but not limit the invention. While they are typical of those that might be used, other procedures known to those skilled in the art may alternatively be used. .

EXAMPLE 1

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on muse genomic DNA followed by subcloning the PCR products using restriction sites placed at the 5' ends of the primers, picking individual E. coli colonies carrying these subcloned inserts, and using a combination of random sequencing and hybridization analysis to eliminate known members of the superfamily. GDF-8 was identified from a mixture of PCR products obtained with the primers SJL141: 5'-CCGGAATTCGGITGG (G/C/A) A (G/A/TIC) (A/G) A (T/C) TGG (A/G) TI (A/G) TI (T/G) CICC-3' (SEQ ID NO:1) SJL147: 5'-CCGGAATTC (G/A) CAI (G/C)C(G/A) CA (G/A) CT (GIA/T/C) TCIACI (G/A) (T/C) CAT-3' (SEQ ID NO:2)

PCR using these primers was carried out with 2 μg mouse genomic DNA at 94° C. for 1 min, 50° C. for 2 min, and 72° C. for 2 min for 40 cycles.

PCR products of approximately 280 bp were gel-purified, digested with Eco R1, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from nonhybridizing colonies for sequence analysis.

The primer combination of SJL141 and SJL147, encoding the amino acid sequences GW (H/Q/N/K/D/E) (D/N)W(V/I/M) (V/I/M) (A/S)P (SEQ ID NO:9) and M(V/I/M/T/A)V(D/E)SC(G/A) C (SEQ ID NO: 10), respectively, yielded four previously identified sequences (BMP-4, inhibin, βB, GDF-3 and GDF-5) and one novel sequence, which was designated GDF-8, among 110 subclones analyzed.

```
Human GDF-8 was isolated using the primers:
ACM13:
                                      (SEQ ID NO:3)
5'-CGCGGATCCAGAGTCAAGGTGACAGACACAC-3';
and ACM14:
                                      (SEQ ID NO:4)
5'-CGCGGATCCTCCTCATGAGCACCCACAGCGGTC-3'
```

PCR using these primers was carried out with one μg human genomic DNA at 94° C. for 1 min, 58° C. for 2 min, and 72° C. for 2 min for 30 cycles. The PCR product was digested with Bam H1, gel-purified, and subcloned in the Bluescript vector (Stratagene, San Francisco, Calif.).

EXAMPLE 2

Expression Pattern and Sequence of GDF-8

Figure 1B:
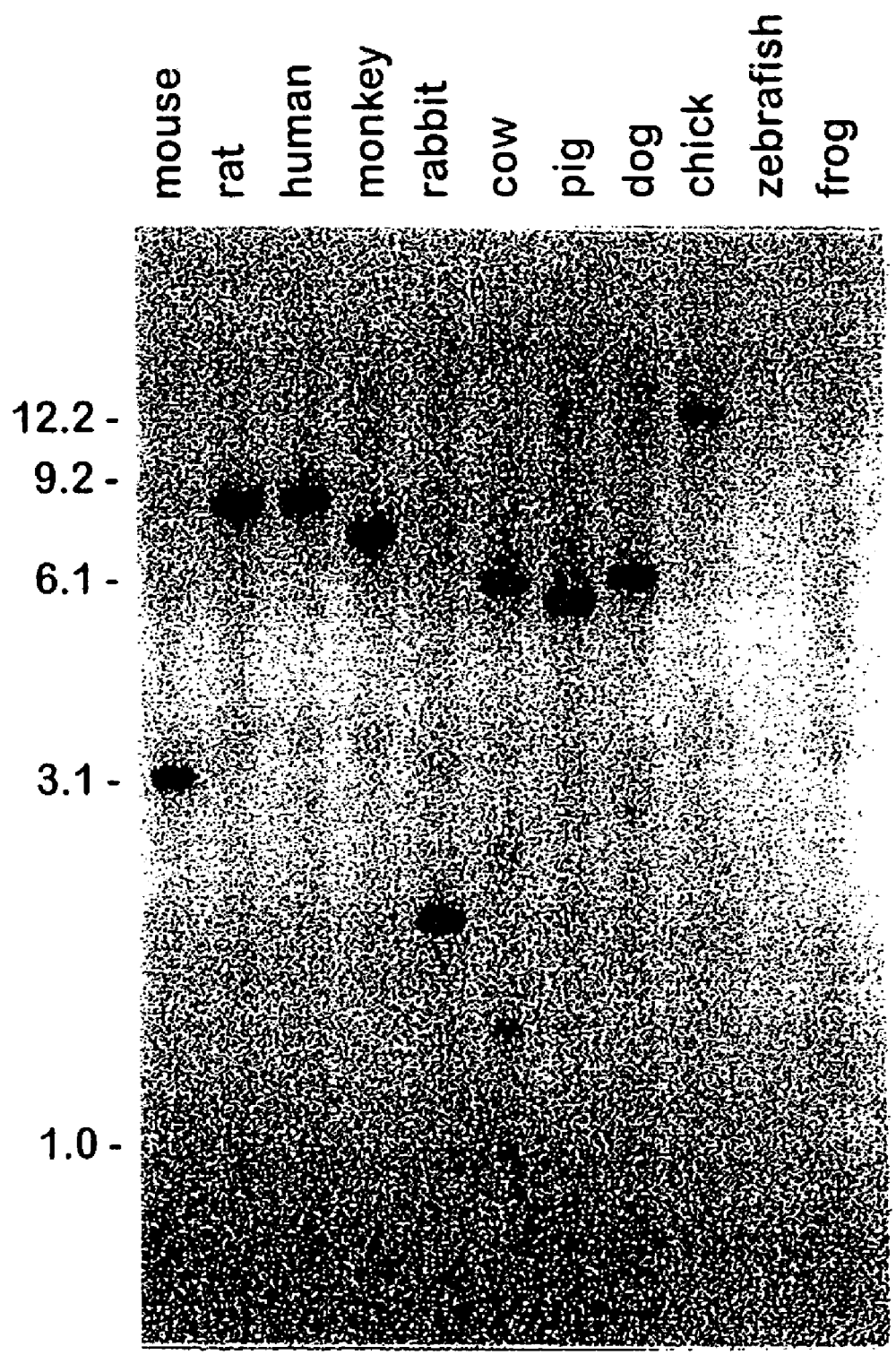
FIG. 1B is a Southern blot showing GDF-8 genomic sequences identified in mouse, rat, human, monkey, rabbit, cow, pig, dog and chicken.

To determine the expression pattern of GDF-8, RNA samples prepared from a variety of adult tissues were screened by Northern analysis. RNA isolation and Northern analysis were carried out as described previously (Lee, S. J., Mol. Endocrinol., 4:1034, 1990) except that hybridization was carried out in 5×SSPE, 10% dextran sulfate, 50% formamide, 1% SDS, 200 μg/ml salmon DNA, and 0.1% each of bovine serum albumin, ficoll, and polyvinylpyrrolidone. Five micrograms of twice poly A-selected RNA prepared from each tissue (except for muscle, for which only 2 μg RNA was used) were electrophoresed on formaldehyde gels, blotted, and probed with GDF-8. As shown in FIG. 1, the GDF-8 probe detected a single mRNA species expressed at highest levels in muscle and at significantly lower levels in adipose tissue.

To obtain a larger segment of the GDF-8 gene, a mouse genomic library was screened with a probe derived from the GDF-8 PCR product. The partial sequence of a GDF-8 genomic clone is shown in FIG. 2A. The sequence contains an open reading frame corresponding to the predicted C-terminal region of the GDF-8 precursor protein. The predicted GDF-8 sequence contains two potential proteolytic processing sites, which are boxed. Cleavage of the precursor at the second of these sites would generate a mature C terminal fragment 109 amino acids in length with a predicted molecular weight of 12,400. The partial sequence of human GDF-8 is shown in FIG. 2B. Assuming no PCR-induced errors during the isolation of the human clone, the human and mouse amino acid sequences in this region are 100% identical.

The C-terminal region of GDF-8 following the putative proteolytic processing site shows significant homology to the known members of the TGF-β; superfamily (FIG. 3). FIG. 3 shows the alignment of the C-terminal sequences of GDF-8 with the corresponding regions of human GDF-1 (Lee, Proc. Natl. Acad. Sci. USA, 88:4250-4254, 1991), human BMP-2 and 4 (Wozney, et al., Science, 242:1528-1534, 1988), human Vgr-1 (Celeste, et al. Proc. Natl. Acad. Sci. USA, 87:9843-9847, 1990), human OP-1 (Ozkaynak, et al., EMBO J., 9:2085-2093, 1990), human BMP-5 (Celeste, et al., Proc. Natl. Acad. Sci. USA, 87:9843-9847, 1990), human BMP-3 (Wozney, et al., Science, 242:1528-1534, 1988), human MiS (Cate, et al. Cell, 45:685-698, 1986), human inhibin alpha, βA, and βB (Mason, et al., Biochem, Biophys. Res. Commun., 135:957-964, 1986), human TGF-β1 (Derynck, et al., Nature, 316:701-705, 1985), human TGF-R2 (deMartin, et al., ELMO J, 6:3673-3677, 1987), and human TGF-β3 (ten Dijke, et al., Proc. Natl. Acad. Sci. USA, 85:4715-4719, 1988). The conserved cysteine residues are boxed. Dashes denote gaps introduced in order to maximize the alignment.

GDF-8 contains most of the residues that are highly conserved in other family members, including the seven cysteine residues with their characteristic spacing. Like the TGF-βs and inhibin βs, GDF-8 also contains two additional cysteine residues. In the case of TGF-β2, these two additional cysteine residues are known to form an intramolecular disulfide bond (Daopin, et al., Science, 257:369, 1992; Schlunegger and Grutter, Nature, 358:430, 1992).

FIG. 4 shows the amino acid homologies among the different members of the TGF-β superfamily. Numbers represent percent amino acid identities between each pair calculated from the first conserved cysteine to the C terminus. Boxes represent homologies among highly-related members within particular subgroups. In this region, GDF-8 is most homologous to Vgr-1 (45% sequence identity).

EXAMPLE 3

Isolation of cDNA Clones Encoding Murine and Human GDF-8

In order to isolate full-length cDNA clones encoding murine and human GDF-8, cDNA libraries were prepared in the lambda ZAP II vector (Stratagene) using RNA prepared from skeletal muscle. From 5 μg of twice poly A-selected RNA prepared from murine and human muscle, cDNA libraries consisting of 4.4 million and 1.9 million recombinant phage, respectively, were constructed according to the instructions provided by Stratagene. These libraries were screened without amplification. Library screening and characterization of cDNA inserts were carried out as described previously (Lee, *Mol. Endocrinol.*, 4:1034-1040).

Figure 6A:
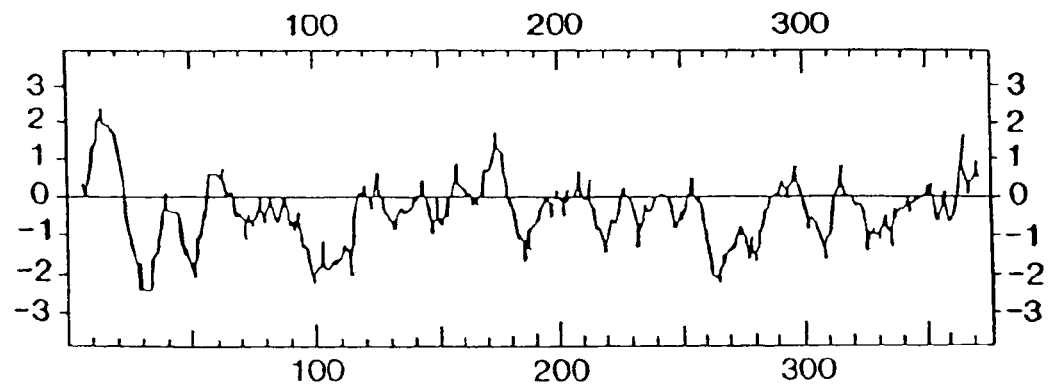
FIG. 6 shows a hydropathicity profile of GDF-8. Average hydropho-bicity values for murine (FIG. 6A) and human (FIG. 6B) GDF-8 were calculated using the method of Kyte and Doolittle (*J. Mol. Biol.*, 157:105-132, 1982). Positive numbers indicate increasing hydrophobicity.

From $2.4 \times 10^6$ recombinant phage screened from the murine muscle cDNA library, greater than 280 positive phage were identified using a murine GDF-8 probe derived from a genomic clone, as described in Example 1. The entire nucleotide sequence of the longest cDNA insert analyzed is shown in FIG. 5A and SEQ ID NO: 11. The 2676 base pair sequence contains a single long open reading frame beginning with a methionine codon at nucleotide 104 and extending to a TGA stop codon at nucleotide 1232. Upstream of the putative initiating methionine codon is an in-frame stop codon at nucleotide 23. The predicted pre-pro-GDF-8 protein is 376 amino acids in length. The sequence contains a core of hydrophobic amino acids at the N-terminus suggestive of a signal peptide for secretion (FIG. 6A), one potential N-glycosylation site at asparagine 72, a putative RXXR proteolytic cleavage site at amino acids 264-267, and a C-terminal region showing significant homology to the known members of the TGF-β superfamily. Cleavage of the precursor protein at the putative RXXR site would generate a mature C-terminal GDF-8 fragment 109 amino acids in length with a predicted molecular weight of approximately 12,400.

Figure 6B:
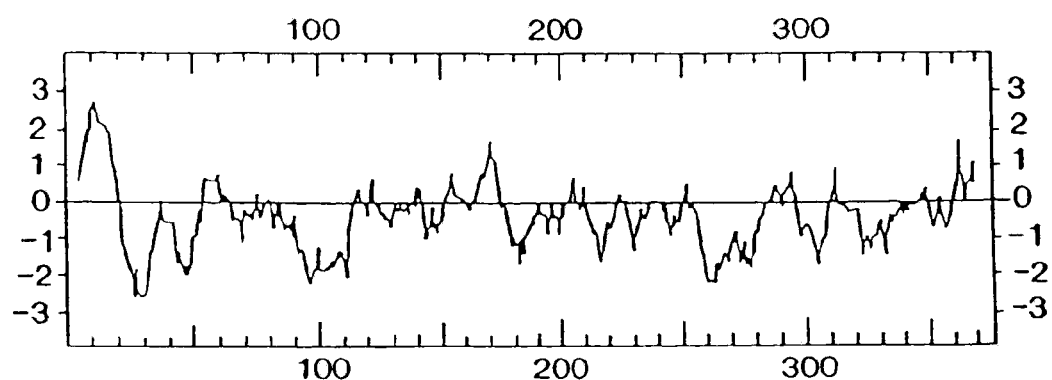

From $1.9 \times 10^6$ recombinant phage screened from the human muscle cDNA library, 4 positive phage were identified using a human GDF-8 probe derived by polymerase chain reaction on human genomic DNA. The entire nucleotide sequence of the longest cDNA insert is shown in FIG. 5B and SEQ ID NO: 13. The 2743 base pair sequence contains a single long open reading frame beginning with a methionine codon at nucleotide 59 and extending to a TGA stop codon at nucleotide 1184. The predicted pre-pro-GDF-8 protein is 375 amino acids in length. The sequence contains a core of hydrophobic amino acids at the N-terminus suggestive of a signal peptide for secretion (FIG. 6B), one potential N-glycosylation site at asparagine 71, and a putative RX) (R proteolytic cleavage site at amino acids 263-266. FIG. 7 shows a comparison of the predicted murine (top) and human (boKom) GDF-8 amino acid sequences. Numbers indicate amino acid position relative to the N-terminus. Identities between the two sequences are denoted by a vertical line. Murine and human GDF-8 are approximately 94% identical in the predicted pro-regions and 100% identical following the predicted RXXR cleavage sites.

EXAMPLE 4

Dimerization of GDF-8

To determine whether the processing signals in the GDF-8 sequence are functional and whether GDF-8 forms dimers like other members of the TGF-β superfamily, the GDF-8 cDNA was stably expressed in CHO cells. The GDF-8 coding sequence was cloned into the pMSXND expression vector (Lee and Nathans, *J. Biol. Chem.*, 263:3521, (1988) and trans-fected into CHO cells. Following G418 selection, the cells were selected in 0.2 μM methotrexate, and conditioned medium from resistant cells was concentrated and electrophoresed on SDS gels. Conditioned medium was prepared by Cell Trends, Inc. (Middletown, Md.). For preparation of anti-GDF-8 serum, the C-terminal region of GDF-8 (amino acids 268 to 376) was expressed in bacteria using the RSET vector (Invitrogen, San Diego, Calif.), purified using a nickle chelate column, and injected into rabbits. All immunizations were carried out by Spring Valley Labs (Woodbine, Md.). Western analysis using $[^{125}I]$ iodoprotein A was carried out as described (Burnette, W. N., *Anal. Biochem.*, 112:195, 1981). Western analysis of conditioned medium prepared from these cells using an antiserum raised against a bacterially-expressed C-terminal fragment of GDF-8 detected two protein species with apparent molecular weights of approximately 52K and 15K under reducing conditions, consistent with unprocessed and processed forms of GDF-8, respectively. No bands were obtained either with preimmune serum or with conditioned medium from CHO cells transfected with an antisense construct. Under non-reducing conditions, the GDF-8 antiserum detected two predominant protein species with apparent molecular weights of approximately 101K and 25K, consistent with dimeric forms of unprocessed and processed GDF-8, respectively. Hence, like other TGF-β family members, GDF-8 appears to be secreted and proteolytically processed, and the C-terminal region appears to be capable of forming a disulfide-linked dimer.

EXAMPLE 5

Figure 8:
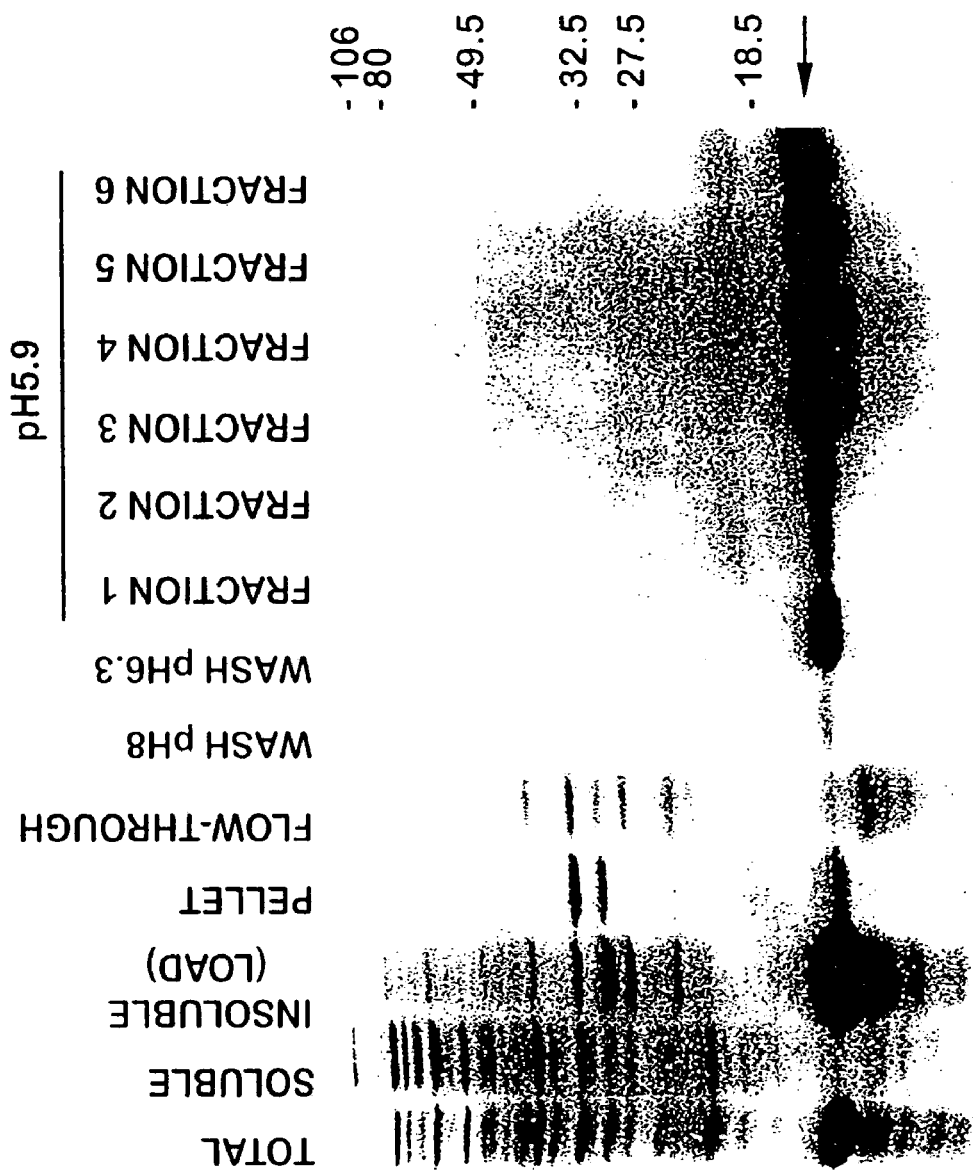
FIG. 8 shows the expression of GDF-8 in bacteria. BL21 (DE3) (pLysS) cells carrying a pRSET/GDF-8 expression plasmid were induced with isopropylthio-β-galactoside, and the GDF-8 fusion protein was purified by metal chelate chromatography. Lanes: total=total cell lysate; soluble=soluble protein fraction; insoluble=insoluble protein fraction (resuspended in 10 Mmn Tris pH 8.0, 50 mM sodium phosphate, 8 M urea, and 10 mM β-mercaptoethanol [buffer B]) loaded onto the column, pellet=insoluble protein fraction discarded before loading the column; flowthrough=proteins not bound by the column; washes=washes carried out in buffer B at the indicated pH's. Positions of molecular weight standards are shown at the right. Arrow indicates the position of the GDF-8 fusion protein.

Preparation of Antibodies Against GDF-8 and Expression of GDF-8 in Mammalian Cells In order to prepare antibodies against GDF-8, GDF-8 antigen was expressed as a fusion protein in bacteria. A portion of murine GDF-8 cDNA spanning amino acids 268-376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600. The fusion construct was trans-formed into BL21 (DE3) (pLysS) cells, and expression of the fusion protein was induced by treatment with isopropylthio-β-galactoside as described (Rosenberg, et al., *Gene*, 56:125-135). The fusion protein was then purified by metal chelate chromatography according to the instructions provided by Invitrogen. A Coomassie blue-stained gel of unpurified and purified fusion proteins is shown in FIG. 8.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western analysis of sera both from immunized rabbits and from immunized chickens demonstrated the presence of antibodies directed against the fusion protein.

To express GDF-8 in mammalian cells, the murine GDF-8 cDNA sequence from nucleotides 48-1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, *J. Biol. Chem.*, 263:3521-3527). The resulting constructs were transfected into Chinese hamster ovary cells, and stable tranfectants were selected in the presence of G418. Two milliliters of conditioned media prepared from the G418-resistant cells were dialyzed, lyophilized, electrophoresed under denaturing, reducing conditions, transferred to nitrocellulose, and incubated with anti-GDF-8 antibodies (described above) and $[^{125}I]$ iodoproteinA.

Figure 9:
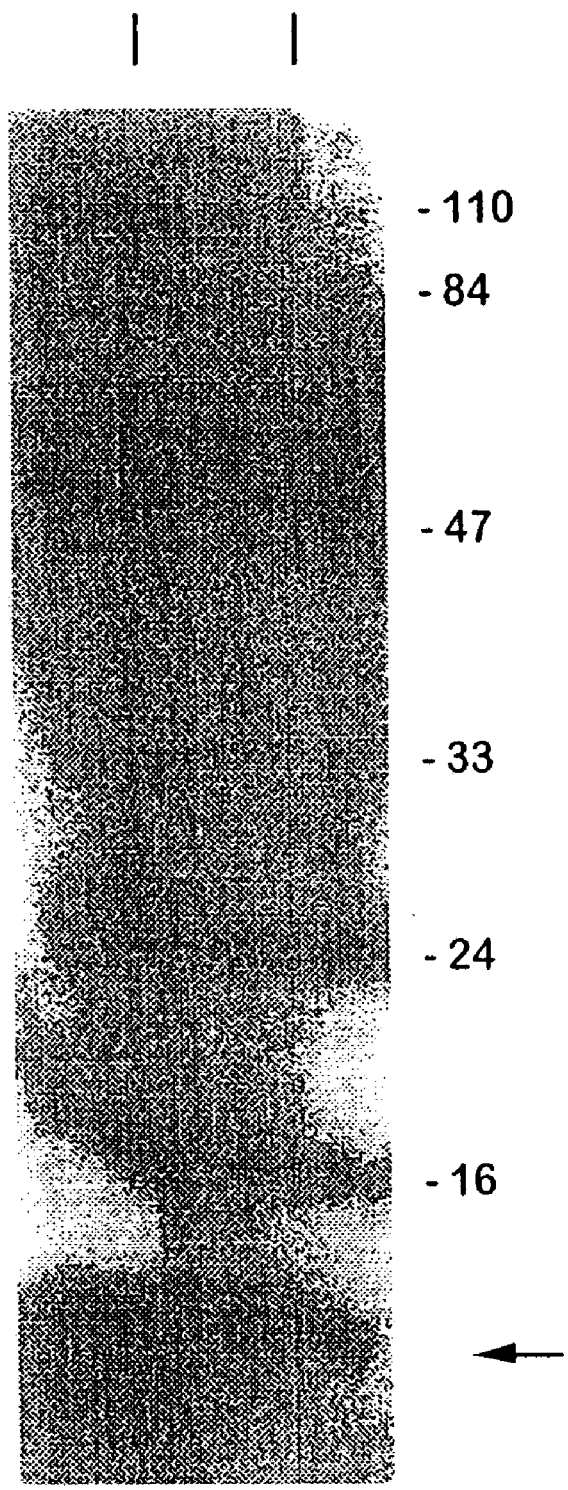
FIG. 9 shows the expression of GDF-8 in mammalian cells. Chinese hamster ovary cells were transfected with pMSXND/GDF-8 expression plasmids and selected in G418. Conditioned media from G418-resistant cells (prepared from cells transfected with constructs in which GDF-8 was cloned in either the antisense or sense orientation) were concentrated, electrophoresed under reducing conditions, blotted, and probed with anti-GDF-8 antibodies and [$^{125}$I]iodoproteinA. Arrow indicates the position of the processed GDF-8 protein.

As shown in FIG. 9, the rabbit GDF-8 antibodies (at a 1:500 dilution) detected a protein of approximately the predicted molecular weight for the mature C-terminal fragment of GDF-8 in the conditioned media of cells transfected with a construct in which GDF-8 had been cloned in the correct (sense) orientation with respect to the metallothionein promoter (lane 2); this band was not detected in a similar sample prepared from cells transfected with a control antisense construct (lane 1). Similar results were obtained using antibodies prepared in chickens. Hence, GDF-8 is secreted and proteolytically processed by these transfected mammalian cells.

EXAMPLE 6

Expression Pattern of GDF-8

Figure 10A:
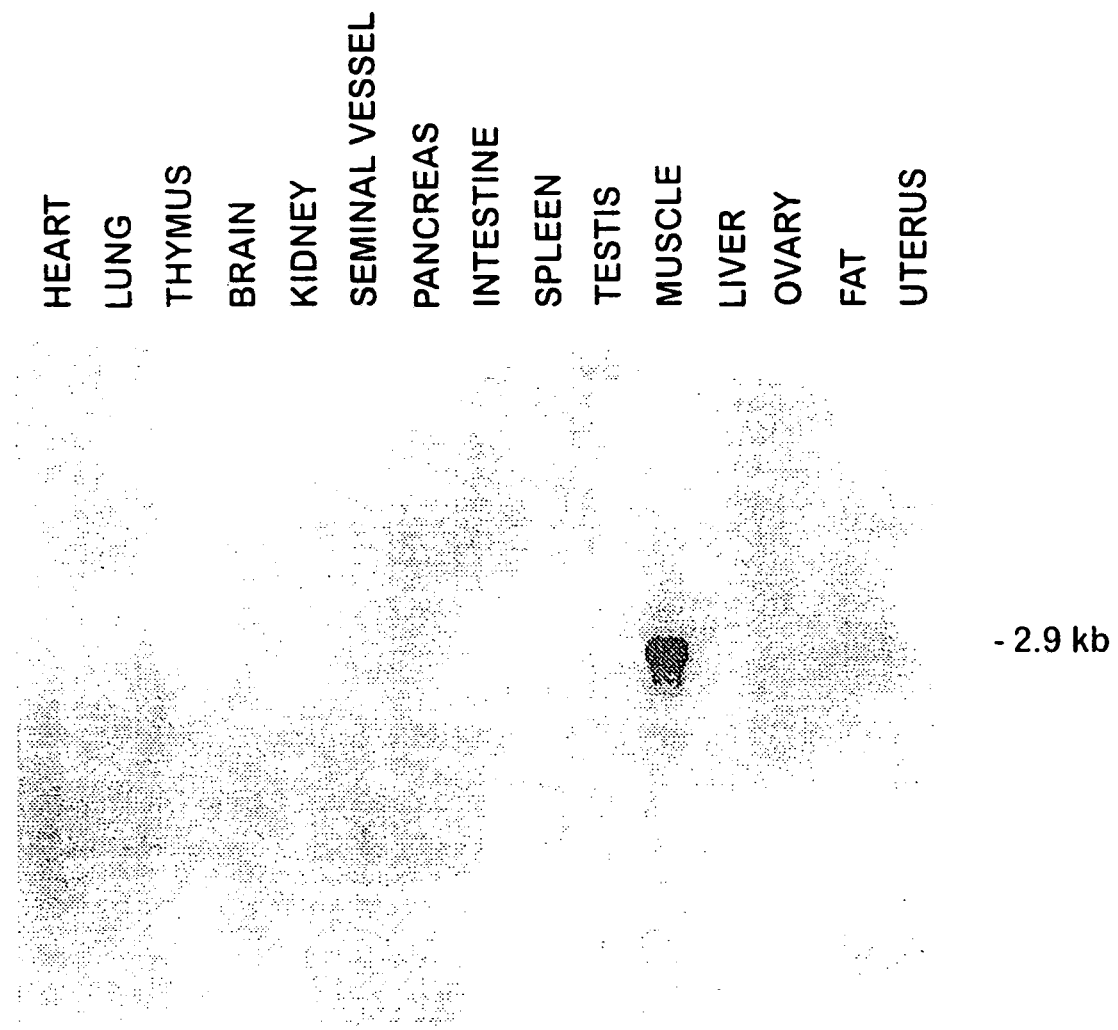
FIG. 10 shows the expression of GDF-8 mRNA. Poly A-selected RNA (5 µg each) prepared from adult tissues (FIG. 10A) or placentas end embryos (FIG. 10B) at the indicated days of gestation was electrophoresed on formaldehyde gels, blotted, and probed with full length murine GDF-8.
Figure 10B:
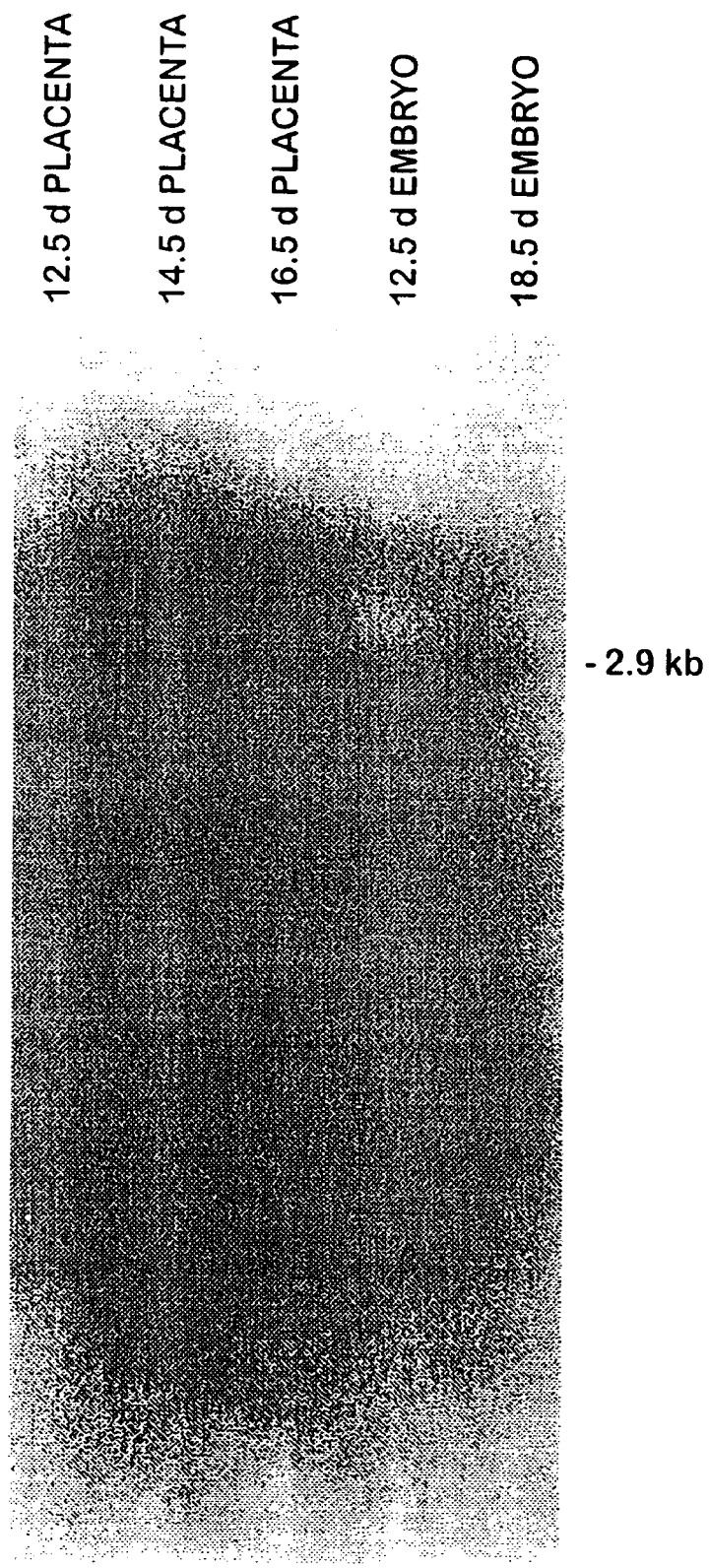

To determine the pattern of GDF-8, 5 µg of twice poly A-selected RNA prepared from a variety of murine tissue sources were subjected to Northern analysis. As shown in FIG. 10a (and as shown previously in Example 2), the GDF-8 probe detected a single mRNA species present almost exclusively in skeletal muscle among a large number of adult tissues surveyed. On longer exposures of the same blot, significantly lower but detectable levels of GDF-8 mRNA were seen in fat, brain, thymus, heart, and lung. Hence, these results confirm the high degree of specificity of GDF-8 expression in skeletal muscle. GDF-8 mRNA was also detected in mouse embryos at both gestational ages (day 12.5 and day 18.5 post-coital) examined but not in placentas at various stages of development (FIG. 10B).

To further analyze the expression pattern of GDF-8, in situ hybridization was performed on mouse embryos isolated at various stages of development. For all in situ hybridization experiments, probes corresponding to the C-terminal region of GDF-8 were excluded in order to avoid possible cross-reactivity with other members of the superfamily. Whole mount in situ hybridization analysis was carried out as described (Wilkinson, D. G., *In Situ Hybridization, A Practical Approach*, pp. 75-83, IRL. Press, Oxford, 1992) except that blocking and antibody incubation steps were carried out as in Knecht et al. (Knecht, et al., *Development*, 121:1927, 1955). Alkaline phosphatase reactions were carried out for 3 hours for day 10.5 embryos and overnight for day 9.5 embryos. Hybridization was carried out using digoxigenin-labelled probes spanning nucleotides 8-811 and 1298-2676, which correspond to the pro-region and 3' untranslated regions, respectively. In situ hybridization to sections was carried out as described (Wilkinson, et al., *Cell*, 50:79, 1987) using $^{35}$S-labelled probes ranging from approximately 100-650 bases in length and spanning nucleotides 8-793 and 1566-2595. Following hybridization and washing, slides were dipped in NTB-3 photographic emulsion, exposed for 16-19 days, developed and stained with either hematoxylin and eosin or toluidine blue. RNA isolation, poly A selection, and Northern analysis were carried out as described previously (McPherron and Lee, *J. Biol. Chem.*, 268:3444, 1993).

At all stages examined, the expression of GDF-8 mRNA appeared to be restricted to developing skeletal muscle. At early stages, GDF-8 expression was restricted to developing somites. By whole mount in situ hybridization analysis, GDF-8 mRNA could first be detected as early as day 9.5 post coitum in approximately one-third of the somites. At this stage of development, hybridization appeared to be restricted to the most mature (9 out of 21 in this example), rostral somites. By day 10.5 p.c., GDF-8 expression was clearly evident in almost every somite (28 out of 33 in this example shown). Based on in situ hybridization analysis of sections prepared from day 10.5 p.c. embryos, the expression of GDF-8 in somites appeared to be localized to the myotome compartment. At later stages of development, GDF-8 expression was detected in a wide range of developing muscles.

GDF-8 continues to be expressed in adult animals as well. By Northern analysis, GDF-8 mRNA expression was seen almost exclusively in skeletal muscle among the different adult tissues examined. A significantly lower though clearly detectable signal was also seen in adipose tissue. Based on Northern analysis of RNA prepared from a large number of different adult skeletal muscles, GDF-8 expression appeared to be widespread although the expression levels varied among individual muscles.

EXAMPLE 7

Chromosomal Localization of GDF-8

In order to map the chromosomal location of GDF-8, DNA samples from human/rodent somatic cell hybrids (Drwinga, et al., *Genomics*, 16:311-413, 1993; Dubois and Naylor, Genomics, 16:315-319, 1993) were analyzed by polymerase chain reaction followed by Southern blotting. Polymerase chain reaction was carried out using primer #83, 5'-CGCG-GATCCGTGGATCTAAATGAGAACAGTGAGC-3' (SEQ ID NO: 15) and primer #84, 5'-CGCGAATTCTCAGGTAAT-GATTGTTTCCGTTGTAGCG-3' (SEQ ID NO:16) for 40 cycles at 94° C. for 2 minutes, 60° C. for 1 minute, and 72° C. for 2 minutes. These primers correspond to nucleotides 119 to 143 (flanked by a Bam H1 recognition sequence), and nucleotides 394 to 418 (flanked by an Eco R1 recognition sequence), respectively, in the human GDF-8 cDNA sequence. PCR products were electrophoresed on agarose gels, blotted, and probed with oligonucleotide #100, 5'-ACACTAAATCTTCAAGAATA-3' (SEQ ID NO: 17), which corresponds to a sequence internal to the region flanked by primer #83 and #84. Filters were hybridized in 6×SSC, 1×Denhardt's solution, 100 Tg/ml yeast transfer RNA, and 0.05% sodium pyrophosphate at 50° C.

Figure 11:
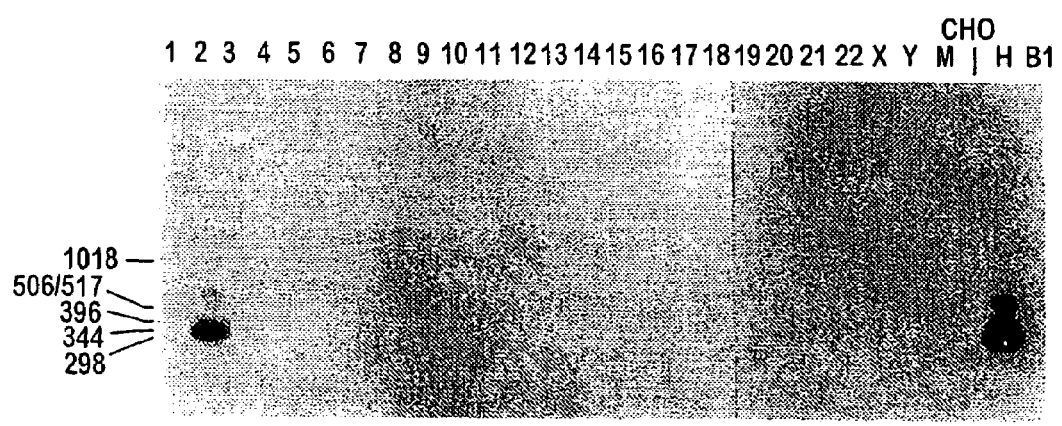
FIG. 11 shows chromosomal mapping of human GDF-8. DNA samples prepared from human/rodent somatic cell hybrid lines were subjected to PCR, electrophoresed on agarose gels, blotted, and probed. The human chromosome contained in each of the hybrid cell lines is identified at the top of each of the first 24 lanes (1-22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards.

As shown in FIG. 11, the human-specific probe detected a band of the predicted size (approximately 320 base pairs) in the positive control sample (total human genomic DNA) and in a single DNA sample from the human/rodent hybrid panel. This positive signal corresponds to human chromosome 2. The human chromosome contained in each of the hybrid cell lines is identified at the top of each of the first 24 lanes (1-22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards. These data show that the human GDF-8 gene is located on chromosome 2.

EXAMPLE 8

GDF-8 Transgenic Knockout Mice

Figure 12A:
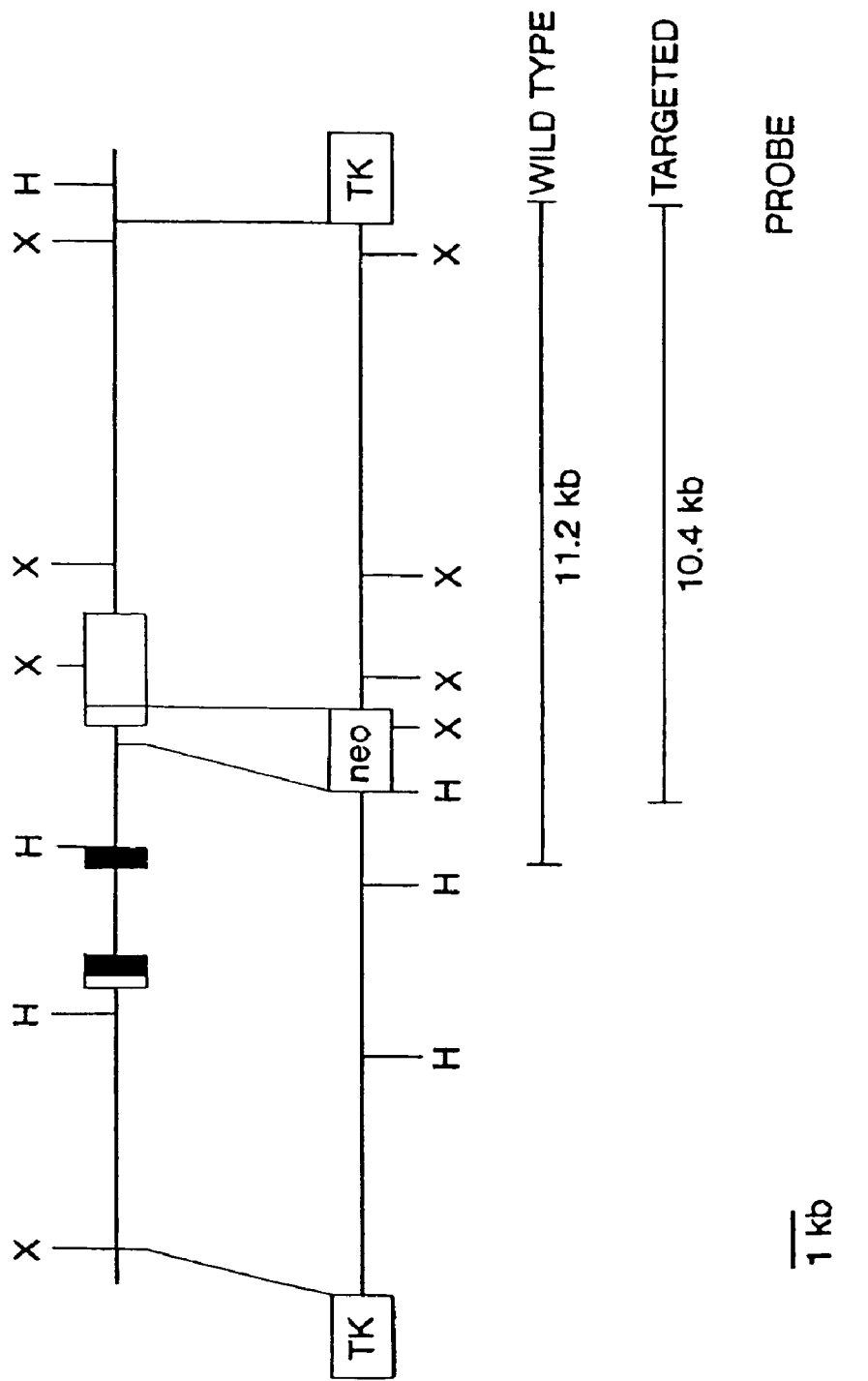
FIG. 12A shows a map of the GDF-8 locus (top line) and targeting construct (second line). The black and stippled boxes represent coding sequences for the pro- and C-terminal regions, respectively. The white boxes represent 5' and 3' untranslated sequences. A probe derived from the region downstream of the 3' homology fragment and upstream of the most distal HindIII site shown hybridizes to an 11.2 kb HindIII fragment in the GDF-8 gene and a 10.4 kb fragment in an homologously targeted gene. Abbreviations: H, HindIII; X, Xba I.

The GDF-8, we disrupted the GDF-8 gene was disrupted by homologous targeting in embryonic stem cells. To ensure that the resulting mice would be null for GDF-8 function, the entire mature C-terminal region was deleted and replaced by a neo cassette (FIG. 12A). A murine 129 SV/J genomic library was prepared in lambda FIX II according to the instructions provided by Stratagene (La Jolla, Calif.). The structure of the GDF-8 gene was deduced from restriction mapping and partial sequencing of phage clones isolated from this library. Vectors for preparing the targeting construct were kindly provided by Philip Soriano and Kirk Thomas University. R1 ES cells were transfected with the targeting construct, selected with gancyclovir (2 µM) and G418 (250 µg/ml), and analyzed by Southern analysis. Homologously targeted clones were injected into C57BL/6 blastocysts and transferred into pseudopregnant females. Germline transmission of the targeted allele was obtained in a total of 9 male chimeras from 5 independently-derived ES clones. Genomic Southern blots were hybridized at 42° C. as described above and washed in 0.2×SSC, 0.1% SDS at 42° C.

For whole leg analysis, legs of 14 week old mice were skinned, treated with 0.2 M EDTA in PBS at 4° C. for 4 weeks followed by 0.5 M sucrose in PBS at 4° C. For fiber number and size analysis, samples were directly mounted and frozen in isopentane as described (Brumback and Leech, *Color Atlas of Muscle Histochemistry*, pp. 9-33, PSG Publishing Company, Littleton, Mass., 1984). Ten to 30 µm sections were prepared using a cryostat and stained with hematoxylin and eosin. Muscle fiber numbers were determined from sections taken from the widest part of the tibialis cranialis muscle. Muscle fiber sizes were measured from photographs of sections of tibialis cranialis and gastrocnemius muscles. Fiber type analysis was carried out using the mysosin ATPase assay after pretreatment at pH 4.35 as described (Cumming, et al., *Color Atlas of Muscle Pathology*, pp. 184-185, 1994) and by immunohistochemistry using an antibody directed against type I myosin (MY32, Sigma) and the Vectastain method (Vector Labs); in the immunohistochemical experiments, no staining was seen when the primary antibodies were left out. Carcasses were prepared from shaved mice by removing the all of the internal organs and associated fat and connective tissue. Fat content of carcasses from 4 month old males was determined as described (Leshner, et al., *Physiol. Behavior*, 9: 281, 1972).

For protein and DNA analysis, tissue was homogenized in 150 mM NaCl, 100 mM EDTA. Protein concentrations were determined using the Biorad protein assay. DNA was isolated by adding SDS to 1%, treating with 1 mg/ml proteinase K overnight at 55° C., extracting 3 times with phenol and twice with chloroform, and precipitating with ammonium acetate and EtOH. DNA was digested with 2 mg/ml RNase for 1 hour at 37° C., and following proteinase K digestion and phenol and chloroform extractions, the DNA was precipitated twice with ammonium acetate and EtOH.

Figure 12B:
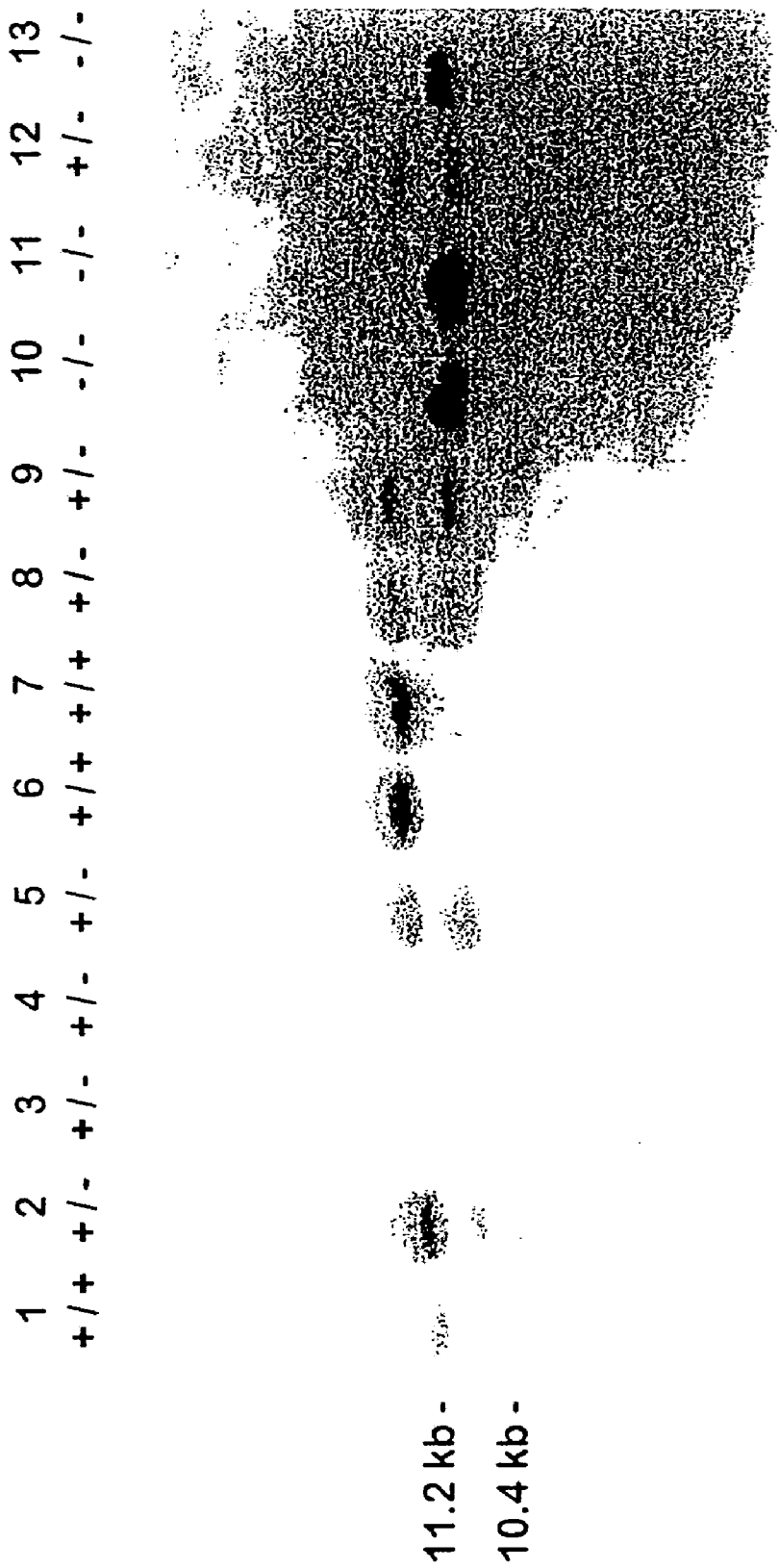
FIG. 12B shows a Southern blot analysis of offspring derived from a mating of heterozygous mutant mice. The lanes are as follows: DNA prepared from wild type 129 SV/J mice (lane 1), targeted embryonic stem cells (lane 2), F1 heterozygous mice (lanes 3 and 4), and offspring derived from a mating of these mice (lanes 5-13).

Homologous targeting of the GDF-8 gene was seen in 13/131 gancyclovir/G418 doubly-resistant ES cell clones. Following injection of these targeted clones into blastocysts, we obtained chimeras from 5 independently-derived ES clones that produced heterozygous pups when crossed to C57BL/6 females (FIG. 12B). Genotypic analysis of 678 offspring derived from crosses of F1 heterozygotes showed 170+/+ (25%), 380+/− (56%), and 128−/− (19%). Although the ratio of genotypes was close to the expected ratio of 1:2:1, the smaller than expected number of homozygous mutants appeared to be statistically significant ($p<0.001$).

Homozygous mutants were viable and fertile when crossed to C57BL/6 mice and to each other. Homozygous mutant animals, however, were approximately 30% larger than their heterozygous and wild type littermates (Table 1). The difference between mutant and wild type body weights appeared to be relatively constant irrespective of age and sex in adult animals. Adult mutants also displayed an abnormal body shape, with pronounced shoulders and hips. When the skin was removed from animals that had been sacrificed, it was apparent that the muscles of the mutants were much larger than those of wild type animals. The increase in skeletal muscle mass appeared to be widespread throughout the body. Individual muscles isolated from homozygous mutant animals weighed approximately 2-3 times more than those isolated from wild type littermates (Table 2). Although the magnitude of the weight increase appeared to roughly correlate with the level of GDF-8 expression in the muscles examined. To determine whether the increased muscle mass could account for the entire difference in total body weights between wild type and mutant animals or whether many tissues were generally larger in the mutants, we compared the total body weights to carcass weights. As shown in Table 3, the difference in carcass weights between wild type and mutant animals was comparable to the difference in total body weights. Moreover, because the fat content of mutant and wild type animals was similar, these data are consistent with all of the total body weight difference resulting from an increase in skeletal muscle mass, although we have not formally ruled out the possibility that differences in bone mass might also contribute to the differences in total body mass.

Figure 13A:
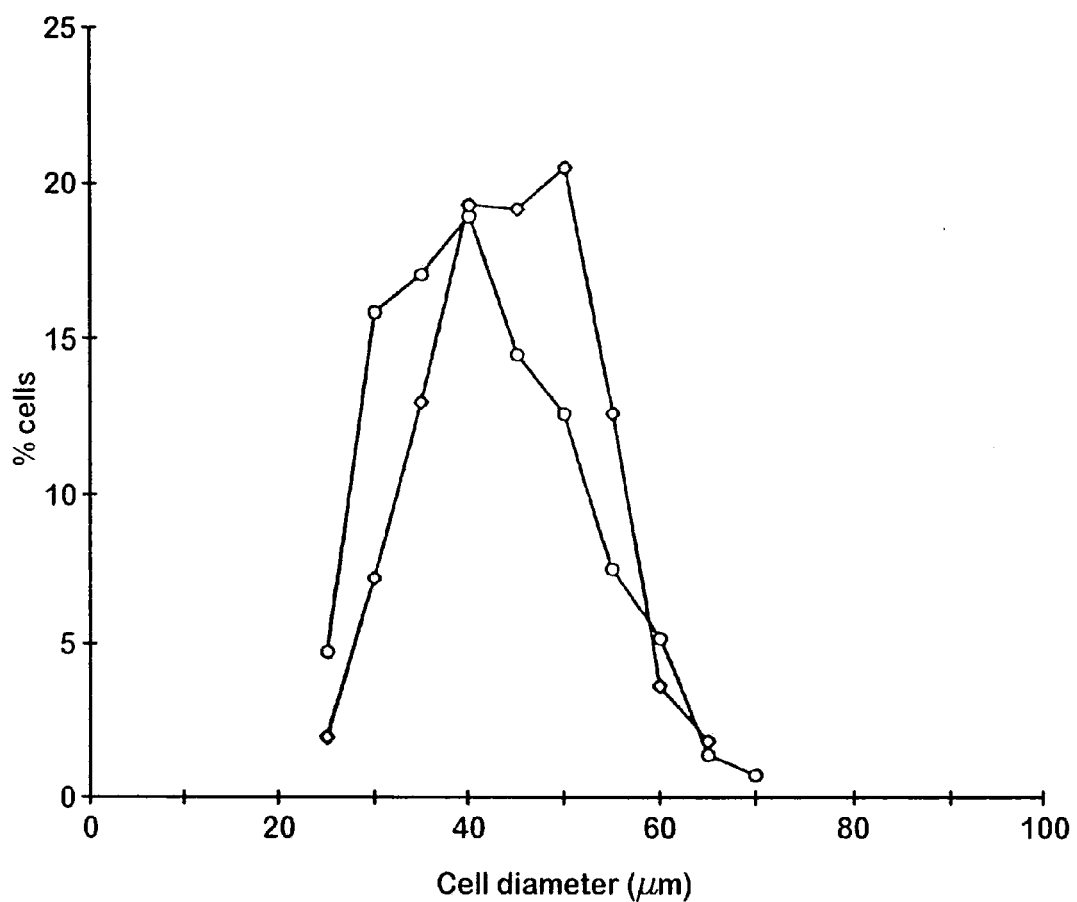
FIG. 13 shows the muscle fiber size distribution in mutant and wild type littermates. Smallest cross-sectional fiber widths were measured for (13A) wild type (n 1761) and mutant (n=1052) tibialis cranial is or (13B) wild type (n=900) and mutant (n =900) gastrocnemius muscles, and fiber sizes were plotted as a percent of total fiber number. Standard deviations were 9 and 10 µm, respectively, for wild type and mutant tibialis cranial is 11 and 9 µm, respectively, for wild type and mutant gastrocnemius muscles. Legend: o-o, wild type; ◇-◇, mutant.
Figure 13B:
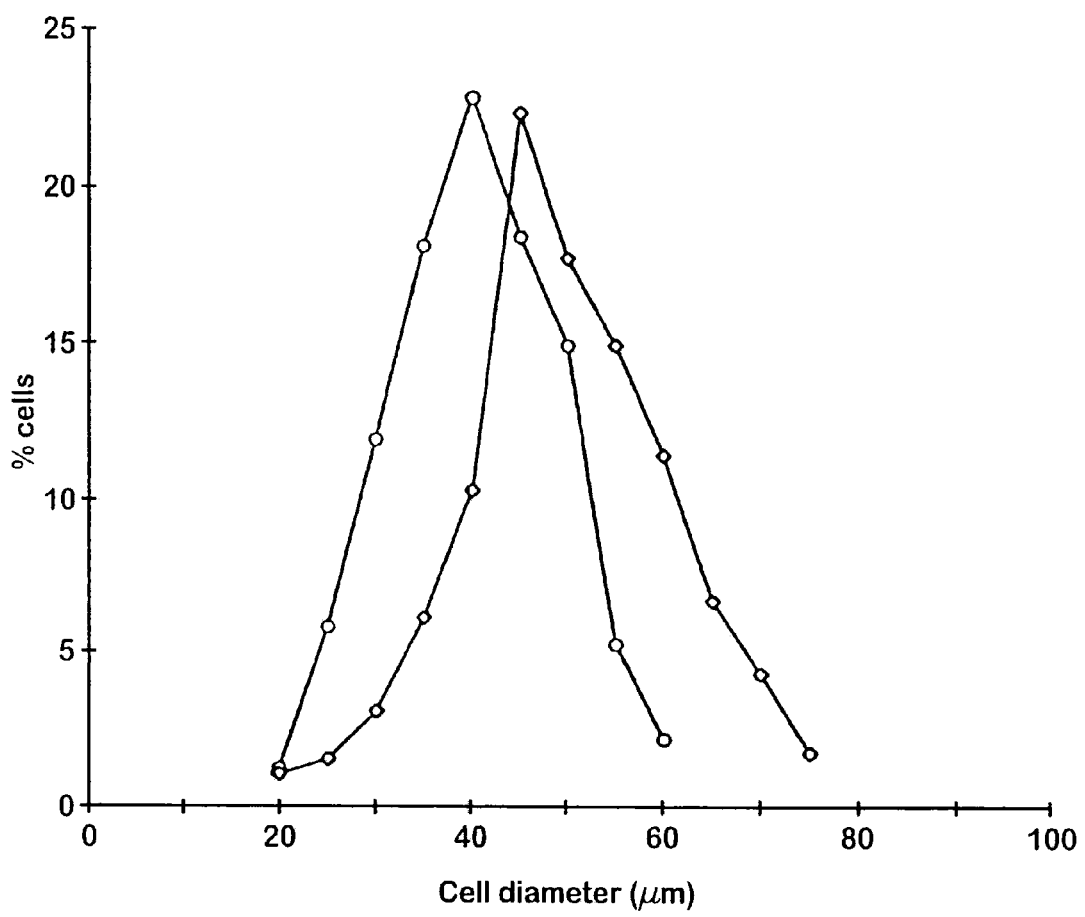

To determine whether the increase in skeletal muscle mass resulted from hyperplasia or from hypertrophy, histologic analysis of several different muscle groups was performed. The mutant muscle appeared grossly normal. No excess connective tissue or fat was seen nor were there any obvious signs of degeneration, such as widely varying fiber sizes (see below) or centrally-placed nuclei. Quantitation of the number of muscle fibers showed that at the widest portion of the tibialis cranialis muscle, the total cell number was 86% higher in mutant animals compared to wild type littermates [mutant=5470+/−121 (n=3), wild type=2936 +/−288 (n=3); $p<0.01$]. Consistent with this result was the finding that the amount of DNA extracted from mutant muscle was roughly 50% higher than from wild type muscle [mutant=350 µg (n=4), wild type=233 µg (n=3) from pooled gastrocnemius, plantaris, triceps brachii, tibialis cranialis, and pectoralis muscles; $p=0.05$]. Hence, a large part of the increase in skeletal muscle mass resulted from muscle cell hyperplasia. However, muscle fiber hypertrophy also appeared to contribute to the overall increase in muscle mass. As shown in FIG. 13, the mean fiber diameter of the tibialis cranialis muscle and gastrocnemius muscle was 7% and 22% larger, respectively, in mutant animals compared to wild type littermates, suggesting that the cross-sectional area of the fibers was increased by approximately 14% and 49%, respectively. Notably, although the mean fiber diameter was larger in the mutants, the standard deviation in fiber sizes was similar between mutant and wild type muscle, consistent with the absence of muscle degeneration in mutant animals. The increase in fiber size was also consistent with the finding that the protein to DNA ratio (w/w) was slightly increased in mutant compared to wild type muscle [mutant=871 +/−111 (n=4), wild type=624 +/−85 (n=3); $p<0.05$].

Finally, fiber type analysis of various muscles was carried out to determine whether the number of both type I (slow) and type II (fast) fibers was increased in the mutant animals. In most of the muscles examined, including the tibialis cranialis muscle, the vast majority of muscle fibers were type II in both mutant and wild type animals. Hence, based on the cell counts discussed above, the absolute number of type II fibers were increased in the tibialis cranialis muscle. In the soleus muscle, where the number of type I fibers was sufficiently high that we could attempt to quantitate the ratio of fiber types could be quantitated, the percent of type I fibers was decreased by approximately 33% in mutant compared to wild type muscle [wild type=39.2 +/−8.1 (n=3), mutant=26.4 +/−9.3 (n=4)]; however, the variability in this ratio for both wild type and mutant animals was too high to support any firm conclusions regarding the relative number of fiber types.

EXAMPLE 9

Isolation of Rat and Chicken GDF-8

In order to isolate rat and chicken GDF-8 cDNA clones, skeletal muscle cDNA libraries prepared from these species were obtained from Stratagene and screened with a murine GDF-8 probe. Library screening was carried out as described previously (Lee, Mol. Endocranial., 4:1034-1040) except that final washes were carried out in 2×SSC at 65° C. Partial sequence analysis of hybridizing clones revealed the presence of open reading frames highly related to murine and human GDF-8. Partial sequences of rat and chicken GDF-8 are shown in FIGS. 2C and 2D, respectively, and an alignment of the predicated rat and chicken GDF-8 amino acid sequences with those of murine and human GDF-8 are shown in FIG. 3B. All four sequences contain an RSRR sequence that is likely to represent the proteolytic processing site. Following this RSRR sequence, the sequences contain a C-terminal region that is 100% conserved among all four species. The absolute conservation of the C-terminal region between species as evolutionarily far apart as humans and chickens suggests that this region will be highly conserved in many other species as well.

Although the invention has been described with reference to the presently preferred embodiment, it should be understood that various modifications can be made without departing from the spirit of the invention. Accordingly, the invention is limited only by the following claims.

What is claimed is:

1. Substantially pure growth differentiation factor-8 (GDF-8) having the amino acid sequence as set forth in SEQ ID NO:21.

2. A composition comprising the GDF-8 of claim 1 and a pharmaceutically acceptable carrier.

3. A fragment of the GDF-8 of claim 1 having the activity of modulating muscle growth.

4. A composition comprising the fragment of claim 3 and a pharmaceutically acceptable carrier.

* * * * *